United States Patent [19]
Tang et al.

[11] Patent Number: 6,107,076
[45] Date of Patent: Aug. 22, 2000

[54] SOLUBLE MAMMALIAN ADENYLYL CYCLASE AND USES THEREFOR

[75] Inventors: Wei-Jen Tang, Chicago, Ill.; Alfred G. Gilman, Dallas, Tex.

[73] Assignee: Board of Regents, The University of Texas System, Austin, Tex.

[21] Appl. No.: 08/726,214

[22] Filed: Oct. 4, 1996

Related U.S. Application Data

[60] Provisional application No. 60/005,498, Oct. 4, 1995.
[51] Int. Cl.$^7$ .............................. C12N 9/88; C12N 15/60; C12N 15/62; C12N 15/85
[52] U.S. Cl. ...................... 435/232; 435/67.1; 435/69.7; 435/252.3; 435/320.1; 536/23.2; 536/23.4; 536/23.5; 935/14; 935/29; 935/32; 935/47
[58] Field of Search ........................... 424/94.1; 435/232, 435/320.1, 252.3, 325; 536/23.2, 23.4

[56] References Cited

PUBLICATIONS

Bakalyar and Reed, "Identification of a Specialized Adenylyl Cyclase that May Mediate Odorant Detection," *Science*, 250:1403–1406, (1990).

Berlot and Bourne, "Identification of Effector–Activating Residues of $G_{s\alpha}$," *Cell*, 68:911–922, (1992).

Cali et al., "Type VIII Adenylyl Cyclase," *J. Biol. Chem.*, 269(16):12190–12195, (1994).

Coleman et al., :Structures of Active Conformations of $G_{i\alpha 1}$ and the Mechanism of GTP Hydrolysis, *Science*, 265:1405–1412, (1994).

Dessauer and Gilman, "Purification and Characterization of a Soluble Form of Mammalian Adenylyl Cyclase," *J. Biol. Chem.*, 271(28):16967–16974, (1996).

Feinstein et al., "Molecular Cloning and Characterization of a $Ca^{2+}$/Calmodulin–Insensitive Adenylyl Cyclase from Rat Brain," *Proc. Natl. Acad. Sci. USA*, 88:10173–10177, (1991).

Florio and Ross, "Regulation of the Catalytic Component of Adenylate Cyclase. Potentiative Interaction of Stimulatory Ligands and 2',5'–Dideoxyadenosine," *Mol. Pharm.*, 24:195–202, (1983).

Gao and Gilman, "Cloning and Expression of a Widely Distributed (Type IV) Adenylyl Cyclase," *Proc. Natl. Acad. Sci. USA*, 88:10178–10182, (1991).

Graziano and Gilman, Synthesis in *Escherichia coli* of GTPase–deficient Mutants of $G_{s\alpha}$, *J. Biol. Chem.*, 264(26):15475–15482, (1989).

Hepler et al., "Functional Importance of the Amino Terminus of $G_{q\alpha}$," *J. Biol. Chem.*, 271(1):496–504,(1996).

Johnson and Shoshani, "Kinetics of P–Site–Mediated Inhibition of Adneylyl Cyclase and the Requirements for Substrate," *J. Biol. Chem.*, 265(20): 11595–11600, (1990).

Katsushika et al., "Cloning and Characterization of a Sixth Adenylyl Cyclase Isoform: Types V and VI Constitute a Subgroup Within the Mammalian Adenylyl Cyclase Family," *Proc. Natl. Acad. Sci. USA*, 89:8774–8778, (1992).

Kozasa and Gilman, "Protein Kinase C Phosphorylates $G_{12\alpha}$ and Inhibits its Interaction with $G_{\beta\gamma}$," *J. Biol. Chem.*, 271(21):12562–12567, (1996).

Krupinski et al., "Adenylyl Cyclase Amino Acid Sequence: Possible Channel– or Transporter–Like Structure," *Science*, 244:1558–1564, (1989).

(List continued on next page.)

*Primary Examiner*—Robert A. Wax
*Assistant Examiner*—William W. Moore
*Attorney, Agent, or Firm*—Arnold, White & Durkee

[57] ABSTRACT

A soluble form of adenylyl cyclase and methods of its use in screening for stimulators and inhibitors of adenylyl cyclase activity are disclosed. In one embodiment, a chimera of type I and type II adenylyl cyclases is provided. This chimera lacks transmembrane domains characteristic of adenylyl cyclases, rendering the recombinant product soluble, while retaining adenylyl cyclase function.

27 Claims, 13 Drawing Sheets

PUBLICATIONS

Krupinski et al., "Molelcular Diversity in the Adenylylcyclase Family," *J. Biol. Chem.*, 267(34):24858–25862, (1992).

Morris et al., "Localization of the Forskolin Labeling Sites to Both Halves of P–Glycoprotein: Similarity of the Sites Labeled by Forskolin and Prazosin," *Mol. Pharm.*, 46:329–337, (1994).

Neer et al., "Increase in the Size of Soluble Brain Adenylate Cyclase with Activation by Guanosine 5'–(β,γ–Imino)triphosphate," *J. Biol. Chem.*, 255(20):9782–9789, (1980).

Noel et al., "The 2.2 Å Crystal Structure of Transducin–α Complexed with GTPγS," *Nature*, 355:654–663, (1993).

Pfeuffer et al., "Catalytic Unit of Adenlyate Cyclase: Purification and Identification by Affinity Crosslinking," *Proc. Natl. Acad. Sci. USA*, 82:3086–3090, (1985).

Premont et al., "Two Members of a Widely Expressed Subfamily of Hormone–Stimulated Adenylyl Cyclases," *Proc. Natl. Acad. Sci. USA*, 89:9809–9813, (1992).

Schreibmayer et al., "Inhibition of an Inwardly Rectifying K+ Channel by G–Protein α–Subunits," *Nature*, 380:624–627, (1996).

Seamon et al., "Structure–Activity Relationships for Activation of Adenylate Cyclase by the Diterpene Forskolin and its Derivatives," *J. Med. Chem.*, 26:436–439, (1983).

Smigel, "Purification of the Catalyst of Adenylate Cyclase," *J. Biol. Chem.*, 261(4):1976–1982, (1986).

Sutkowski et al., "Regulation of Forskolin Interactions with Type I, II, V, and VI Adenylyl Cyclases by $G_{s\alpha}$," *Biochemistry*, 33:12852–12859, (1994).

Tang and Gilman, "Construction of a Soluble Adenylyl Cyclase Activated by $G_s\alpha$ and Forskolin," *Science*, 268:1769–1772, (1995).

Tang et al., "Truncation and Alanine–Scanning Mutants of Type I Adneylyl Cyclase," *Biochemistry*, 34:14563–14572, (1995).

Tang et al., "Regulation of Mammalian Adenylyl Cyclases by G–Protein α and βγ Subunits," Cold Spring Harbor Symposia on Quantitative Biology, vol. LVII, Cold Spring Harbor Laboratory Press, p. 135–144, (1992).

Tang and Gilman, "Adenylyl Cyclases," (Minireview), *Cell*, 70:869–872, (1992).

Tang et al., "Expression and Characterization of Calmodulin–Activated (Type I) Adenylylcyclase," *J. Biol. Chem.*, 266(13):8595–8603, (1991).

Taussig and Gilman, "Mammalian Membrane–Bound Adenylyl Cyclases," (Minireview), *J. Biol. Chem.*, 270(1):1–4, (1995).

Taussig et al., "Expression and Purification of Recombinant Adenylyl Cyclases in Sf9 Cells," *Methods in Enzymology*, 238:95–108, (1994).

Wadzinski et al., "Localization of the Forskolin Photolabelling Site within the Monosaccharide Transporter of Human Erythrocytes," *Biochem. J.*, 272:151–158, (1990).

Wallach et al., "Molecular Cloning and Expression of a Novel Type V Adenylyl Cyclase from Rabbit Myocardium," *FEBS Letter*, 338:257–263, (1994).

Watson et al., "Molecular Cloning and Characterization of the Type VII Isoform of Mammalian Adenylyl Cyclase Expressed Widely in Mouse Tissues and in S49 Mouse Lymphoma Cells," *J. Biol. Chem.*, 269(46):28893–28898, (1994).

Whisnant et al., "Interaction of the Two Cytosolic Domains of Mammalian Adenylyl Cyclase," *Proc. Natl. Acad. Sci. USA*, 93:6621–6625, (1996).

Yoshimura and Cooper, "Cloning and Expression of a $Ca^{2+}$–Inhibitable Adenylyl Cyclase from NCB–20 Cells," *Proc. Natl. Acad. Sci. USA*, 89:6716–6720, (1992).

Iyengar, Molecular and Functional Diversity of Mammalian $G_s$–Stimulated Adenylyl Cyclases, *FASEB Journal*, 7:768–775, 1993.

Glaser, P. et al. "The calmodulin–sensitive adenylate cyclase of *Bortella pertussis:* cloning and expression in *Escherichia coli*" Molecular Microbiology (1988), vol. 2, No. 1, pp. 19–30.

Taussig, R. et al. "Regulation of purified type I and type II adenylylcylases by G protein betagamma subunits" Journal of Biological Chemistry (Jan. 5, 1993), vol. 268, No. 1, pp. 9–12.

Nakane, M. et al. "Molecular cloning and expression of cDNAs coding for soluble guanylate cyclase from rat lung" Journal of Biological Chemistry (Oct. 5, 1990), vol. 265, No. 28, pp. 16841–16845.

SOLUBLE MAMMALIAN ADENYLYL CYCLASE AND USES THEREFOR

The present application claims benefit of the priority accorded to provisional application Ser. No. 60/005,498 filed on Oct. 4, 1995. The entire text of the aforementioned disclosure is specifically incorporated by reference herein without disclaimer.

The government may own certain rights in the present invention pursuant to grant number GM34497 from the National Institutes of Health.

BACKGROUND OF THE INVENTION

1. Field of the Invention

The present invention relates generally to the field of molecular pharmacology. More specifically, the invention involves the molecular biology of the adenylyl cyclase pathway and, in particular, the structure and function of the enzyme adenylyl cyclase.

2. Description of the Related Art

Cyclic AMP regulates intracellular reactions in all nucleated animal cells studied to date. The system by which cyclic AMP is produced is the adenylyl cyclase system, which comprises G-protein coupled receptors, G-proteins and the catalytic, membrane-bound enzyme known as adenylyl cyclase. Adenylyl cyclases have molecular weights of about 120 kD and are stimulated directly by the diterpene forskolin.

The structures of G protein-regulated adenylyl cyclases are complex, consisting of two intensely hydrophobic domains ($M_1$ and $M_2$ with each hypothesized to contain six transmembrane helices) and two approximately 40 kD cytosolic domains ($C_1$ and $C_2$). $C_1$ and $C_2$ contain sequences ($C_{1a}$ and $C_{2a}$) that are similar to each other, to corresponding regions of related adenylyl cyclases and to the catalytic domains of the related membrane-bound, soluble guanylyl cyclases (Tang and Gilman, 1992). Analysis of a series of truncation and alanine-scanning mutants of mammalian adenylyl cyclases indicated that both $C_{1a}$ and $C_{2a}$ (but not $C_{1b}$ and $C_{2b}$) are necessary for catalytic activity (Tang et al., 1992).

Unfortunately, membrane-bound adenylyl cyclases are found in small amounts and the enzymes are both labile and difficult to manipulate in detergent-containing solutions. As a result, biochemical studies on the mechanism of regulation of adenylyl cyclases have been relatively unrewarding. Improved methods for isolation of this enzyme, relying on a forskolin affinity matrix, have permitted some purification. Recombinant expression has proved difficult as well, as the significant transmembrane regions of adenylyl cyclases create significant technical problems, especially in prokaryotic expression systems. Thus, there remains a need to develop improved reagents and assays that can be used to further characterize adenylyl cyclase and to screen for compounds that stimulate and inhibit adenylyl cyclase activity.

SUMMARY OF THE INVENTION

In light of the limitations described above, a goal of the present invention is to provide soluble forms of adenylyl cyclase that display normal regulatory function, and methods of production thereof. In addition, it is a goal to provide assays for the screening of inhibitors of adenylyl cyclase activity.

Thus, it is a goal of the present invention to provide adenylyl cyclase compositions that will be suitable for use in exploring the function of this enzyme. In addition, it is a goal to provide methods of synthesizing these compositions. Finally, it is a goal to provide methods of identifying inhibitors of adenylyl cyclase.

In fulfilling these goals, there is provided a soluble polypeptide composition having adenylyl cyclase activity. The polypeptide composition generally comprises one or more polypeptides that lack transmembrane regions.

In one embodiment, the polypeptide composition comprises a chimera of adenylyl cyclase $C_1$ and $C_2$ domains linked covalently. For example, the chimera may consist essentially of adenylyl cyclase type I-$C_1$ and type II-$C_2$ domains, more specifically, wherein the type I-$C_1$ domain is a $C_{1a}$ domain sequence from SEQ ID NO:2 and the type II-$C_2$ domain is a $C_{2a}$ domain sequence from SEQ ID NO:4. In another example, the chimera consists essentially of adenylyl cyclase type V-$C_1$ and type II-$C_2$ domains. The domains may be joined by a linker peptide, for example, a linker peptide having a sequence selected from the group consisting of AAAGGM (SEQ ID NO:19), AAAGGMPPAAAGGM (SEQ ID NO:20) and AAAGGM(PPAAAGGM)$_2$ (SEQ ID NO:21).

In an alternative embodiment, the polypeptide composition according to claim 2, wherein the polypeptide composition forms a complex comprising two distinct polypeptides, one of which is an adenylyl cyclase $C_1$ domain and one of which is an adenylyl cyclase $C_2$ domain. For example, the complex has a $C_1$ domain that is a type I $C_1$ domain and a $C_2$ domain that is a type II $C_2$ domain, more specifically, the type I-$C_1$ domain has a $C_{1a}$ domain sequence from SEQ ID NO:2 and the type II-$C_2$ domain has a $C_{2a}$ domain sequence from SEQ ID NO:4. Alternatively, the $C_1$ domain is a type V $C_1$ domain the $C_2$ domain is a type II $C_2$ domain.

In another embodiment of the present invention, there is provided a polynucleotide encoding a soluble polypeptide having adenylyl cyclase activity. Generally, the polynucleotide does not encode transmembrane regions. In one embodiment, the polynucleotide encodes a chimera of adenylyl cyclase $C_1$ and $C_2$ domains, for example, as in SEQ ID NO:17. Alternatively, the polynucleotide encode an adenylyl cyclase $C_1$ or $C_2$ domain. Expression vectors, wherein these polynucleotides are operably linked to a promoter, and host cells comprising such expression vectors, also are contemplated. The host cells may be bacterial in origin or they may be mammalian cells, especially insect cells that are capable of supporting baculovirus replication. In a specific embodiment, the host cell further comprises an expression vector comprising a polynucleotide encoding the alpha subunit of G protein, operably linked to a promoter active in the host cell.

In yet another embodiment, there is provided a method for determining the effects of an agent on adenylyl cyclase activity comprising the steps of (i) providing a soluble polypeptide composition having adenylyl cyclase activity; (ii) contacting the polypeptide composition with the agent; and (iii) measuring the adenylyl cyclase activity of the polypeptide composition. The polypeptide composition generally will lack a transmembrane region. In one embodiment, the polypeptide composition is a chimera of adenylyl cyclase type $C_1$ and $C_2$ domains. In another embodiment, the composition forms a complex comprising two distinct polypeptides, one of which is an adenylyl cyclase $C_1$ domain and one of which is an adenylyl cyclase $C_2$ domain.

As part of this method, the providing may comprise transforming a host cell with an expression vector comprising a polynucleotide encoding the chimera, operably linked to a promoter active in the host cell. The method also may further comprise transforming the host cell with an expression vector comprising a polynucleotide encoding the alpha subunit of G protein, operably linked to a promoter active in the host cell. The growth of the host cell may be conditional on adenylyl cyclase activity and the measuring comprises assessing the growth of the host cell, for example, growth on minimal agar. Alternatively, the method may function such that the maltose utilization of the host cell is conditional on the absence of adenylyl cyclase activity and the measuring comprises assessing the maltose utilization of the host cell, wherein the transformed host cell is a bacterial cell and growth is on McConkey agar.

In an alternatively embodiment, the providing step may comprise transforming a host cell with two expression vectors, one of the expression vectors comprising a polynucleotide encoding an adenylyl cyclase $C_1$ domain, operably linked to a promoter active in the host cell, and the other expression vector comprising a polynucleotide encoding an adenylyl cyclase $C_2$ domain, operably linked to a promoter active in the host cell. Finally, the providing step may comprise (a) transforming a first host cell with a first expression vector comprising a polynucleotide encoding an adenylyl cyclase $C_1$ domain, operably linked to a promoter active in the host cell, (b) transforming a second host cell with a second expression vector comprising a polynucleotide encoding an adenylyl cyclase $C_2$ domain, operably linked to a promoter active in the host cell, (c) isolating the $C_1$ and $C_2$ domains, and (d) admixing the isolated $C_1$ and $C_2$ domains under conditions permitting formation of the complex.

In still yet another embodiment, there is provided a method of producing a soluble adenylyl cyclase complex comprising the steps of (a) transforming a first host cell with a first expression vector comprising a polynucleotide encoding an adenylyl cyclase $C_1$ domain, operably linked to a promoter active in the host cell, (b) transforming a second host cell with a second expression vector comprising a polynucleotide encoding an adenylyl cyclase $C_2$ domain, operably linked to a promoter active in the host cell, (c) isolating the $C_1$ and $C_2$ domains, and (d) admixing the isolated $C_1$ and $C_2$ domains under conditions permitting formation of the complex. The complex may have a $C_1$ domain that is a type I $C_1$ domain and a $C_2$ domain that is a type II $C_2$ domain. Alternatively, the complex may have a $C_1$ domain that is a type V $C_1$ domain and a $C_2$ domain that is a type II $C_2$ domain.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

In FIG. 7B, adenylyl cyclase was activated with forskolin. In FIG. 7A, adenylyl cyclase was assayed with forskolin (○), GTPγS-$G_{s\alpha}$ (●), or forskolin plus GTPγS-$G_{s\alpha}$ (□); control activities for these conditions were 270, 95 and 970 pmol/min/mg, respectively. Data shown are representative of at least two studies.

(FIG. 10B) Increasing amounts of a lysate containing $IIC_2$ were mixed with 1 µg of the $Ni^{2+}$-NTA column eluate containing $IC_1$ and assayed with 50 µM FSK.

(FIG. 11A) Mono Q column chromatography. Fractions were 6 ml. (FIG. 11B) Gel filtration over Superdex 200. Fractions were 0.5 ml. The positions of molecular weight markers are shown.

FIG. 12A and FIG. 12B. Purification of $IC_1$. (FIG. 12A) Phenyl-Sepharose column chromatography. Fractions were 2 ml. The first peak of activity was pooled for further purification. (FIG. 12B) Gel filtration over Superdex 200. Fractions were 0.5 ml. The positions of molecular weight markers are shown.

(FIG. 13A) The indicated concentrations of $IIC_2$ were assayed in the presence of 0.1 µM $IC_2$ for 30 min. In the absence of activators. (FIG. 13B) The indicated concentrations of $IIC_2$ were assayed in the presence of 8 nM $IC_1$ for 10 min. With either 50 µM FSK (●) or 50 µM FSK plus 10 µM GTP[γS]-$G_{s\alpha}$ (●). Activities are expressed per mg of $IC_1$.

(FIG. 14A) Fragments $IIC_2$ (6.6 μM) and $IC_1$ (8 nM) were mixed and assayed in the presence of the indicated concentrations of FSK, with (■) or without (●) 0.5 μM GTP[γS]-$G_{s\alpha}$ (FIG. 14B) Fragments $IIC_2$ (6.6 μM) and $IC_1$ (8 nM) were mixed and assayed in the presence of the indicated concentrations of GTP[γS]-$G_{s\alpha}$, with (■) or without (●) 50 μM FSK.

DETAILED DESCRIPTION OF THE PREFERRED EMBODIMENTS

Figure 1A:
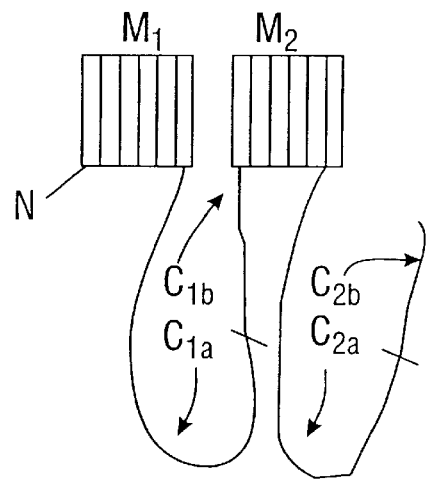
FIG. 1A and FIG. 1B—Chimeric adenlyl cyclase. A model of mammalian adenylyl cyclase (FIG. 1A) and the various chimeras between type I and type II adenylyl cyclases (FIG. 1B) are shown. Also illustrated are the linker sequences (SEQ ID NO:19, SEQ ID NO:20 and SEQ ID NO:21. $IC_{1a}$ includes residues 271–484 of type I adenylyl cyclase; $IIC_{2a}$ includes residues 821–1090 of type II adenylyl cyclase. No sequences from any of the putative transmembrane spans of either enzyme are included.

One of the primary reasons that research on adenylyl cyclase has been limited is that it has been difficult to purify significant quantities of the active enzyme. Even when improved methods permitted isolation, the ability of the purified enzyme has further hampered efforts. An alternative—recombinant production—also has proved problematic, largely because of the two hydrophobic transmembrane regions found in adenylyl cyclases. It has proved difficult to synthesize active enzymes containing significant transmembrane regions because of the loss of higher order structure in the absence of membranes. The present invention has overcome this problem by providing adenylyl cyclase compositions lacking transmembrane regions but retaining activity and characteristic regulatory features. The following describes the present invention in detail.

1. Adenyl Cyclase and Nucleic Acids Coding Therefor

Adenylyl cyclases are enzymes of approximately 120 kD (1064–1248 amino acids). There currently are eight different isoforms known, designated I–VIII. The typical structure of adenylyl cyclase begins with a short cytoplasmic amino terminus followed by a first hydrophobic region comprising six transmembrane spans ($M_1$). This is followed by a first cytoplasmic domain of about 40 kD ($C_1$). A second six-span transmembrane region ($M_2$) and a second cytoplasmic domain ($C_2$) follow. While there is no evidence that adenylyl cyclases are membrane channels or transporters, their structure is reminiscent of molecules having these functions.

The overall amino acid sequence similarity among the different adenylyl cyclases is roughly 50%. Within each of the two cytoplasmic regions, there are more highly conserved regions, designated $C_{1a}$ and $C_{2a}$. These domains show considerable homology between isoforms and across species of adenylyl cyclases. In addition, $C_{1a}$ and $C_{2a}$ are structurally related to the catalytic domains of guanylyl cyclases. Interestingly, $C_{1a}$ and $C_{2a}$ show similarity to each other as well.

Because of the difficulties associated with recombinant expression of polypeptides containing membrane-spanning regions, it is desirable to identify functional catalytic subunits within adenylyl cyclases. Attempts to detect adenylyl cyclase activity following expression of the $C_{1a}$ or $C_{2a}$ regions individually have not been successful, however. Similarly, individual expression of $C_1$, $C_2$, $M_1C_1$ or $M_2C_2$ has not been accompanied by detectable cyclase activity.

When $M_1C_1$ and $M_2C_2$ are coexpressed in the same cell, however, cyclase activity is observed. Thus, at a minimum, function of adenylyl cyclase apparently requires some level of interaction between the $C_1$ and $C_2$ domains. Whether or not the transmembrane regions were necessary for this function remained unknown prior to the present invention. As shown herein, however, chimeras and non-covalent complexes of the $C_{1a}$ and $C_{2a}$ domains of adenylyl cyclases types I and II, respectively, which completely lack the membrane-spanning regions, also exhibit regulated adenylyl cyclase activity. This also suggests that $C_1$ and $C_2$ interaction is important and, further demonstrates that the transmembrane regions are not required for enzymatic function. It is further demonstrated that mixtures of C1 and C2 domains adenylyl cyclases of types I, II and V, likewise completely lacking membrane spanning regions exhibit regulatable adenylyl cyclase activity.

Some other structural constraints on adenylyl cyclase function may also exist. Studies indicate that one particular recombinant enzyme consisting of the $C_{1a}$ and $C_{2a}$ regions of type I adenylyl cyclase, made as described herein, may not be active. Alternatively, this lack of activity may be a function of the kind of linkage used to connect the two domains. A similar type I/type II chimera is functional, however. Given the instant disclosure, it would be a simple matter to synthesize any of the 64 possible combinations of $C_{1a}$ and $C_{2a}$ regions to determine which provide functional enzymes (Table 1) using the techniques described in the Examples.

TABLE 1

The possible combinations of C1a and C2a

| | | C1a Type | | | | | | | |
|---|---|---|---|---|---|---|---|---|---|
| | | I | II | III | IV | V | VI | VII | VIII |
| C2a Type | I | I/I | II/I | III/I | IV/I | V/I | VI/I | VII/I | VIII/I |
| | II | I/II | II/II | III/II | IV/II | V/II | VI/II | VII/II | VIII/II |
| | III | I/III | II/III | III/III | IV/III | V/III | VI/III | VII/III | VIII/III |
| | IV | I/IV | II/IV | III/IV | IV/IV | V/IV | VI/VI | VII/IV | VIII/IV |
| | V | I/V | II/V | III/V | IV/V | V/V | VI/V | VII/V | VIII/V |
| | VI | I/VI | II/VI | III/VI | IV/VI | V/VI | VI/VI | VII/VI | VIII/VI |
| | VII | II/VII | II/VII | III/VII | IV/VII | V/VII | VI/VII | VII/VII | VIII/VII |
| | VIII | I/VIII | II/VIII | III/VIII | IV/VIII | V/VIII | VI/VIII | VII/VIII | VIII/VIII |

The nucleic acid and amino acid sequences for the various adenylyl cyclases are known to those of skill in the art, are described in numerous published articles, and are available from publicly accessible databases. By way of example only, Krupinski et al. (1989) describe the nucleic acid and amino acid sequences for type I adenylyl cyclase; Feinstein et al. (1991) describe type II adenylyl cyclase sequences; Bakalyar & Reed (1990) describe type III adenylyl cyclase sequences; Gao & Gilman (1991) describe type IV adenylyl cyclase sequences; Premont et al. (1992) describe type V and VI adenylyl cyclase sequences; Krupinski et al. (1992) and Katsushika et al. (1992) particularly describe VI adenylyl cyclase sequences; Watson et al. (1994) describe type VII adenylyl cyclase sequences; and Cali et al. (1994) describe type VIII adenylyl cyclase sequences. The foregoing articles and others concerning adenylyl cyclase genes and cDNAs, such as Yoshimura & Cooper (1992) and Wallach et al. (1994), are each incorporated herein by reference.

In addition to the foregoing articles, various exemplary mammalian adenylyl cyclase nucleic acid and amino acid sequences are provided in the present sequence listing. The nucleic acid and amino acid sequence of type I are exemplified by SEQ ID NO:1 and SEQ ID NO:2, respectively. Similarly, SEQ ID NO:3 and SEQ ID NO:4 represent type II adenylyl cyclase; SEQ ID NO:5 and SEQ ID NO:6 represent type III; SEQ ID NO:7 and SEQ ID NO:8 represent type IV; SEQ ID NO:9 and SEQ ID NO:10 represent type V; SEQ ID NO:11 and SEQ ID NO:12 represent type VI; SEQ ID NO:13 and SEQ ID NO:14 represent type VII; and SEQ ID NO:15 and SEQ ID NO:16 represent type VIII adenylyl cyclase.

The nucleic acid and amino acid sequences for the exemplified chimera are provided in SEQ ID NO:17 and SEQ ID NO:18, respectively. Various other chimeric constructs are readily preparable using the sequence information of the present disclosure and standard molecular biological linker technology, e.g., using the peptide linker sequences in combination with the codon information in Table 4.

One of the important benefits deriving from the deletion of the transmembrane regions is the production of an adenylyl cyclase that is soluble. "Soluble" is defined here in as capable of dissolving in a aqueous environment in the absence of detergent.

It will be understood that the soluble adenylyl cyclase compositions provided by the invention represents a significant advantage over the prior art in that the previous methods required either preparation of membrane fractions (e.g., Feinstein et al., 1991; Katsushika et al., 1992; Cali et al., 1994) or solubilization in detergent (see e.g., Tang et al., 1991). Even expression of the protein in a membrane environment was not always successful. For example, Gao and Gilman (1991) reported that expression of type IV adenylyl cyclase in Sf9 cell membranes was associated with a considerable amount of denaturation and/or aggregation.

A detergent commonly used prior to the present invention is Lubrol PX. However, even using detergent solubilization, the prior art methods were not always successful in extracting or isolating recombinant adenylyl cyclase. For example Tang et al. (1991) reported only a 50–60% efficiency of solubilization for recombinant adenylyl cyclase (Table I of Tang et al., 1991).

Other detergents that have been used previously in attempts to solubilize and purify adenylyl cyclase include cholate, digitonin, CHAPS, octylglucoside and dodecylmaltoside in the presence of glycerol and NaCl (Taussig et al., 1994). Therefore, this invention may be characterized as an adenylyl cyclase preparation that is soluble in an aqueous environment in the absence of a significant amount of a detergent such as Lubrol PX, cholate, digitonin, CHAPS, octylglucoside or dodecylmaltoside in the presence of glycerol and NaCl.

Also, in the prior art methods, in further purification from the initial detergent solubilization step, recovery of the adenylyl cyclase protein was reported to be only about 10% of the total protein (Tang et al., 1991). Furthermore, after purification, the adenylyl cyclase protein of the prior art did not exhibit the expected properties, such as being inhibited by βγ, even though the impure protein preparation did exhibit such properties. By providing soluble adenylyl cyclase that displays normal properties and regulatory functions, the present invention marks a breakthrough in this area.

It is contemplated that the precise form of the chimeric or complexed adenylyl cyclase compositions may vary without adversely affecting its function. For example, there is no particular constraint on the precise size of the catalytic domains and their potential fusion sites so long as essential sequences are included. Similarly, in the chimeric compositions the mode of fusion (direct versus spacer linked) may differ from construct to construct.

The domains of the soluble adenylyl cyclase chimeric compositions will likely most often be joined by a spacer peptide, generally of a flexible nature, although other chemical linkages are not excluded. Currently, it is contemplated that the most useful linker sequences will generally be peptides of between about 6 and about 40 amino acids in length, or so, with linkers of between about 6 and about 25 amino acids in length being more preferred. These linkers are produced by using synthetic, linker-encoding oligonucleotides to couple the $C_{1a}$ and $C_{2a}$ coding regions.

Peptide linkers with a degree of flexibility will generally be preferred. The linking peptides may have virtually any amino acid sequence, bearing in mind that the preferred linkers will have a sequence that results in a generally flexible peptide. The use of small amino acids, such as glycine and alanine, will likely be of use in creating a flexible peptide. The creation of such sequences will be routine to those of skill in the art.

A variety of different linkers are commercially available and are considered suitable for use according to the present invention. Amino acid sequences rich in alanine and proline residues are known to impart flexibility to multi-domain protein structures. For example, such sequences are to be found linking the domains of the so-called E2 components of the 2-oxo acid dehydrogenase complexes, such as pyruvate dehydrogenase complex and 2-oxo glutarate dehydrogenase complex (Perham et al., 1981; Perham & Roberts, 1981; Texter et al., 1988; Miles et al., 1988; Radford et al., 1987, 1989). Alanine-proline rich regions are also found in myosin light chains (Henry et al., 1982). Exemplary linkers for use in the invention have a combination of glycine, alanine, proline and methionine residues, such as AAAGGM (SEQ ID NO:19), AAAGGMPPAAAGGM (SEQ ID NO:20) and AAAGGM(PPAAAGGM$_2$ (SEQ ID NO:21). However, any flexible linker generally between about 6 and about 40 amino acids in length, or so, may be used. Linkers may have virtually any sequence that results in a generally flexible peptide, including alanine-proline rich sequences of the type exemplified above.

It also may be desirable to include additional sequences or "tags" not related to adenylyl cyclase function. For purposes of isolation, one may include in the construct a short peptide for which a binding partner is readily available. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.) and the 6xHis system (Qiagen, Chatsworth, Calif.). Some of these systems produce fusions bearing only a small number of additional amino acids which are unlikely to affect the structure of the recombinant product.

For example, both the FLAG system and the 6xHis system add only short sequences, both of which are known to be poorly antigenic and which do not adversely affect folding of the protein to its native conformation. Indeed, the 6xHis fusion protein has already been generated and purified. This molecule has been purified to essential homogeneity by three sequential chromatographic steps—Qiagen Ni+ column; mono Q chromatography; phenyl superose chromatography. The purified fusion protein has a specific activity of 13 μg/min/mg, essentially the same as purified type I or type II adenylyl cyclase. The fusion protein is activated synergistically by $G_{s\alpha}$ and forskolin, and it is inhibited by G protein βγ subunits and P-site inhibitors, e.g., 2'-deoxy-3'-AMP.

With other fusion systems, it is desirable to excise the tag from the desired product. In a preferred embodiment, the tag is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

More subtle changes may be made in the amino acid sequences provided herein while retaining a molecule having appropriate structure and function. For example, certain amino acids may be substituted for other amino acids in a protein structure without appreciable loss of structural and functional integrity. These "conservative" changes are defined herein as "equivalent" in terms of this application.

Conservative amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as constituting conservatively related groups, respectively.

In making such changes, the hydropathic index of amino acids also may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with biological properties of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Numerous scientific publications have been devoted to the prediction of secondary structure, and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101. In the instant situation, it should be even easier to predict which substitutions will be tolerated given that the primary (and predicted secondary) structures for numerous other adenylyl cyclases are known.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

TABLE 2

| Amino Acid | Hydropathic Index |
| --- | --- |
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

TABLE 3

| Amino Acid | Hydrophilic Index |
| --- | --- |
| arginine | +3.0 |
| lysine | +3.0 |
| aspartate | +3.0 ± 1 |
| glutamate | +3.0 ± 1 |
| serine | +0.3 |
| asparagine | +0.2 |
| glutamine | +0.2 |
| glycine | 0 |
| threonine | −0.4 |
| alanine | −0.5 |
| histidine | −0.5 |
| proline | −0.5 ± 1 |

TABLE 3-continued

| Amino Acid | Hydrophilic Index |
|---|---|
| cysteine | −1.0 |
| methionine | −1.3 |
| valine | −1.5 |
| leucine | −1.8 |
| isoleucine | −1.8 |
| tyrosine | −2.3 |
| phenylalanine | −2.5 |
| tryptophan | −3.4 |

Nucleic acid sequences of the present invention also may be varied from the exemplified sequences of SEQ ID NO:17 or SEQ ID NO:1, 3, 5, 7, 9, 11, 13 or SEQ ID NO:15. Due to the degeneracy of the genetic code, multiple codons can encode a single amino acid. Thus, different nucleic acids may encode the same polypeptide. By reference to the following chart, any codon may be substituted for a corresponding codon:

TABLE 4

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For convenience in cloning, it also may be desirable to alter the nucleic acid sequence to create or delete restriction enzyme sites. In some instances, this may alter the amino acid sequence of the resulting protein product. It is expected that these alterations will be tolerated without the loss of function given their presence at the ends of the catalytic domains. Though some changes conceivably could impair function, these can readily be determined by screening in recombinant hosts, as described below.

In other embodiments it is desired that the $C_1$ and $C_2$ domains of mammalian adenylyl cyclases are separately expressed and reconstituted into a simple mixture. The inventors have demonstrated that it is possible to simply admix separately synthesized cytosolic domains $C_1$ and $C_2$ of adenylyl cyclases and retrieve adenylyl cyclase activity when no such activity exists in the cytosolic domains separately. Hence, similarly to the fusion chimeras discussed above it would be a simple matter to admix any of the 64 possible combinations of $C_1$ and $C_2$ regions to determine which provide functional enzyme composition (Table 1).

As with the fusion proteins of the present invention the $C_1$ and $C_2$ complexes, are activated synergistically by $G_{s\alpha}$ and forskolin, and inhibited by G protein βγ subunits and P-site inhibitors, e.g., 2'-deoxy-3'-AMP.

These observations make it clear that there is cooperativity between the $C_{1a}$ and the $C_{2a}$ domains for catalytic activity to occur. Furthermore the inventors have demonstrated that these two domains spontaneously interact with one another to form an active complex. Such a complex may be facilitated by a positive covalent interaction as exemplified by the chimeric compositions of the present invention. Alternatively, a complex between the $C_{1a}$ and $C_{2a}$ may form, in solution, due to non-covalent interactions, for example ionic interactions, between the two domains to yield an active adenylyl cyclase activity. By non-covalent interaction is meant any interaction that allows $C_1$ and a $C_2$ domain of adenylyl cyclase to interact and produce an adenylyly cyclase activity without a chemical bond linking the components of one domain with the components of the other.

2. Expression Vectors

Expression vectors are genetic constructs that encode gene products and sequences necessary for the expression thereof. A typical expression vector is a bacterial plasmid or phage, such as any of the pUC plasmid series, Bluescript™ or other commercially available, multipurpose cloning vehicles. Expression vectors for use in eukaryotic systems also exist and include integrative and non-integrative plasmids as well as viral vectors such as retrovirus, adenovirus, herpesvirus and baculovirus.

One of the universal structural features of expression vectors is the presence of regulatory elements that permit an inserted gene to be expressed when the vector is brought into contact with RNA- and protein-synthetic machinery. Expression vectors also typically have an origin of replication so that the vector can be propagated in the appropriate host system. In addition, most encode (i) a multipurpose cloning site for easy insertion of gene sequences and (ii) a selectable marker so that host cells carrying the vector can be selected from those that do not.

The expression vector also may include particular ribosome binding sites, polyadenylation sites or any other elements necessary for the expression of the DNA in a host cell. These elements, along with the aforementioned regulatory elements, are combined into expression vector constructs by methods well known and routinely practiced in the art such as restriction enzyme digestion followed by DNA ligase directed splicing of the various genetic elements.

The term "regulatory elements" is meant to include promoters. In prokaryotic systems, the promoter region is about 40 base pairs in length, starting about five to eight base pairs upstream of RNA initiation site (designated +1). Within this sequence is a region referred to as the Pribnow box, a six base pair motif centered about the −10 region. The consensus sequence is TATAAT. Another consensus sequence is about −35. This region is important for accurate initiation of transcription.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

Eukaryotic promoters are composed of multiple genetic elements including that group of transcriptional control modules clustered around the initiation site for RNA polymerase II. These discrete functional modules each comprise approximately 7–20 bp of DNA and contain one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional eukaryotic promoter elements regulate the frequency of transcriptional initiation. Typically, these are located in the region 30–110 bp upstream of the start site, although a number of promoters have recently been shown to contain functional elements downstream of the start site as well. The spacing between some elements is flexible, so that promoter function is preserved when elements are inverted or moved relative to one another. Depending on the promoter, it appears that individual elements can function either cooperatively or independently to activate transcription.

Preferred eukaryotic promoters are viral promoters such as the adenovirus major later promoter, SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. The elements are operably linked to a gene, the expression of which is desired. By "operably linked," it is meant that the regulatory element is positioned, relative to a coding sequence, such that expression of that coding sequences is effected by that element.

The promoter further may be characterized as an inducible promoter. An inducible promoter is a promoter which is inactive or exhibits low activity except in the presence of an inducer substance. Some examples of inducible promoters that may possibly be included as a part of the present invention include, but are not limited to, MT II, MMTV (mouse mammary tumor virus), Collagenase, Stromelysin, SV40, Murine MX Gene, α-2-Macroglobulin, MHC Class I Gene H-2kb, HSP70, Proliferin, Tumor Necrosis Factor or Thyroid Stimulating Hormone α Gene. It is understood that any inducible promoter may be used in the practice of the invention and that all such promoters would fall within the spirit and scope of the claimed invention.

The eukaryotic regulatory elements of the present invention also may comprise an enhancer, operably linked to the gene of interest. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar. They have the same general function of activating transcription in the cell and often have overlapping, contiguous and seemingly similar modular organization.

Below is a list of enhancers that can be used in combination with the present constructs:

TABLE 5

| ENHANCER | REFERENCES |
| --- | --- |
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Arigel et al., 1987 |
| Albumin Gene | Pinkert et al., 1987, Tronche et al., 1989, 1990 |
| α-Fetoprotein | Godbout et al., 1988; Campere and Tilghman, 1989 |
| τ-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α1-Antitrypsin | Latimer et al., 1990 |
| H2B (TH2B) Histone | Hwang et al. 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |

TABLE 5-continued

| ENHANCER | REFERENCES |
|---|---|
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al, 1985; Foecking and Hofstetter, 1986 |
| Gibbon Ape Leukema Virus | Holbrook et al., 1987; Quinn et al., 1989 |

3. Host Cells and Expression Systems

Once an expression vector has been generated, it is necessary to provide the transcriptional and translational machinery that will facilitate expression of the gene encoded by the vector. Such expression systems are well known to the skilled practitioner in the art and include bacterial systems such as *E. coli,* yeast systems such as *Pichia pastoris,* the insect system derived from baculovirus and various mammalian expression systems such as COS or CHO cells.

In a preferred embodiment, polypeptides are expressed in *E. coli* systems. A selected adenylyl cyclase gene construct is inserted into an prokaryotic expression vector by standard subcloning techniques and an *E. coli* expression host transformed (Dessauer and Gilman, 1996). Recombinant *E. coli* are grown in any of a number of suitable media, for example LB, to effect the expression of the adenylyl cyclase. After culturing the bacteria for a sufficient period of time, to be optimized by the operator, the cells are collected by centrifugation and washed to remove residual media. In certain embodiments, the polypeptides expressed in this system are fusion proteins containing the $C_1$ and the $C_2$ regions. In other aspects of the present invention, the $C_1$ and the $C_2$ domains are co-expressed within the same host system. In yet another embodiment, the polypeptides are separately expressed in distinct expression hosts and the $C_1$ and $C_2$ polypeptides are isolated and combined after that expression.

Cells are lysed, for example, by disruption in a cell homogenizer, and centrifuged to separate and cell membranes from the soluble cell components. This centrifugation can be performed under conditions whereby inclusion bodies, if present, are selectively enriched by incorporation of sugars such as sucrose into the buffer and centrifugation at a predetermined speed.

Soluble adenylyl cyclase or the components of the adenylyl cyclase complex (the $C_{1a}$ and $C_{2a}$ domains) may be purified from host cells according to standard methodology. See, for example, Harris et al. (1989). For example, cell extracts may be purified by ammonium sulfate precipitation, ion exchange chromatography, sequential size exclusion chromatography, isoelectric focusing, HPLC size exclusion chromatography, ultracentrifugation or ultrafiltration. Alternatively, incorporated sequences tags may serve as immunological binding partners in antibody-based affinity purification protocols, as described herein.

If the recombinant adenylyl cyclase is expressed as inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations less than 500 μg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by assay of enzymatic activity. Following refolding, the protein can then be purified further and separated from the refolding mixture by chromatography on any of several supports including ion exchange resins, gel permeation resins or on a variety of affinity columns. Storage at ultra-low temperatures (e.g., −80° C.) is recommended.

In another embodiment, the expression system is derived from the insect virus baculovirus. The gene encoding the polypeptide can be manipulated by standard techniques in order to facilitate cloning into the baculovirus vector such that it is under the control of the powerful polyhedron promoter. See Ausubel et al., supra. A preferred baculovirus vector is the pBlueBac vector (Invitrogen, Sorrento, Calif.). The vector carrying the gene for the polypeptide is transfected into *Spodoptera frugiperda* (Sf9) cells by standard protocols and the cells are cultured and processed to produce the recombinant antigen. See Summers et al. (1987); U.S. Pat. No. 4,215,051, incorporated herein by reference.

Although baculovirus expression in insect cells is generally a well known technique, one may additionally refer to any one of the various scientific articles that have been published concerning the use of the baculovirus system specifically in the expression of adenylyl cyclase. By way of example only, Tang et al. (1991), Gao & Gilman (1991) and Taussig et al. (1995) are each incorporated herein by reference for the purposes of describing in even more detail the expression of adenylyl cyclase in Sf9 cells.

In embodiments where it is desirable to combine the $C_1$ and $C_2$ peptides in solution it is understood that the domains are admixed in a suitable buffer that allows for adenylyl cyclase activity to be determined. Such assay and buffer conditions are described in the literature and are well within the skill of the ordinary person skilled in the art (Smigel 1986).

4. Screening of Compounds for Effects on Adenylyl Cyclase Activity

It will be useful, for a variety of clinical indications, to identify inhibitors and stimulators of adenylyl cyclase activity. For example, inhibitors are useful in the treatment of cholera, pituitary tumors, heart failure, ischemia and certain endocrine diseases. As persistent stimulation of the β-adrenergic pathway in cardiocytes can lead to cell necrosis, an inhibitor of this pathway downstream of the receptor would be useful in treating patients with heart conditions. Stimulation of adenylyl cyclase could be useful in the treatment of pseudohypoparathyroidism or other endocrine deficiencies.

The soluble adenylyl cyclase compositions of the present invention may advantageously be used to assess the inhibitory or stimulatory effects of drugs on adenylyl cyclase activity.

Purified or crude enzyme, as described above, can be employed in assays in vitro to assess the ability of particular agents to affect adenylyl cyclase activity. Salomon et al. (1974); Tang et al. (1991); Taussig et al. (1994) are also incorporated herein by reference for the purpose of describing adenylyl cyclase assays in even more detail.

In an alternative embodiment it is possible to create positive selection systems that permit the identification of inhibitors and stimulators of adenylyl cyclase activity without the need for purifying soluble adenylyl cyclase. Specifically, by making host cell growth dependent upon the stimulation of adenylyl cyclase, it is possible to simply treat host cells expressing adenylyl cyclase with a putative inhibitor or stimulator and assess the effects by measuring growth of the host. Another kind of positive selection relies on phenotypic changes in the host when adenylyl cyclase is expressed, such as a colorimetric indication.

A host cell was engineered such that it is dependent upon the synthesis of a heterogeneous adenylyl cyclase. The *E. coli* strain Δcya TP2000 lacks adenylyl cyclase activity and, therefore, cannot utilize maltose as a carbon source and cannot grow on minimal essential media (minimal essential media). When transformed with the soluble adenylyl construct of the present invention, along with a G-protein construct for activation of the adenylyl cyclase, the recombinant host regained the ability to utilize maltose and grown on MEM.

Inhibitors of adenylyl cyclase are readily identified by incubation with the recombinant host described above. When a substance inhibits adenylyl cyclase, the growth of the host will be reduced when compared to that of a control culture not treated with the substance. Similarly, the ability to utilize maltose is measured by growth on McConkey agar; a positive result is indicated by red coloration of adenylyl cyclase$^+$ colonies. Where substance inhibits adenylyl cyclase activity, the coloration will be reduced or eliminated.

Stimulators of adenylyl cyclase also can be readily identified using the same recombinant strain identified above. By looking for increases in growth on MEM or increases in intensity of coloration on McConkey agar, when compared to untreated control cultures, increased adenylyl cyclase activity is identified. The rapidity of growth and coloration also is an indicator of stimulation.

It will, of course, be recognized that the particular benefits of the screening assays of the present invention may lie in the identification of candidate substances as a starting point for developing a therapeutic product, and that further modification of the substances identified may be desired. For example, in order to achieve optimal, or improved, stimulation or inhibition, or to reduce any toxicity, or such like.

5. Example

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Construction of Type I Cytoplasmic Domain $C_{1\alpha}$

To produce DNA for expression of $IC_1$, restriction enzyme sites for NcoI and NotI were introduced at nucleotide 704 (amino acid residue 237 of type I adenylyl cyclase) and nucleotide 1453 (amino acid residue 484 of type I adenylyl cyclase), respectively, and an internal NcoI site was eliminated by two rounds of mutagenesis using M13-mp18-$C_1$ as the template (Kunkel et al., 1987). The 0.7 kB NcoI-EcoRI fragment was cloned into the same sites of pTrcI-lisA (prokaryotic expression vector from Invitrogen, San Diego, Calif.), resulting in pTrc-Is$C_1$. A termination site was introduced by adding phosphorylated linkers (5'-GGCCGCTCACCATCACCATCACCATTAGG (SEQ ID NO:22) and 5'-AATTCCTAATGGTGATGGTGATGGT GAGA (SEQ ID NO:23)) to pTro-Is$C_1$ that had been digested with NotI and EcoRI; the resulting plasmid was used for expression of $IC_1$.

EXAMPLE 2

Construction of Type II Cytoplasmic Domain $C_{2\alpha}$

To produce DNA for expression of $IIC_2$, a 0.9 kB SspI-KpnI fragment was isolated from pSK-rACII (pBluescript with a cDNA insert that encodes type II adenylyl cyclase). This fragment was ligated with phosphorylated linkers (5'-GATCCATCATGAGACAGAGTGAAT (SEQ ID NO:24) and 5'-ATTCACTCTGTCTCATGATC(SEQ ID NO:25)) and pUC18 that had been digested with BamHI and KpnI, resulting in pUC-IIC$_2$. The 0.9 kB BspHI-EcoRI fragment from pUC-IIC$_2$ was transferred to pTrc-HisA that had been digested with NcoI and EcoRI for expression of IIC$_2$ (residues 821 to 1090 of type II adenylyl cyclase).

EXAMPLE 3

Construction of Covalent Chimeras of C$_{1\alpha}$ and C$_{2\alpha}$

To link IC$_1$ and IIC$_2$, the 0.9 kB BspHI-EcoRI fragment from pUC-IIC$_2$ was ligated with phosphorylated linkers (5'-GGCCGCTGGAGG (SEQ ID NO:26) and 5'-GATGCCTCCAGC (SEQ ID NO:27)) and pTrc-IaC$_1$, that had been digested with NotI and EcoRI. One, three or five sets of linkers were incorporated, resulting in pTrc-IC$_1$IIC$_2$-L$_1$, pTrc-IC$_1$IIC$_2$-L$_3$, and pTrc-IC$_1$IIC$_2$-L$_5$, respectively. A small deletion (56 base pairs) at the sequence encoding the amino terminus of IC$_1$IIC$_2$ (right after the NcoI site) occurred during subcloning. The site of initiation of IC$_1$IIC$_2$-L$_3$ is thus residue 271. To express G$_{s\alpha}$, a 1.3-kB NcoI (blunted) to HinDIII fragment encoding either G$_{s\alpha-1}$ or the Gln$^{227}$-Leu mutant of G$_{s\alpha-1}$ was ligated with the 4.5 kB NcoI (blunted) to EcoRI fragment from pBB131 (Knoll and Gordon, 1993).

Figure 1B:
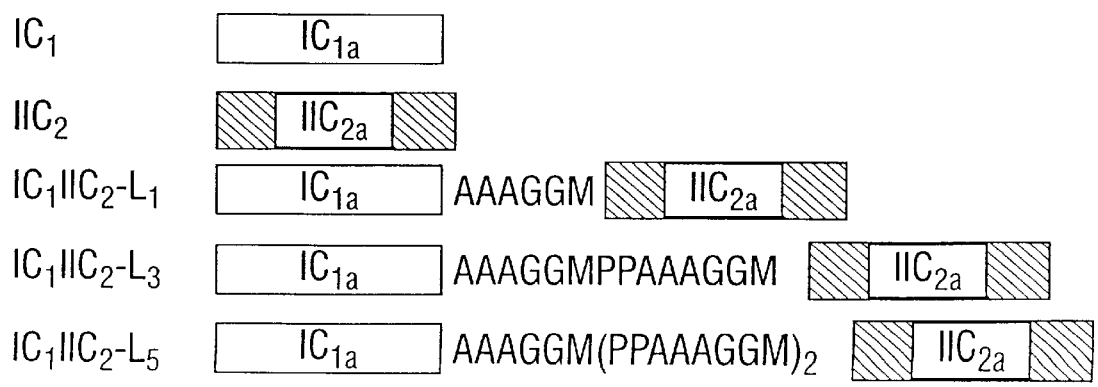

Concurrent expression of the NH$_2$-terminal half of type I adenylyl cyclase and the carboxy-terminal half of type II adenylyl cyclase results in the formation of a noncovalent chimera that remains sensitive to both G$_\alpha$ and forskolin, despite extremely low basal activity. The inventors have thus ligated cDNA's that encode C$_{1a}$ from type I adenylyl cyclase and C$_{2a}$ from type II adenylyl cyclase with short linkers between them, resulting in constructs designated IC$_1$IIC$_2$-L$_1$, IC$_1$IIC$_2$-L$_3$ and IC$_1$IIC$_2$-L$_5$ (FIG. 1).

EXAMPLE 4

Characteristics and Activity of Covalent Chimeras

E. coli that contained the desired plasmids were grown in LB plus 50 μM carbenicillin to OD$_{600}$=0.3. Isopropyl-β-D-thiogalactopyranoside (100 μM) and chloramphenicol (0.5 μM) were added to induce expression of adenylyl cyclase for 12 hours. Bacteria were then collected by centrifugation at 4° C. and lysed by incubation at 4° C. for 30 min in 20 mM Tris-HCl (pH 8.0), 1 mM EDTA, 2 mM dithiothreitol (DTT) and protease inhibitors with 0.1 mg/ml of lysozyme. The suspension was sonicated briefly (3×20 sec) during incubation. The lysate was centrifuged (4° C.) at 150,000×g for 30 min, and the supernatant was recovered.

To evaluate the capacity of these constructs to encode functional adenylyl cyclases, the inventors tested complementation of the catabolic defect in Escherichia coli Δcya TP2000 which lacks adenylyl cyclase activity (Roy and Danchin, 1982). This deficient bacterial strain cannot utilize maltose as a carbon source; colonies thus fail to turn red on McConkey agar and cannot grow on minimal medium (Perlman and Pastan, 1969). To activate adenylyl cyclase in E. coli, the inventors coexpressed the cyclase constructs with either the wild-type alpha subunit of the G protein (G$_{s\alpha}$) or a mutant G$_{s\alpha}$ (in which Gln$^{227}$ is replaced with Leu; designated G$_\alpha$*) that is deficient in guanosine triphosphatase (GTPase) activity and, thus, is constitutively active (Graziano and Gilman, 1989).

E. coli TP2000 were transformed with two compatible plasmids—one for the expression of G$_{s\alpha}$ and the other for expression of the adenylyl cyclase constructs. Transformants were selected for resistance to carbenicillin and kanamycin and bacteria were cultured on either McConkey or M63 agar containing 0.4% maltose, 50 μM carbenicillin, 50 μM kanamycin and 100 μM isopropyl-β-D-thiogalactopyranoside. Cells were grown at 30° C. for the indicated times. Forskolin (5 μl, 10 mM) was spotted on the plates where indicated (+Fsk) before addition of transformants.

E. coli TP2000 expressing either G$_{s\alpha}$ or G$_{s\alpha}$* remained pale yellow on McConkey agar supplemented with maltose and failed to grow on minimal medium (M63 medium containing arginine and maltose). However, bacteria expressing G$_{s\alpha}$* and any of the three chimeric adenylyl cyclase constructs turned red on McConkey agar and grew on minimal medium. Wild-type E. coli turn red in about one half the time required for the chimeric constructs. Correction of the catabolic defect also was evident when wild-type G$_{s\alpha}$ was expressed with IC$_1$IIC$_2$-L$_3$ or IC$_1$IIC$_2$-L$_5$, but longer times were required. There was evidence of a small amount of cyclic AMP synthesis when construct IIC$_2$ was coexpressed with G$_{s\alpha}$*, but no such effect was seen with IC$_1$. Similar ligation of C$_{1a}$ and C$_{2a}$ from type I adenylyl cyclase failed to produce a functional enzyme by these criteria, however.

The inventors also tested four mutants of G$_{s\alpha}$ that are altered in positions corresponding to the α3-β5 and α4-β6 loops of G$_\alpha$ and G$_{\alpha 1}$ and the α3 helix (Noel et al., 1993; Coleman et al., 1994). These mutants have a reduced ability to activate adenylyl cyclase (Berlot and Bourne, 1992). The cDNA's encoding these proteins also were altered to substitute Cys for Arg$^{201}$. This mutation also inhibits GTPase activity and activated the a subunit. These cDNA's were transferred into an expression vector and tested their ability to activate IC$_1$IIC$_2$-L$_3$ in E. coli. As a control, E. coli Δcya turned red on McConkey agar when transformed with vectors encoding G$_\alpha$Arg$^{201}$→Cys and IC$_1$IIC$_2$-L$_3$. Under the same conditions, G$_{s\alpha}$ with a mutation in the α3 helix failed to show activity, whereas the other three mutants were indistinguishable from the control protein. These results correlate well with those obtained by transient expression of the same proteins in HEK 293 cells.

Figure 2:
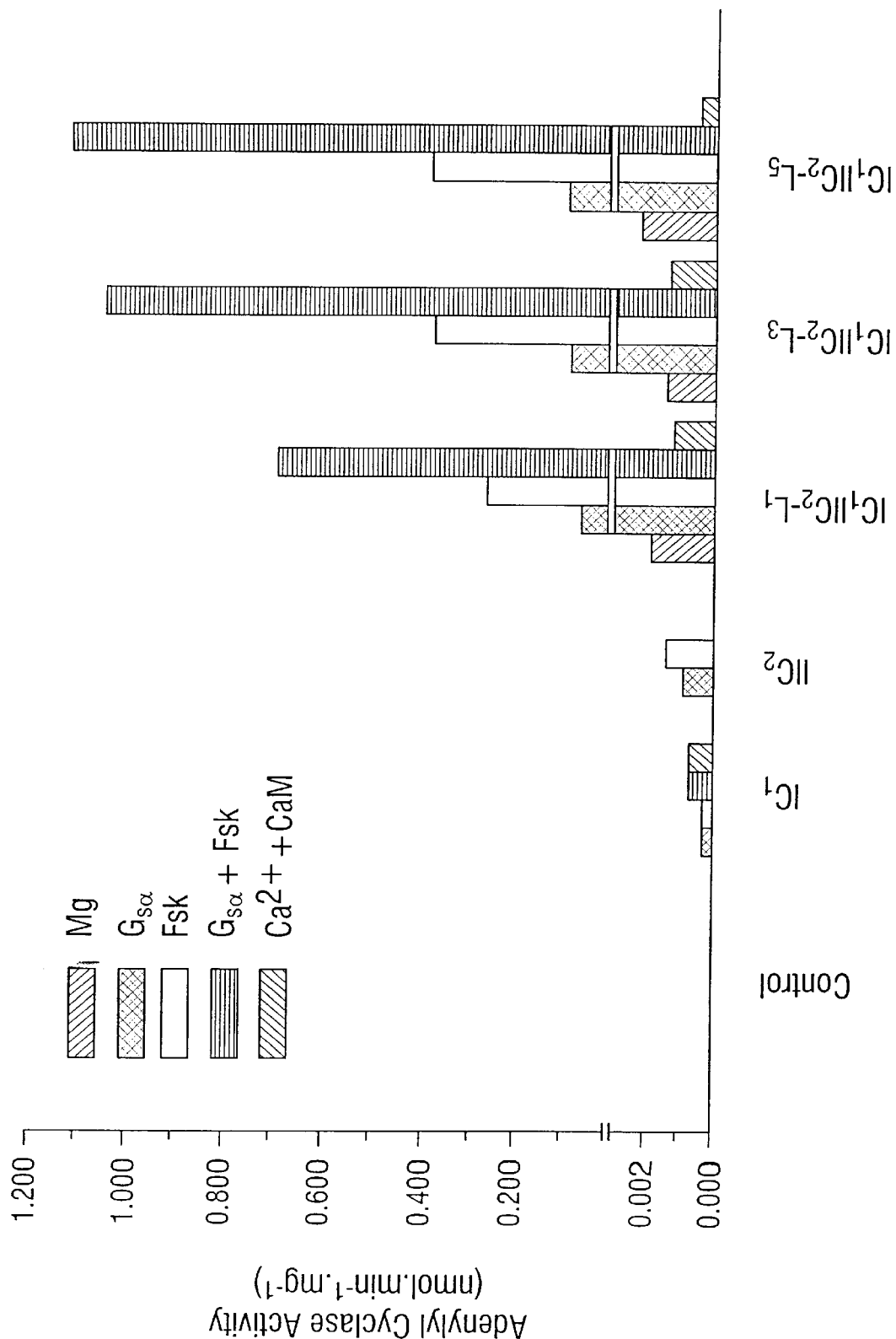
FIG. 2—Enzyme activity of chimeras. Adenylyl cyclase activities of supernatant fractions of lysates (20 µg) from *E. coli* containing the indicated plasmids were assayed with 10 mM $MgCl_2$ at 30° C. for 30 min. Assays also contained 200 nM GTP-γ-S-$G_{s\alpha}$), 100 µM forskolin (Fsk), or 100 µM $CaCl_2$ plus 2 µM calmodulin, as indicated.

The inventors examined adenylyl cyclase activity in vitro in 150,000 g supernatant fractions from E. coli T2000 transformed with the various constructs. The soluble fraction from cells containing a control plasmid had no detectable adenylyl cyclase activity (FIG. 2). By contrast, supernatants from cells expressing IC$_1$IIC$_2$-L$_1$, IC$_1$IIC$_2$-L$_3$, IC$_1$IIC$_2$-L$_5$ displayed basal adenylyl cyclase activity (about 2 pmol/min/mg protein) that was activated by 200 nM G$_{s\alpha}$ bound to GTP-γ-S(50-fold), 100 μM forskolin (150 to 200-fold) or a combination of the two (600-fold). Ca$^{2+}$-calmodulin had no detectable effect on activity, and lysates from cells expressing either IC$_1$ or IIC$_2$ had little adenylyl cyclase activity.

The expected 60 kD protein was detected in appropriate E. coli supernatants with an antiserum to the carboxy-terminus of type II adenylyl cyclase (antiserum C2-1077), although the signal was not strong. Supernatants (60 μg) were alkylated with N-ethylmaleimide, resolved by SDS-polyacrylamide gel electrophoresis (PAGE) (11% gels), transferred to nitrocellulose and stained with affinity purified antiserum C2-1077 directed against the carboxy-terminus of type II adenylyl cyclase. The appropriate 29 kD soluble protein was present in cells expressing IIC$_2$. Also detected were 32 kD, 34 kD and 36 kD proteins in cells expressing $IC_1IIC_2$-$L_1$, $IC_1IIC_2$-$L_3$ and $IC_1IIC_2$-$L_5$, respectively. Other smaller proteins were present in extracts from all cells containing DNA for $IIC_2$. These proteins may arise from proteolysis or initiation of translation from downstream sites.

Figure 3:
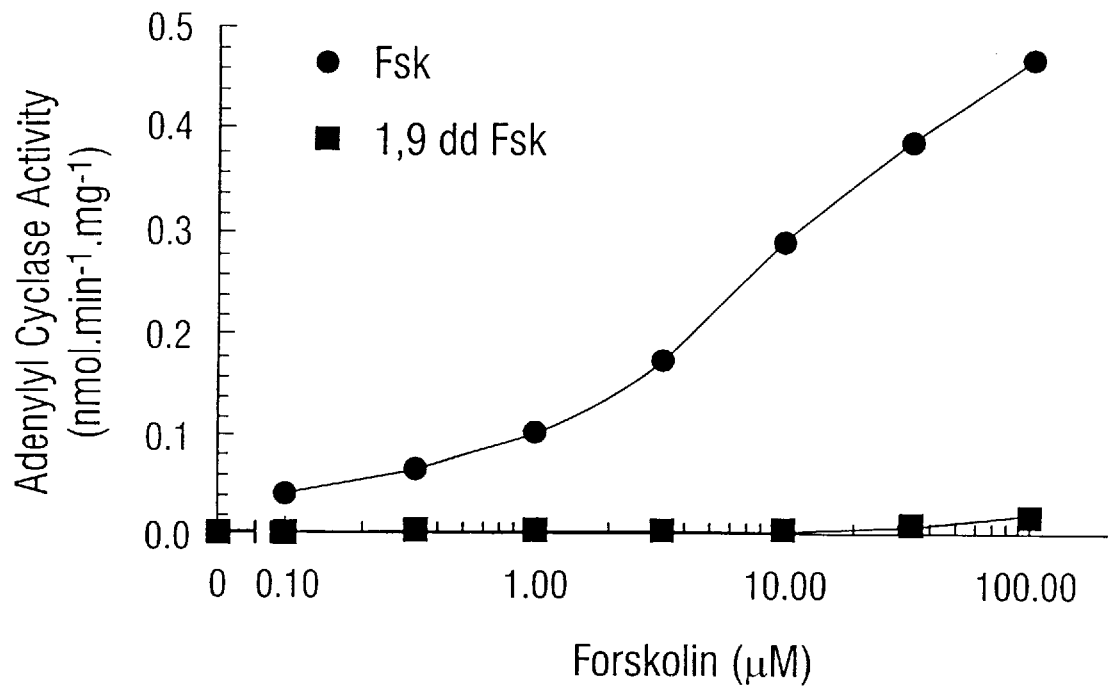
FIG. 3—Enzymatic activity of $IC_1IIC_2$-$L_3$. Activation of soluble adenylyl cyclase by forskolin, but not by 1,9-dideoxyforskolin.
Figure 4:
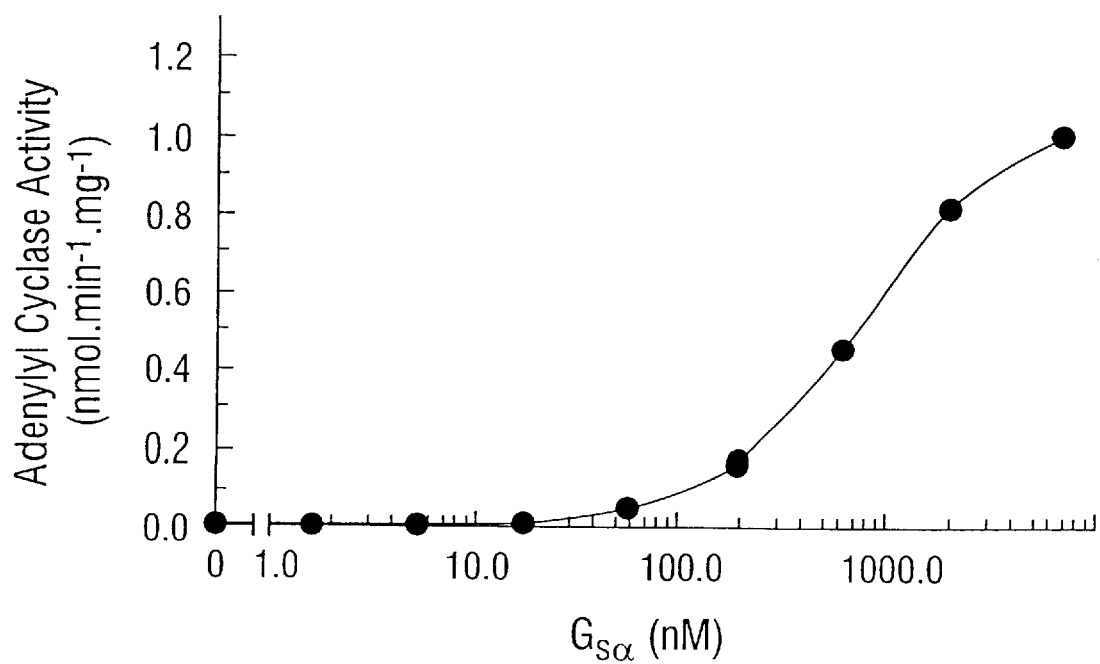
FIG. 4—Activation by GTP-γ-S-$G_{s\alpha}$. Activation of soluble adenylyl cyclase by GTP-γ-S-$G_\alpha$.
Figure 5:
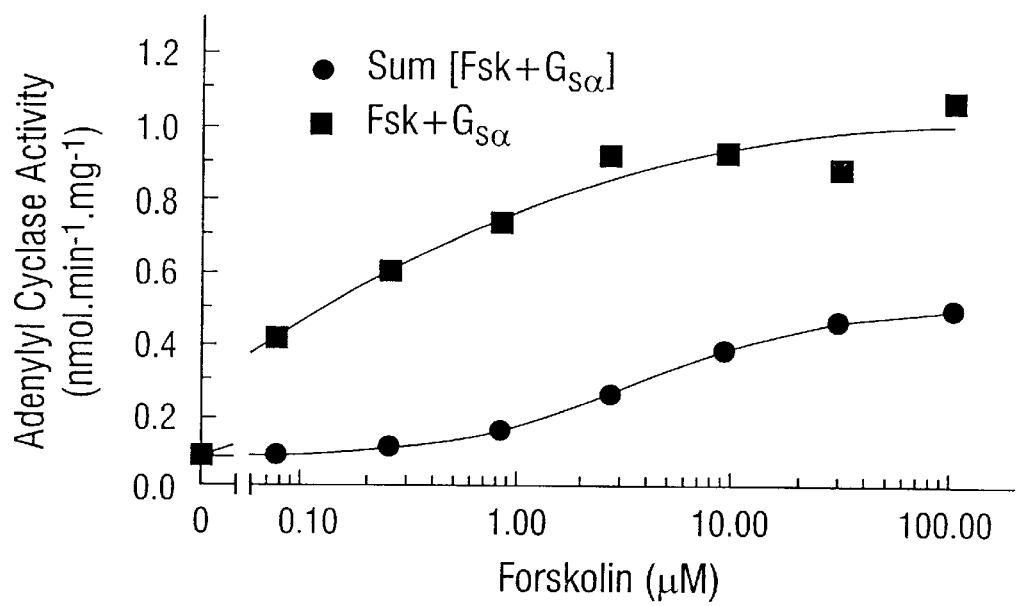
FIG. 5—Synergistic activation by GTP-γ-S-$G_{s\alpha}$ and forskolin. The concentration of GTP-γ-S-$G_{s\alpha}$ was 200 nM (same in FIG. 6 and FIG. 7). Sum [Fsk+$G_{s\alpha}$] is the sum of adenylyl cyclase activities observed in the presence of forskolin or GTP-γ-S-$G_{s\alpha}$ alone. Fsk+$G_{s\alpha}$ is adenylyl cyclase activity observed in the presence of both GTP-γ-S-$G_{s\alpha}$ and forskolin (same in FIG. 6 and FIG. 7).
Figure 6:
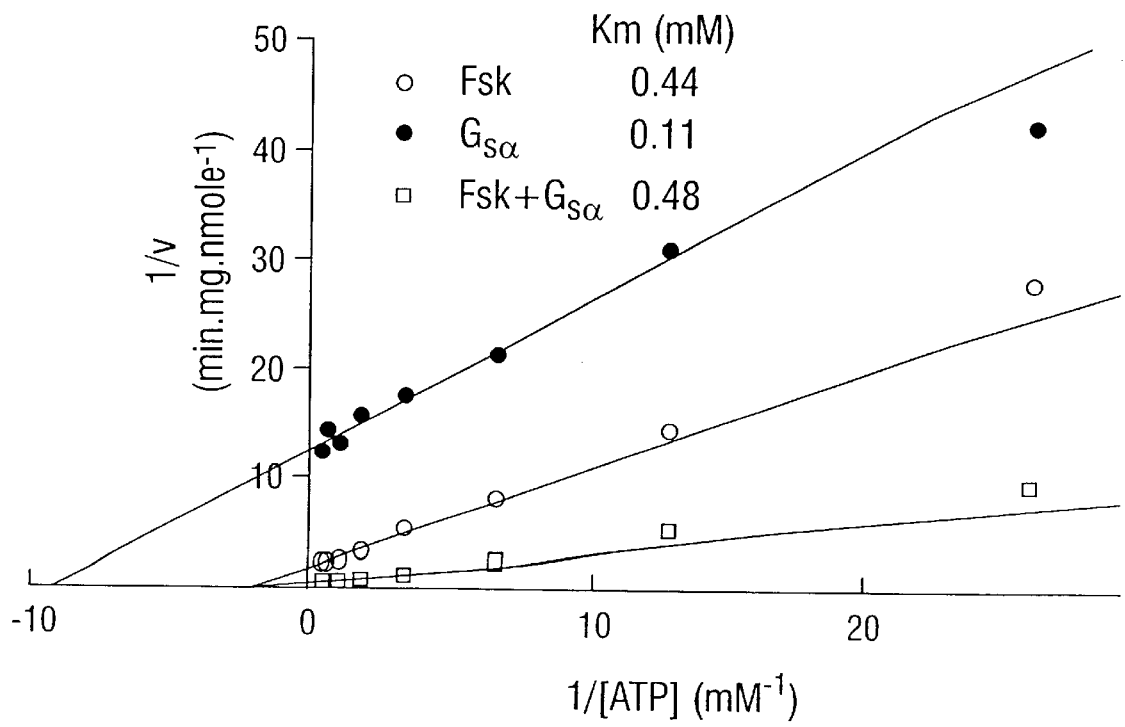
FIG. 6—Determination of $K_{m,ATP}$. The Michaelis constant for ATP forskolin or GTP-γ-S-$G_{s\alpha}$. The concentration of forskolin was 10 µM (same in FIG. 7).

The adenylyl cyclase activity in 150,000 g supernatants from cells expressing $IC_1IIC_2$-$L_3$ was activated by addition of either forskolin (FIG. 3) or GTP-γ-S-$G_\alpha$ (FIG. 4). The median effective concentration ($EC_{50}$) for forskolin was about 7 μM. An analog, 1,9-dideoxyforskolin, which does not activate mammalian adenylyl cyclases (Seamon et al., 1983), also failed to stimulate this enzyme. The $EC_{50}$ for activation of $IC_1IIC_2$-$L_3$ by GTP-γ-S-$G_\alpha$ was about 1 μM, a value 20 to 50 times greater than that observed with type I or type II adenylyl cyclase. However, the maximal stimulatory effect of the G protein α subunit exceeded that of forskolin (FIG. 4). The stimulatory effects of minimally effective concentrations of GTP-γ-S-$G_\alpha$ and forskolin were synergistic (FIG. 5), which also is characteristic of several mammalian adenylyl cyclases (Sutkowski et al., 1994). When $IC_1IIC_2$-$L_3$ was activated with forskolin or GTP-γ-S-$G_\alpha$, values of the Michaelis constants for ATP ($K_{mATP}$) were 0.44 and 0.11 mM, respectively (FIG. 6). Addition of GTP-γ-S-$G_\alpha$ in the presence of forskolin did not change the $K_m$. Synergistic activation of the enzyme was thus not due to alternation of apparent substrate affinity.

Forskolin regulates the functions of a number of intrinsic membrane proteins including adenylyl cyclases (Seamon and Daly, 1986), glucose transporters (Kashiwagi et al., 1983; Joost et al., 1988), voltage-gated potassium channels (Hoshi et al., 1988), nicotinic cholinergic receptors (Wagoneer and Pallotta, 1988), a GABA receptor (Heuschneider and Schwartz, 1989) and P glycoproteins (Wadler and Wiernik, 1988; Morris et al., 1991). These proteins share no obvious amino acid sequence homology. However, all do have one or more hydrophobic domains predicted to include four or six transmembrane helices, and forskolin is highly lipophilic. Attempts to map forskolin binding sites have implicated the transmembrane helices or residues immediately adjacent to these domains (Wadzinski et al., 1990; Morris et al., 1994). It thus was surprising to detect activation of the $IC_1IIC_2$ constructs by forskolin. Perhaps the interaction of forskolin with adenylyl cyclase is different from that with other proteins. Although forskolin activates adenylyl cyclases, it inhibits or blocks the pore conductivity of the other forskolin-regulated proteins.

Figure 7A:
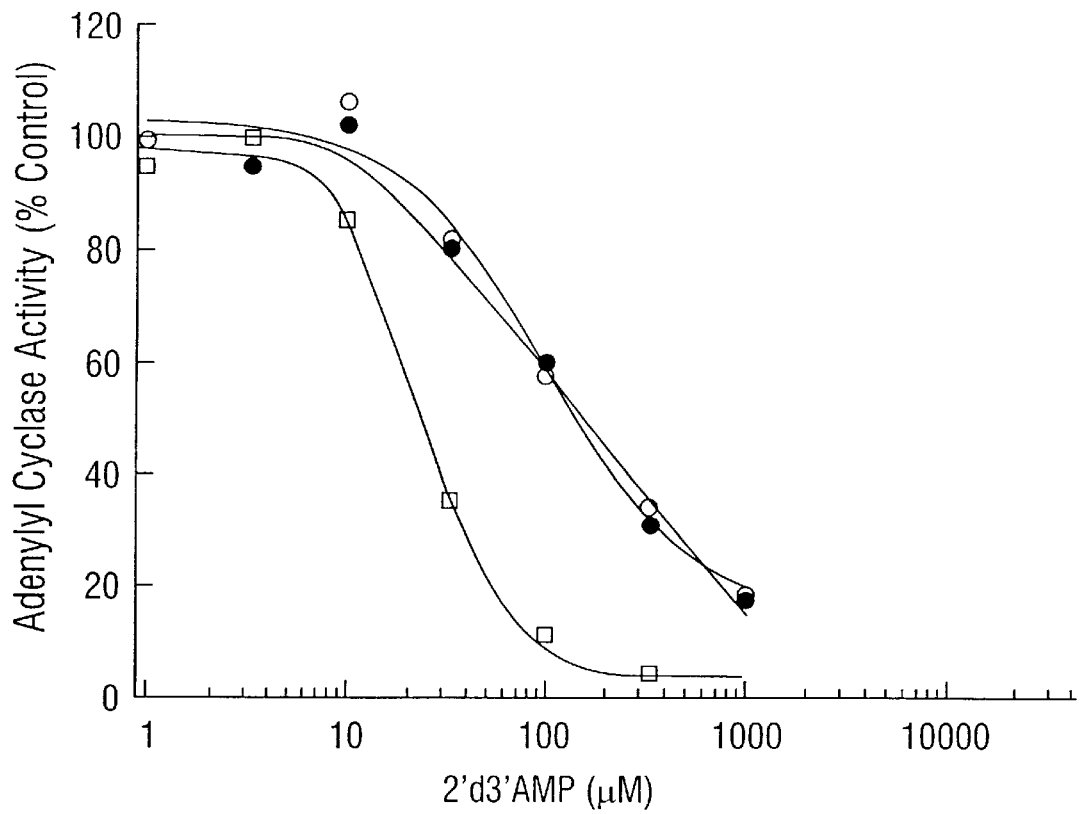
FIG. 7A and FIG. 7B—Effect of 2'-deoxy-3'-AMP. The adenylyl cyclase activity of a supernatant fraction (20 µg) from *E. coli* expressing $IC_1IIC_2$-$L_3$ was assayed at 30° C. for 30 min.
Figure 7B:
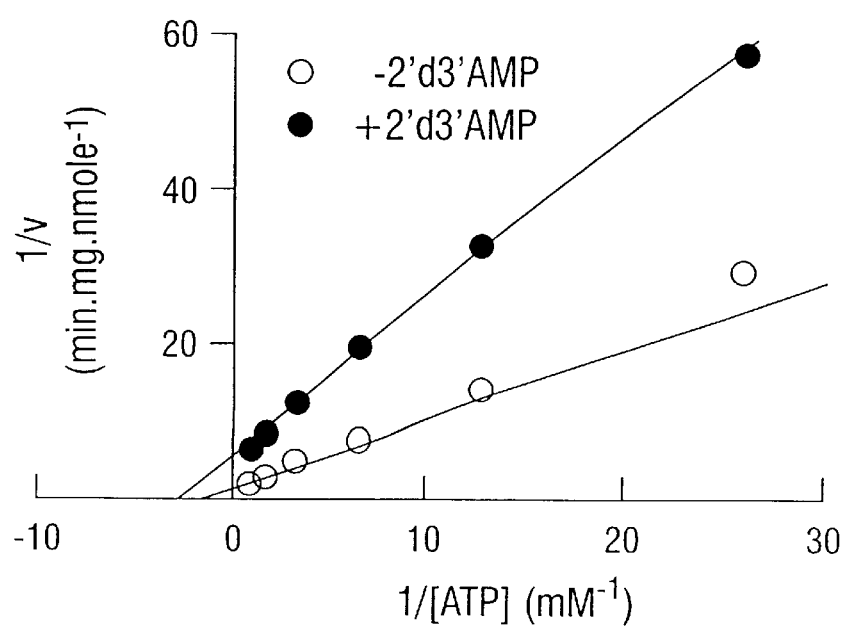

The G protein βγ subunit complex (to 1 μM) inhibited the chimeric adenylyl cyclase while myristylated GTP-γ-S-$G_{\alpha 1}$ (2 μM) had little effect on the basal or stimulated activity of $IC_1IIC_2$-$L_3$. Forskolin-activated $IC_1IIC_2$-$L_3$ was inhibited noncompetitively by 2'-deoxy-3'-AMP (a so-called "P-site" inhibitor) (FIG. 7). The enzyme was most sensitive to inhibition by the P-site analog when it was maximally stimulated by both forskolin and GTP-γ-S-$G_\alpha$. These properties are characteristic of P-site inhibition of mammalian adenylyl cyclases (Johnson and Shoshani, 1990; Florio and Ross, 1983).

Figure 8:
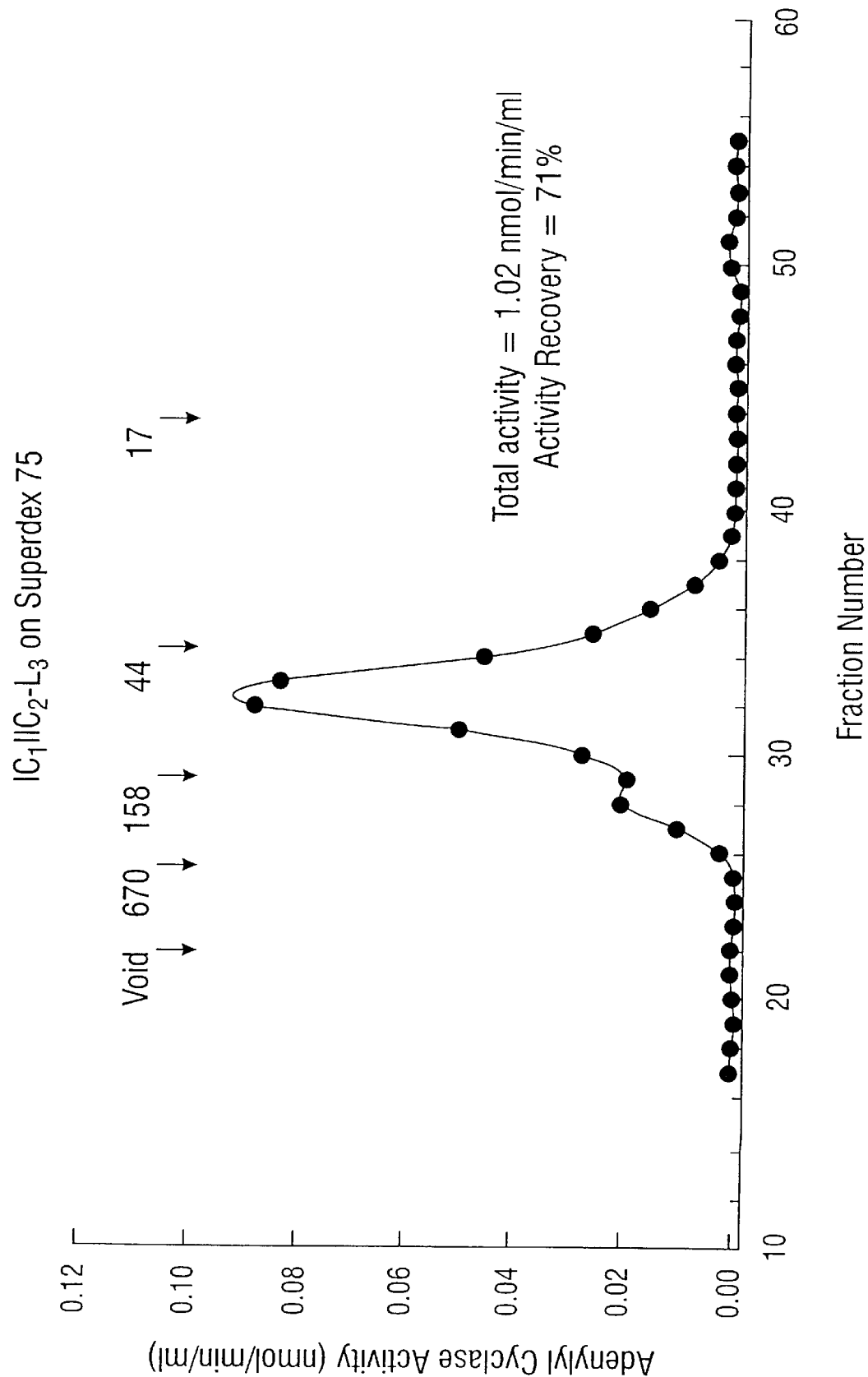
FIG. 8—Superdex 75 gel filtration chromatography of an extract containing $IC_1IIC_2$-$L_3$. Molecular weight markers are thyroglobulin (670 kD), gamma globulin (158 kD), chicken ovalbumin (44 kD) and horse myoglobin (17 kD). Data shown are representative of two studies.

A supernatant containing $IC_1IIC_2$-$L_3$ was subjected to gel filtration through Pharmacia Superdex 75. A major peak of adenylyl cyclase activity consistent with a globular 60 kD protein was observed, along with a minor peak of about twice the size (FIG. 8). The soluble fraction (200 μl) from *E. coli* expressing $IC_1IIC_2$-$L_3$ was applied to a Pharmacia Superdex 75 HR 10/30 gel filtration column that had been equilibrated with 20 mM Tri-HCl (pH 8.0), 1 MM EDTA, 2 mM DTT and 500 mM NaCl. The flow rate was 0.3 ml/min and 0.3 ml fractions were collected. Adenylyl cyclase activity was measured in the presence of 10 mM $MgCl_2$ and 100 μM forskolin. Portions of selected fractions were subjected to SDS-PAGE and immunoblotting. The active enzyme thus appears to migrate as a monomer, although some may be present as dimers. The 60 kD immunoreactive band was present within the major peak of adenylyl cyclase activity, whereas the 27 kD and 34 kD bands were not. Proteolysis was evident in these extracts. Further chromatography of the material shown in FIG. 8 on a Pharmacia mono Q column revealed multiple peaks of activity, and only a fraction of the active enzyme was recognized by antiserum C2-1077 (directed against the COOH-terminus).

The 60 kD protein has been purified to near homogeneity. These preparations are devoid of other immunoreactive bands. It is thus clear that the 60 kD protein is the active species. The turnover number of the purified protein is close to the value for purified type II adenylyl cyclase.

EXAMPLE 5

Adenylyl Cyclase Activity in Mixtures of Cytosolic Domains

Materials and Methods

DNA Constructs, Antibodies, and G Protein Subunits. To create the DNA for expression of the $C_{1a}$ domain of type I adenylyl cyclase ($IC_1$), the construct pTrc(271)$Ic_1IIC_2L3$ (Tang and Gilman, 1995) was digested with BsrBI and ligated with the phosphorylated oligonucleotides 5'-GATCTAGCTAGCTA (SEQ ID NO:28) and 5'-TAGCTAGCTA (SEQ ID NO:29). The DNA was then digested with BspHI and BglII and ligated into pTreH6 (Dessauer and Gilman, 1996) that had been digested with NcoI and BglII. This resulted in a construct with an amino terminal hexa-histidine tag linked to residues 271–484 of type I adenylyl cyclase.

To create the DNA for expression of the $C_2$ domain of type II adenylyl cyclase ($IIC_2$), a polymerase chain reaction was performed on pTrc(271)$IC_1IIC_2L3$ using the primers 5'-ATGAGATCTGGATGCCAAGTTGCTCTGAG (SEQ ID NO:30) and 5'-TGGAGTCATGACACAGAGTGAAT (SEQ ID NO:31); this created an amino terminal BspHI restriction site and a carboxy terminal BglII restriction site. After excision with BspHI and BglII, this fragment was ligated into pQE60 (Qiagen, Chatsworth, Calif.) that had been digested with NcoI and BglII. This created a construct encoding residues 821–1090 of type II adenylyl cyclase with a hexa-histidine tag at the carboxy terminus.

The antibodies utilized in this work have been described (Dessauer and Gilman, 1996). $G_{s\alpha}$ was purified and activated with guanosine 5'-[γ-thio] triphosphate (GTP[γS]) as described (Dessauer and Gilman, 1996).

Expression of Proteins in *E. coli*. The $IC_1$ construct was transformed into *E. coli* strain BL21(DE3), and the cells were grown in the presence of ampicillin (50 μg/ml). The $IIC_2$ construct was transformed into BL21(DE3) cells also harboring the pREP4 plasmid; cells were grown in ampicillin (50 μg/ml). Cultures were grown to $OD_{600}$=0.4 at 30° C.; isopropyl β-D-thiogalactoside (30 μM) was then added and cells were grown at room temperature for 15 h before harvesting and freezing in liquid nitrogen. Cell pellets were resuspended with a Polytron homogenizer in 1/15th the culture volume of lysis buffer (50 mM Tris.HCl, pH 8.0/10 mM 2-mercaptoethanol/50 mM NaCl) containing mixed protcase inhibitors (Dessauer and Gilman, 1996). Cells were lysed by addition of 0.2 mg/ml of lysozyme. After incubation for 30 min At 4° C., DNase was added (0.02 mg/ml plus 5 mM $MgCl_2$). This suspension was centrifuged at 100,000×g for 30 min, and the clarified lysate was collected.

Protein Purification. Clarified lysate from a 10-liter culture was supplemented with NaCl (250 mM final concentration) and loaded onto a 5-ml nickel-nitrilotriacetic acid ($Ni^{2+}$-NTA) column (Qiagen) that had been equilibrated with lysis buffer. The column was washed with 15 volumes of lysis buffer supplemented with 2 mM $MgCl_2$, 400 mM NaCl (final concentration), and 5 mM imidazole; 12 volumes of 50 mM Tris.HCl (pH 8.0), 10 mM 2-mercaptoethanol, 2 mM $MgCl_2$, and 15 mM imidazole; and 8 volumes of 50 mM Tris.HCl (pH 8.0), 10 mM 2-mercaptoethanol, 10 mM NaCl, and 15 mM imidazole. The column was then eluted with 8 volumes of 50 mM Tris-HCl (pH 8.0), 10 mM 2-mercaptoethanol, 10 mM NaCl, 2 mM $MgCl_2$, and 150 mM imidazole.

The $Ni^{2+}$-NTA column eluate containing $IC_1$ was adjusted to 400 mM ammonium sulfate and loaded directly onto a 2-ml phenyl Sepharose column that had been equilibrated in buffer A (50 mM Na-Hepes, pH 8.0/2 mM $MgCl_2$/1 mM EDTA/2 mM dithiothreitol) plus 400 mM $(NH_4)_2SO_4$. The Column was washed with 10 ml of equilibration buffer and 10 ml of buffer A, followed by elution with a linear gradient (20 ml) of 0 to 10 mM 3-[(3-cholamidopropyl) dimethylammonio]-1-propanesulfonate (CHAPS) in buffer A and 20 ml of buffer A containing 10 mM CHAPS. The pooled peak was exchanged into buffer A and concentrated to 0.4 ml ($\approx$1 mg/ml).

The $Ni^{2+}$-NTA column eluate containing $IIC_2$ was loaded directly onto a 8-ml Mono-Q 10/10 column (Pharmacia), equilibrated in buffer A, and washed with 5 volumes of the same buffer. Protein was eluted with a 120-ml linear gradient of NaCl (0–300 mM) in buffer A, followed by a steep gradient to 1 M NaCl. The $IIC_2$ protein represents >90% of the total loaded onto the column and elutes at $\approx$150 mM NaCl. This pooled material was exchanged into buffer A containing 50 mM NaCl and concentrated to 10 mg/ml.

Gel filtration was carried out on a Superdex 200 column (Pharmacia) in 50 mM Na-Hepes (pH 8.0), 2 mM $MgCl_2$, 1 mM EDTA, 2 mM dithiothreitol, and 150 mM NaCl. All samples were loaded onto the column in less than 0.5 ml.

Adenylyl Cyclase Assays. Adenylyl cyclase activity was quantified as described by Smigel (Smigel, 1986). All assays contained 10 mM $MgCl_2$ in a 50-$\mu$l final volume. Incubations were for 10 min at 30° C. unless otherwise indicated.

Results

Figure 9:
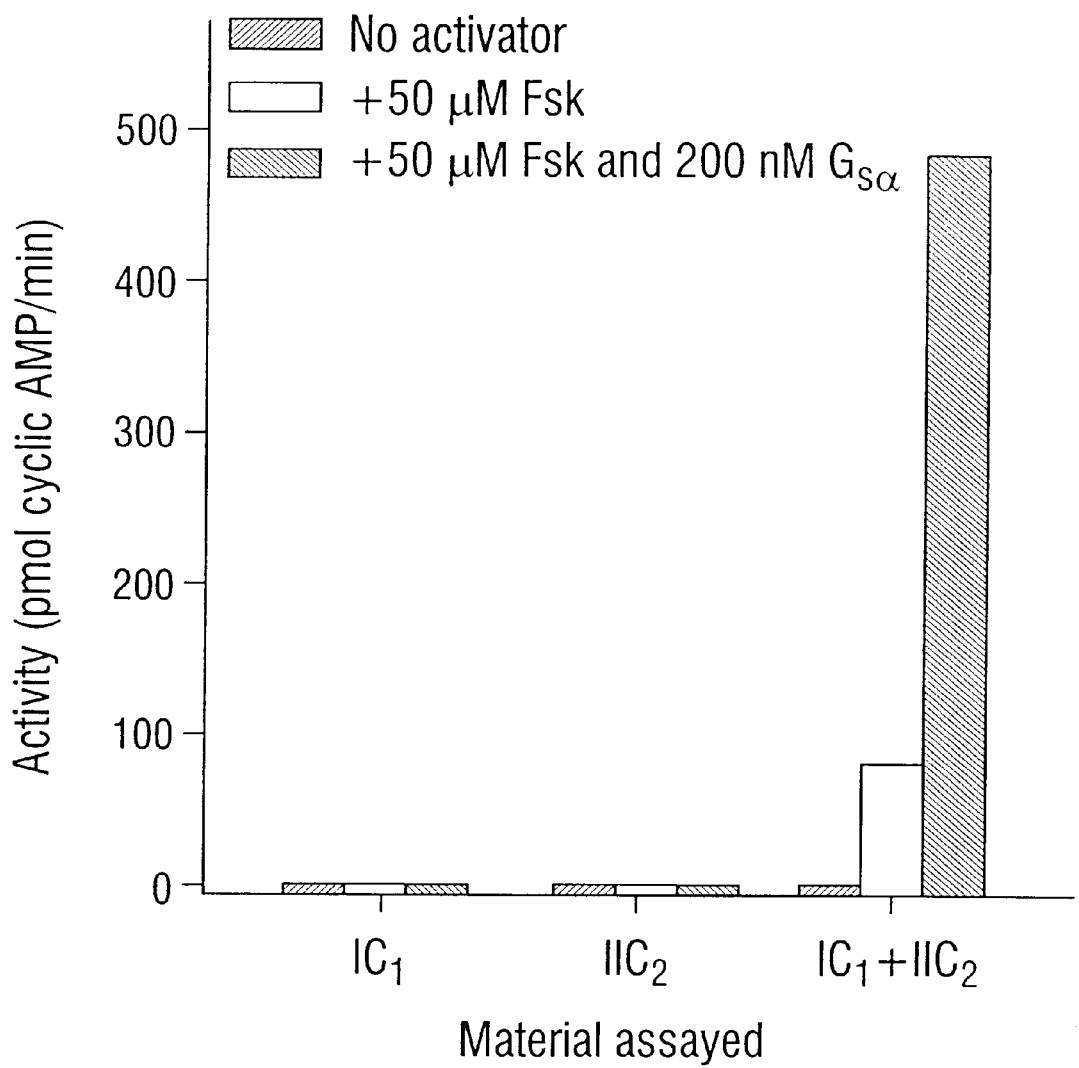
FIG. 9. Simple mixture of the $C_{1A}$ and $C_2$ domains of adenlyl cyclase reconstitutes adenylyl cyclase activity. Bacterial lysates containing either the $IC_1$ or the $IIC_2$ fragments of adenylyl cyclase were assayed as described by themselves (20 µg) or after mixture (10 µg of each) with either no activator, 50 µM FSK, or 50 µM FSK plus 200 nM GTP[γS]-$G_{s\alpha}$. Activities shown as 0 represent less than 1 pmol/min, the limit of detection.
Figure 10A:
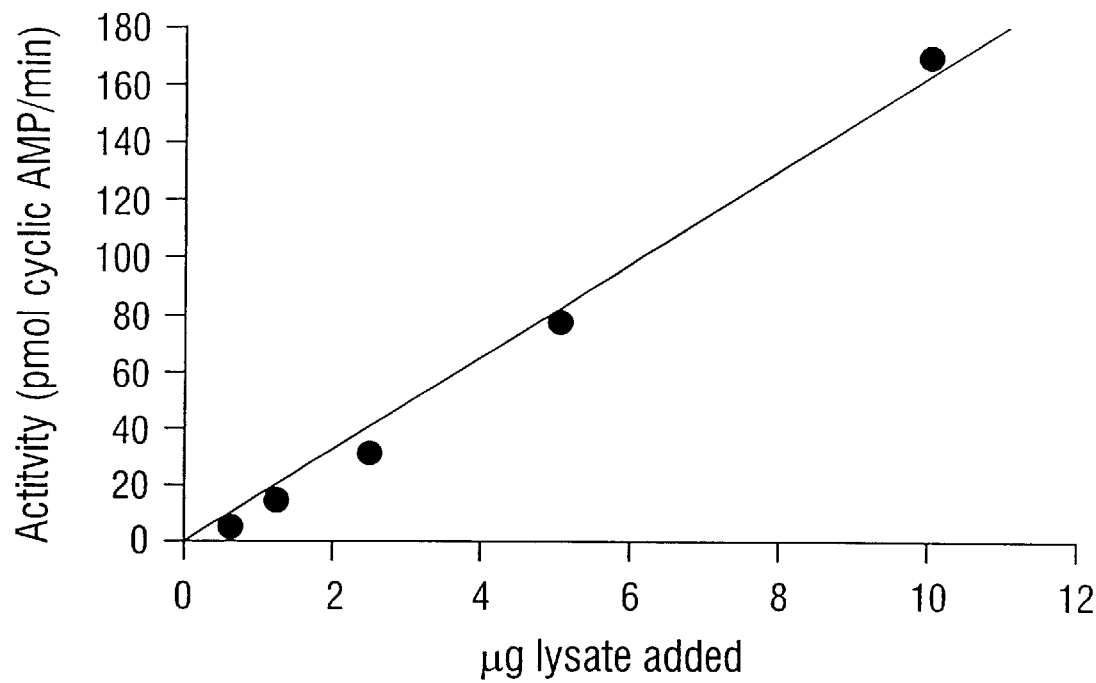
FIG. 10A and FIG. 10B. Definition of a reconstitutive assay for purification of $IC_1$ and $IIC_2$.
Figure 10B:
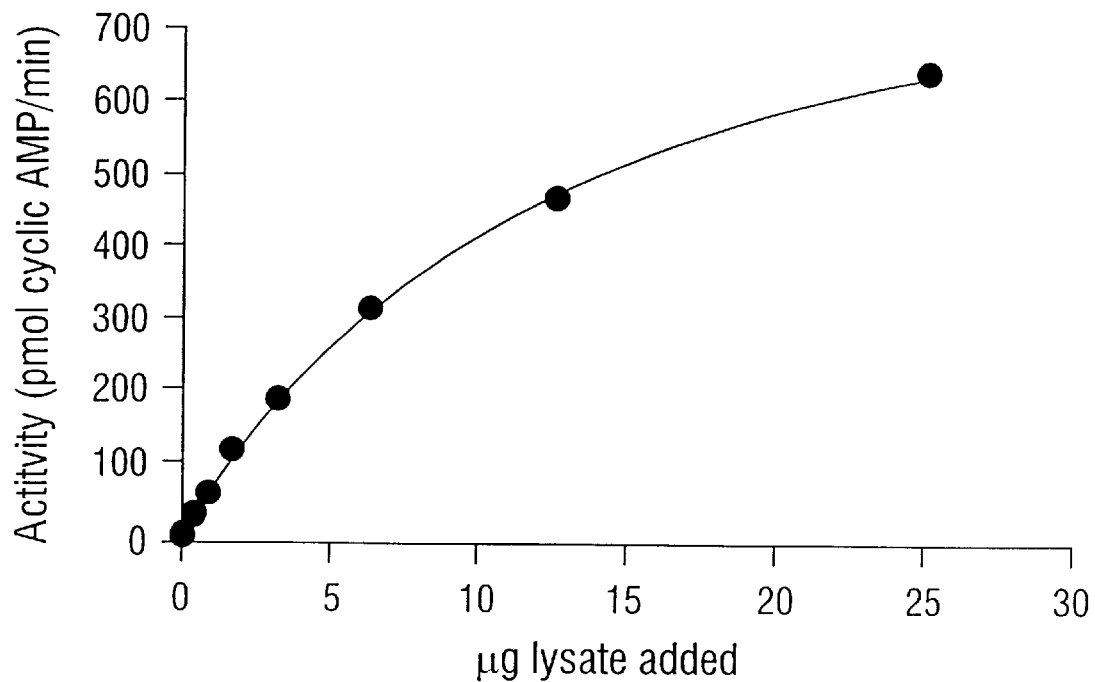

The mixture of two crude bacterial lysates, each containing either the $C_1$ or the $C_2$ domains of type I and type II adenylyl cyclase, respectively, permits observation of GTP [$\gamma$S]]-$G_{s\alpha}$- and FSK-stimulated adenylyl cyclase activity (FIG. 9). Similar results were obtained when the C1 domain of type V adenylyl cyclase was mixed with the C2 domain of type II adenylyl cyclase. There was no detectable activity when $IC_1$, $IIC_2$ or VC1 was assayed alone in the presence or absence of activators. (The same result was obtained after purification of these fragments.) Based on this result, an assay was defined to facilitate purification of each fragment (FIG. 10). Lysates containing the proteins were purified by $Ni^{2+}$-NTA column chromatography as described under materials and methods. A fixed amount of this partially purified material was used as a reagent to assay increasing amounts of the complementary fragment in the presence of 50 $\mu$M FSK. Addition of $IC_1$ to a fixed amount of $IIC_2$ resulted in a roughly linear increase in enzymatic activity (FIG. 10A). Given the smaller amounts of $IC_1$ in these preparations, saturation was observed when increasing amounts of $IIC_2$ were added to the partially purified preparation of $IC_1$ (FIG. 10B). Assays were carried out in the linear ranges of these titrations.

Figure 11A:
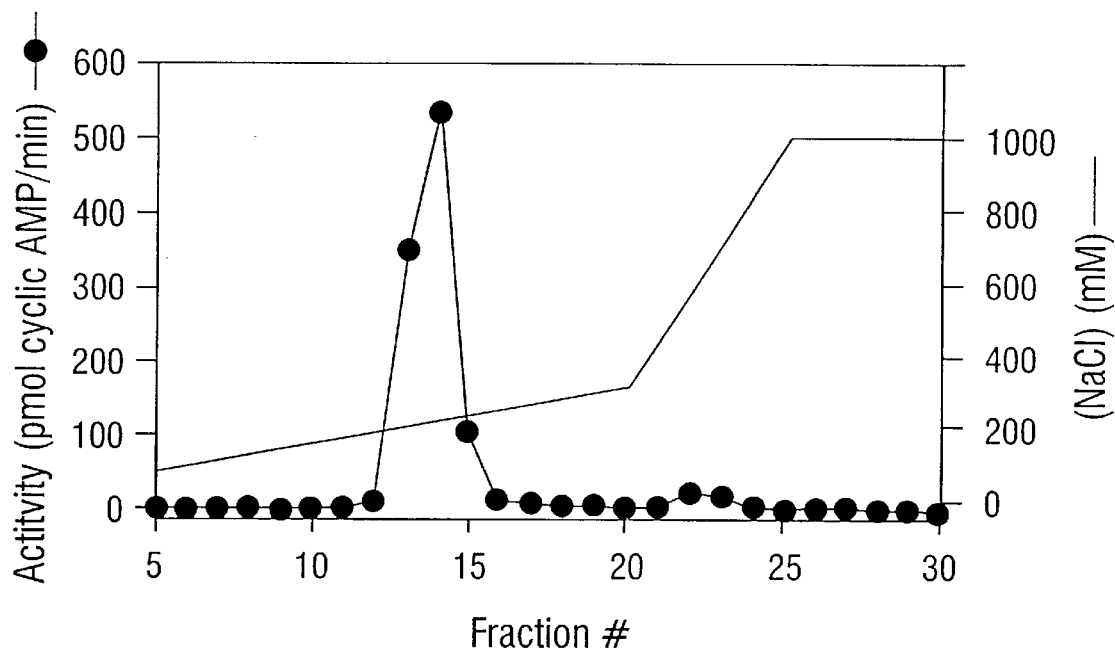
FIG. 11A and FIG. 11B. Purification of $IIC_2$.
Figure 11B:
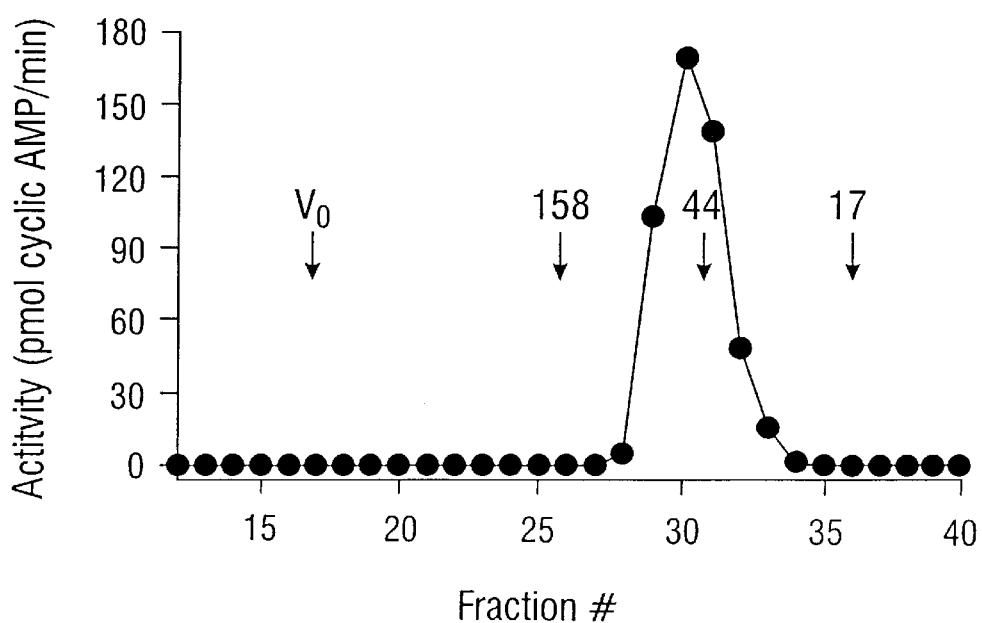

Large amounts (6 mg/liter of culture) of the $IIC_2$ fragment were readily purified to homogeneity by $Ni^{2+}$-NTA and Mono Q column chromatography (FIG. 11 and Table 6). The $IC_1$ and $IIC_2$ were resolved on 11% polyacrylamide gels and stained with Coomassie blue, the material appeared to be homogeneous after SDS/PAGE. Amino acid sequencing revealed that the amino terminus of the protein began at Met-847 of type II adenylyl cyclase, 27 residues downstream from the presumed initiator methionine in the construct. Electron spray mass spectroscopy revealed a single species with a $M_r$ of 28,258, consistent with a protein containing Met-847-Ser-1090 (calculated $M_r$=28,256). Gel filtration of this material showed a single peak of activity with an apparent $M_r$ of $\approx$50,000 (FIG. 11). This behavior may represent dimerization of the fragment. The protein yield from these studies was 0.22 mg for $IC_1$, 57 mg for $IIC_2$ (Table 6). Similar studies with $VC_1$ yielded 10 mg of VC1 protein.

TABLE 6

PURIFICATION OF THE $IC_1$ AND $IIC_2$ FRAGMENTS OF MAMMALIAN ADENYLYL CYCLASE

| Preparation | Fraction | Protein, mg | Total activity, $\mu$mol/min | Specific activity, $\mu$mol/min-mg |
|---|---|---|---|---|
| $IC_1$ | Lysate | 1300 | 7.8 | 0.006 |
|  | $Ni^{2+}$-NTA | 15 | 2.0 | 0.13 |
|  | Phenyl Sepharose | 0.40 | 0.10 | 0.25 |
|  | Gel Filtration | 0.22 | 0.28 | 1.3 |
| $IIC_2$ | Lysate | 1400 | 220 | 0.16 |
|  | $Ni^{2+}$NTA | 63 | 100 | 1.6 |
|  | Mono-Q | 57 | 120 | 2.1 |

Each preparation represents a 10-liter culture. Under the assay conditions defined in FIG. 10, activities were linear with respect to time and protein concentration. However, $IC_1$ and $IIC_2$ were not used at saturating concentrations, as defined in FIG. 13B. Thus, the specific activities for the two preparations shown in this table cannot be compared with each other or to the specific activities for $IC_1$ shown in FIG. 13 and FIG. 14.

Figure 12A:
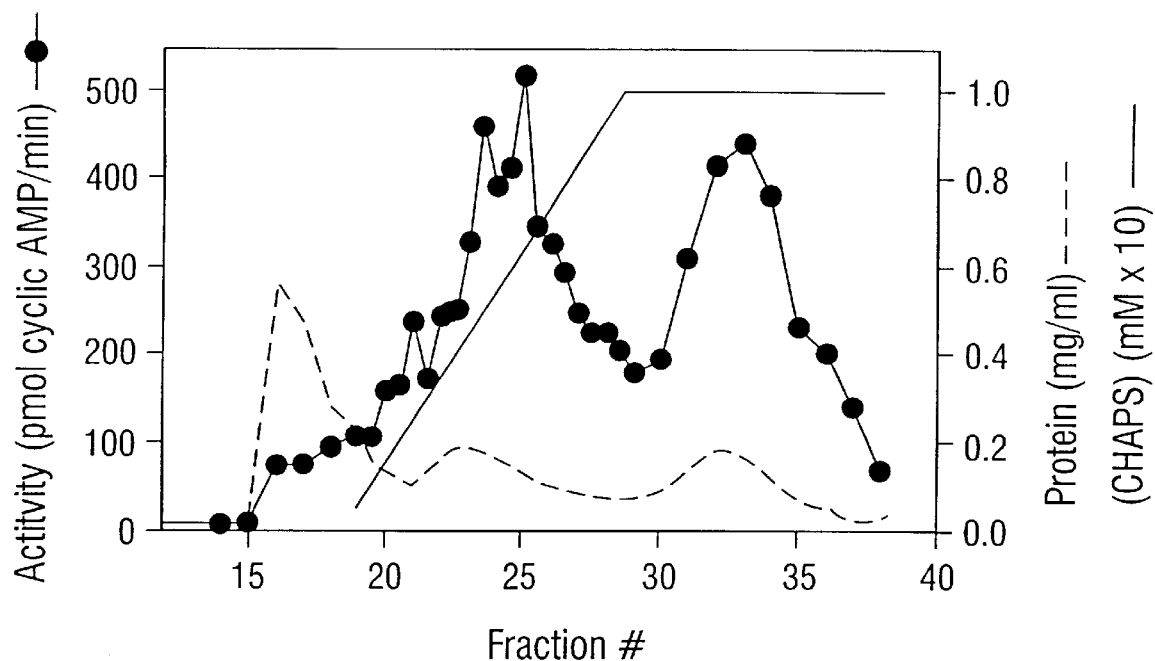
(FIG. 12A) Increasing amounts of lysate containing $IC_1$ were mixed with 1.5 µg of the $Ni^{2+}$-NTA column eluate containing $IIC_2$ and assayed with 50 µM FSK.
Figure 12B:
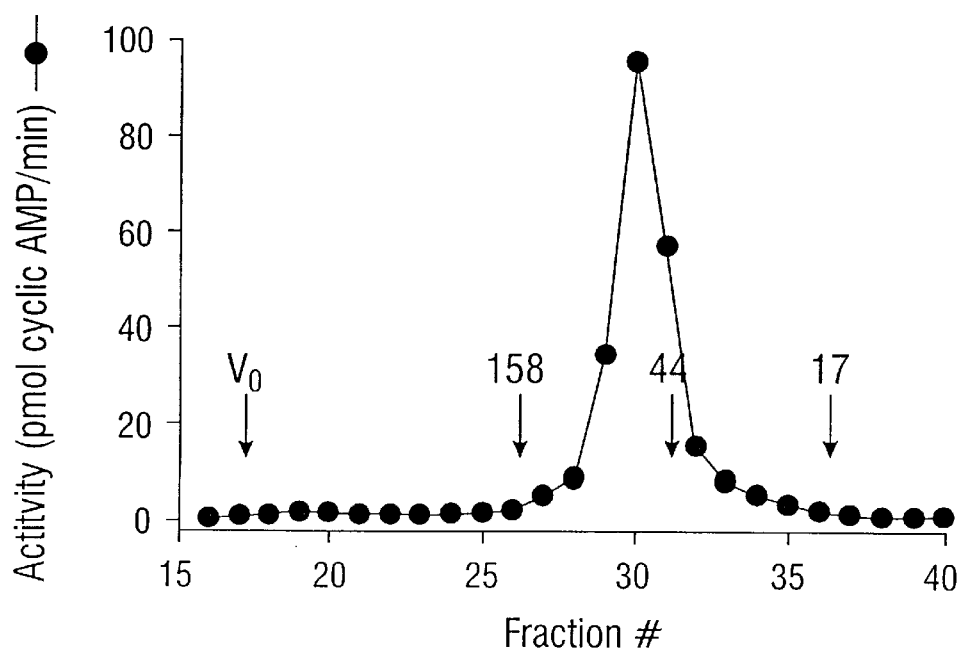

The $IC_1$ fragment accumulated to much lower levels during bacterial culture. It can be purified by a combination of $Ni^{2+}$-NTA, phenyl-Sepharose, and gel filtration chromatography (FIG. 12 and Table 6). Two distinct peaks of activity were eluted from the phenyl-Sepharose column. The first of these was further purified by gel filtration, where it too displayed an apparent $M_r$ of 50,000. The second phenyl-Sepharose peak displayed a similar gel filtration profile but contained more contaminants; this peak was not investigated further.

Figure 13A:
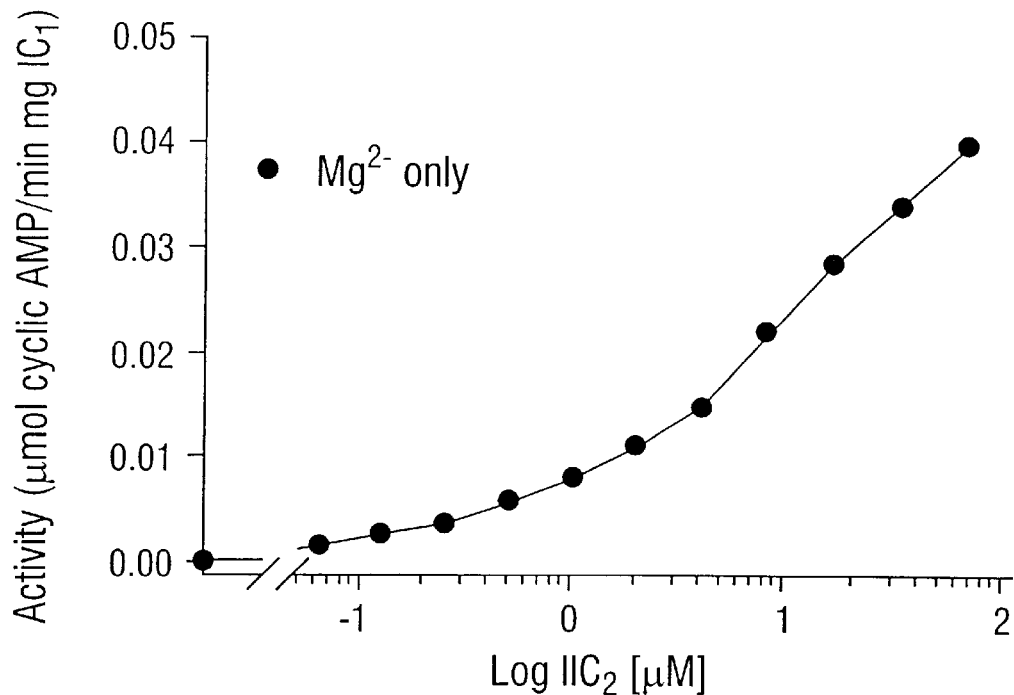
FIG. 13A and FIG. 13B. Interactions of $IC_1$ with $IIC_2$.
Figure 13B:
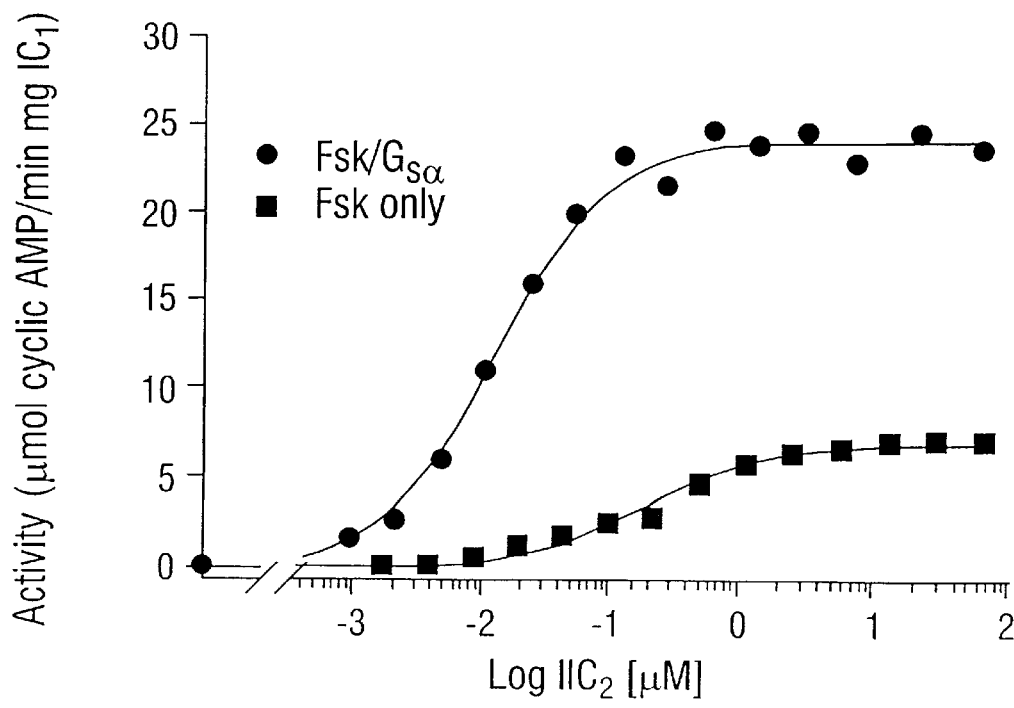

The inventors first examined adenylyl cyclase activity obtained by mixture of $IC_1$ and $IIC_2$ in the absence of any activator (FIG. 13A). Increasing amounts of $IIC_2$ were added to 0.1 $\mu$M $IC_1$. The highest activity observed (expressed per quantity of $IC_1$) was 100-fold lower than that obtained in the presence of 50 $\mu$M FSK and 500-fold lower than that observed with FSK and activated $G_{s\alpha}$ FIG. 13B). It was not possible to maximize activity by increasing the concentration of $IIC_2$ in the absence of activators (FIG. 13A). However, activity was maximized with apparent $EC_{50}$ values for $IIC_2$ of 190 nM and 15 nM when stimulated by FSK or FSK plus activated $G_{s\alpha}$, respectively (FIG. 13B). Thus, the apparent affinity of $IIC_2$ for $IC_1$ was increased substantially by addition of FSK; an even greater shift was observed when activated $G_{s\alpha}$ was also present.

Figure 14A:
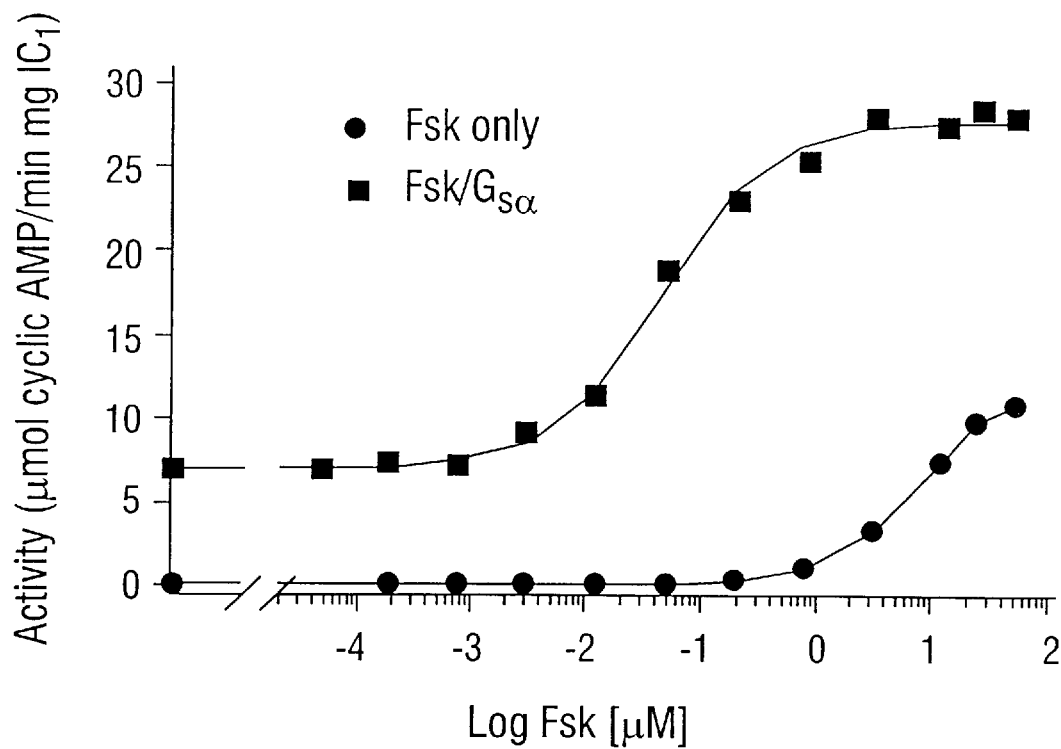
FIG. 14A and FIG. 14B. Interactions between FSK and GTP[γS]-$G_{s\alpha}$.

The inventors also examined the capacity of FSK and $G_{s\alpha}$ to stimulate the adenylyl cyclase activity of the mixed fragments as a function of activator concentration (FIG. 14). In these studies 8 nM $IC_1$ was mixed with 6.6 µM $IIC_2$. This is a saturating concentration of $IIC_2$ in the presence of either FSK or $G_{s\alpha}$ plus FSK. When increasing concentrations of FSK were tested in the presence or absence of 0.5 µM activated $G_{s\alpha}$, maximal activity was increased by $G_{s\alpha}$ and the $EC_{50}$ for FSK was lowered by a factor of 100 (FIG. 14A). When increasing concentrations of activated $G_{s\alpha}$ were examined in the presence or absence of 50 µM FSK, maximal activities were similar under the two conditions. However, the inclusion of FSK shifted the $Ec_{50}$ for activated $G_{s\alpha}$ by more than 100-fold.

Discussion

The inventors have expressed the $IC_1$ and $IIC_2$ domains of mammalian adenylyl cyclase separately and reconstituted $G_{s\alpha}$- and FSK-stimulated adenylyl cyclase activity by their mixture. Neither protein has detectable adenylyl cyclase activity by itself (with or without activators), and the mixture has a very low basal activity in the absence of an activator. However, the activity observed in the presence of FSK and/or activated $G_{s\alpha}$ provides compelling evidence that adenylyl cyclase activity is dependent on the association of the $C_1$ and $C_2$ domains of the protein. The stimulated level of activity observed is comparable to that seen with the native, membrane-bound enzyme. Furthermore, the activation produced by FSK and $G_{s\alpha}$ is synergistic. The inventors thus believe that this system provides a valuable tool for definition of mechanisms of regulation of adenylyl cyclase activity. As a first step toward this goal, the inventors provide the model shown in FIG. 15 for analysis of the data presented above.

It is not known if the individual protein fragments studied here exist as dimers, as suggested by their gel filtration profiles. If true, their affinity for homooligomerization is very high, since the gel filtration pattern is unaltered at very low protein concentrations. The inventors also do not know if membrane-bound adenylyl cyclase or the soluble $IC_1IIC_2$ construct (Neer et al., 1980; Pfeuffer et al., 1985; Tang et al., 1995) is multimeric. However, the specific activity of $IC_1$ used in these studies is constant over a broad range of concentrations (200 pM to 100 µM) when assayed in the presence of saturating concentrations of $IIC_2$ and 50 µM FSK, and the covalent $IC_1IIC_2$ construct similarly has a constant specific activity over a similar range of concentrations when activated with either FSK or FSK plus $G_{s\alpha}$. If the catalytic entity is dependent on the formation of homooligomers, the inventors suggest that such structures are dominant at the protein concentrations used in this study. This justifies consideration of the data presented here in the context of the model shown in FIG. 15.

Figure 15:
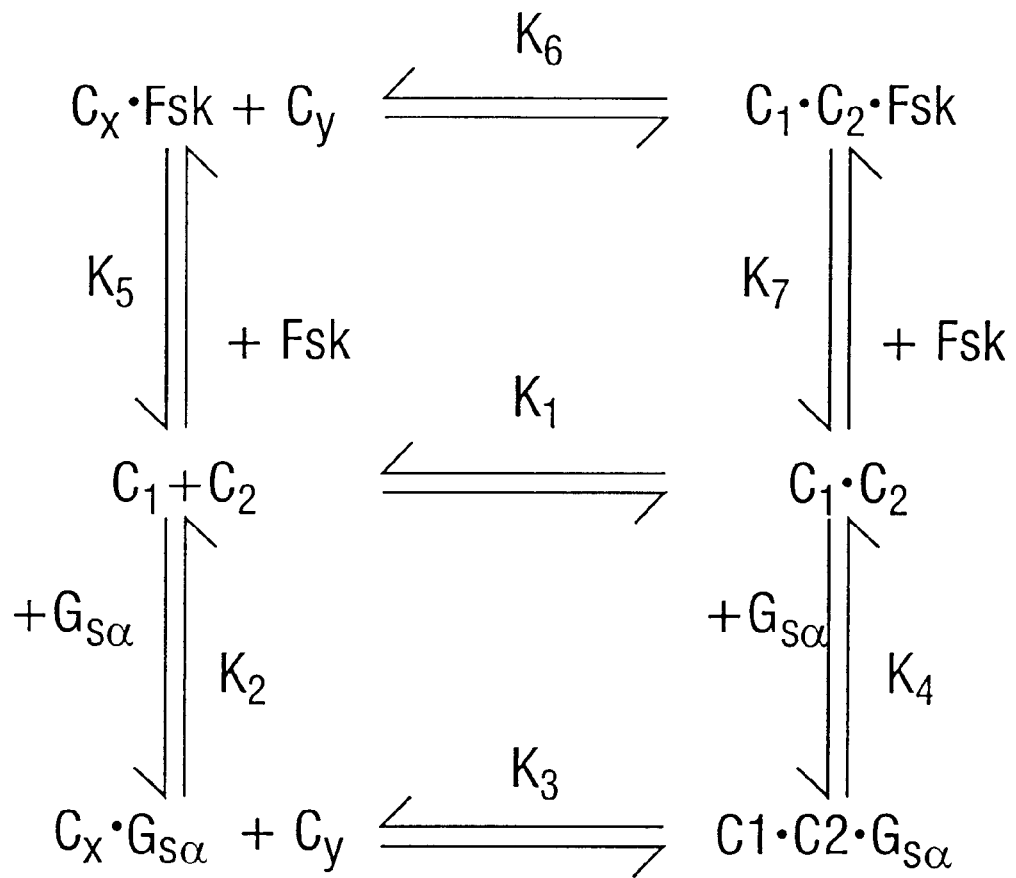
FIG. 15. A simple model for the interactions of $IC_1$, $IIC_2$, $G_{s\alpha}$, and FSK. The two domains of adenylyl cyclase are designated $C_x$ and $C_y$ where their identities are unknown; they are designated $C_1$ and $C_2$ when associated.

The data of FIG. 13A provide an estimate of the lower limit for the affinity of $IIC_2$ for $IC_1$ in the absence of any activator: $K_1>10$ µM (FIG. 15). In the presence of FSK (FIG. 13B), both a higher specific activity and a lower $EC_{50}$ for $IIC_2$ are apparent. The expression for fractional activation of $IC_1$ in the presence of FSK is as follows:

$$Act_{fr} = \frac{[IIc_2]}{\frac{K_1 K_7}{[Fsk]} + [IIC_2]\left(\frac{K_7}{[Fsk]} + 1\right)} \quad [1]$$

This neglects the activity due to unregulated complexes of $IC_1$ and $IIC_2$, which is insignificant. This derivation also relies on the assumption that $K_5$ is relatively large—i.e., that most of the $IIC_2$ in the assay is free and not bound to FSK.

At FSK concentrations that are high relative to $K_7$, Eq. 1 approximates a normal binding isotherm, where the $EC_{50}$ is equal to $K_1K_7/[FSK]$. From the $EC_{50}$ of 190 nM (FIG. 13B), $K_7=1$ µM. A similar analysis of the FSK activation curve (FIG. 14A) also provides an estimate for $K_7$:

$$Act_{fr} = \frac{[Fsk]}{K_7\left(\frac{K_1}{[IIC_2]} + 1\right) + [Fsk]} \quad [2]$$

Eq. 2 yields a value for $K_7$ of 3.7 µM, in reasonable agreement with the value obtained from Eq. 1 (1 µM).

An identical analysis can be done for stimulation of activity by $G_{s\alpha}$ by using Eq. 3 and the $EC_{50}$ for activated $G_{s\alpha}$ from FIG. 14A.

$$Act_{fr} = \frac{[G_{s\alpha}]}{K_4\left(\frac{K_1}{[IIC_2]} + 1\right) + [G_{s\alpha}]} \quad [3]$$

This analysis yields a value for $K_4$ of 0.4 µM. Similarly, the value of $K_2$ must be sufficiently high to permit this analysis to be meaningful. Attempts are underway to isolate the interactions of the individual fragments with these activators to determine the values of $K_2$ and $K_5$.

Figure 14B:
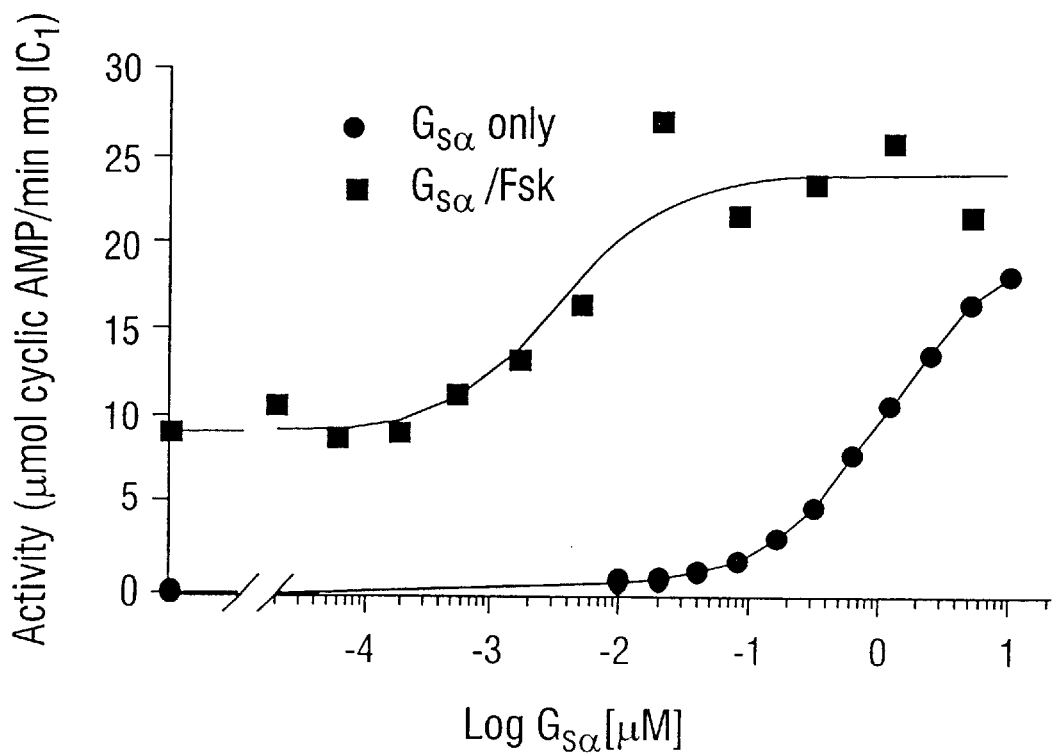

Qualitatively, it is clear that there is positive cooperativity among the four molecules involved in the formation of active complexes. The inclusion of FSK when titrating $IIC_2$ shifts the $EC_{50}$ for $IIC_2$ from a value of $\geq 10$ µM to 190 nM. Thus, this activator facilitates association of the two adenylyl cyclase fragments ($K_6$ is less than $K_1$). The inclusion of activated $G_{s\alpha}$ shifts this $EC_{50}$ to an even lower value, indicating that $G_{s\alpha}$ and FSK both shift the equilibrium toward association of $IC_1$ and $IIC_2$. The binding of these two activators is also positively cooperative with respect to each other. Thus, the presence of activated $G_{s\alpha}$ during the FSK titration lowers the $EC_{50}$ for FSK dramatically (FIG. 14A), just as the presence of FSK lowers the $EC_{50}$ for $G_{s\alpha}$ (FIG. 14B). These results are similar to those obtained with the covalently linked $IC_1IIC_2$ construct (Dessauer and Gilman, 1996) and the type II enzyme (Feinstein et al., 1991). The inventors conclude that the presence of either activator in the active complex acts to enhance association of the other activator, as well as facilitating the interaction of the $C_1$ and $C_2$ domains of adenylyl cyclase.

This model can be confirmed and described explicitly for a single activator if the affinity of the activator for the individual protein domains ($K_2$ and $K_5$) can be determined. It is not known which of the two domains, if either, binds FSK or $G_{s\alpha}$ to any significant extent. However, the existence of this system will permit analysis of such interactions.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

Bakalyar and Reed, "Identification of a Specialized Adenylyl Cyclase that May Mediate Odorant Detection," *Science*, 250:1403–1406, December 1990.

Berlot and Boume, *Cell*, 68:911, 1992.

Cali et al., "Type VIII Adenylyl Cyclase," *The Journal of Biological Chemistry*, 269(16):12190–12195, April 1994.

Chou and Fasman, "Prediction of Protein Conformation," *Biochemistry*, 13(2):222–245, 1974a.

Chou and Fasman, "Conformational Parameters for Amino Acids in Helical, β-Sheet, and Random Boil Regions Calculated from Proteins," *Biochemistry*, 13(2):211–222, 1974b.

Chou and Fasman, "Prediction of the Sevondary Structure of Proteins from Their Amino Acid Sequence," *Adv. Enzymol. Relat. Areas Mol. Biol.*, 47:45–148, 1978a.

Chou and Fasman, "Empirical Predictions of Protein Conformation," *Ann. Rev. Biochem.*, 47:251–276, 1978b.

Chou and Fasman, "Prediction of β-Turns," *Biophys. J.*, 26:367–384, 1979.

Coleman et al., *Science*, 265:1405, 1994.

Dessauer and Gilman, *J. Biol. Chem.*, 271 (28):16967–74, 1996.

Feinstein et al., "Molecular Cloning and Characterization of a $Ca^{2+}$/Calmodulin-insensitive Adenylyl Cyclase from Rat Brain," *Proc. Nat'l Acad. Sci. USA*, 88:10173–10177, November 1991.

Florio and Ross, *Mol. Pharmacol.*, 24:195, 1983.

Gao and Gilman, "Cloning and Expression of a Widely Distributed (type IV) Adenylyl Cyclase," *Proc. Nat'l Acad. Sci. USA*, 88:10178–10182, November 1991.

Graziano and Gilman, *J. Biol. Chem.*, 264:15475, 1989.

Harris et al., PROTEIN PURIFICATION METHODS—A PRACTICAL APPROACH,IRL Press, Oxford, 1989.

Henry et al., *FEBS Lett.*, 144:11–15,1982.

Heuschneider and Schwartz, *Proc. Nat'l Acad. Sci. USA*, 86:2938, 1989.

Hoshi et al., *Science*, 240:1652, 1988.

Johnson and Shoshani, *J. Biol. Chem.*, 265:11595, 1990.

Joost et al., *Mol. Pharmacol.*, 33:449, 1988.

Kashiwagi et al., *J. Biol. Ghem.*, 258:13685, 1983.

Katsushika et al., "Cloning and Characterization of a Sixth Adenylyl Cyclase Isoform: Types V and VI Constitute a Subgroup within the Mammalian Adenylyl Cyclase Family," *Proc. Nat'l Acad. Sci. USA*, 89:8774–8778, September 1992.

Knoll and Gordon, *J. Biol. Chem.*, 268:4281, 1993.

Krupinski et al., "Adenylyl Cyclase Amino Acid Sequence: Possible Channel- or Transporter-Like Structure," *Science*, 244:1558–1564, June 1989.

Krupinski et al., "Molecular Diversity in the Adenylylcyclase Family," *The Journal of Biological Chemistry*, 267(34):24558–24862,1992.

Kunkel et al., *Meth. Enzymol.*, 154:367, 1987.

Kyte and Doolittle, *J. Mol. Biol.*, 157, 105 (1982)

Miles et al., *J. Mol. Biol.*, 202:97–106, 1988.

Morris et al., *Biochemistry*, 30:8371, 1991.

Morris et al., *Mol. Pharmacol.*, 46:329, 1994.

Neer et al., *J. Biol. Chem.*, 255:9782–9789, 1980.

Noel et al., *Nature*, 366:654, 1993.

Perham et al., *Nature*, 292:474–477, 1981.

Perham and Roberts, *Biochem. J.*, 199:733–740, 1981.

Perlman and Pastan, *Biochem. Biophys. Res. Commun.*, 37:151, 1969.

Pfeuffer et al., *Proc. Natl. Acad. Sci., USA*, 82:3086–3090, 1985.

Premont et al., "Two Members of a Widely Expressed Subfamily of Hormone-Stimulated Adenylyl Cyclases," *Proc. Nat'l Acad. Sci. USA*, 89:9809–9813, October 1992.

Radford et al., *J. Biol. Chem.*, 264:767–775, 1989.

Radford et al., *Biochem. J.*, 247:641–649, 1987.

Roy and Danchin, *Mol. Gen. Genetics*, 188:465, 1982.

Salomon et al., *Anal. Biochem.* 58:541–548, 1974.

Seamon and Daly, *Adv. Cyclic Nucleotide Res.*, 20:1, 1986.

Seamon et al., *J. Med. Chem.*, 26:436, 1983.

Smigel, *J. Biol. Chem.*, 261:1976–1982,1986.

Summers et al., A MANUAL OF METHODS FOR BACULOVIRUS VECTORS AND INSECT CELL CULTURE PROCEDURES, Texas Agricultural Experimental Station (1987).

Sunahara et al., *Annu. Rev. Pharmacol. Toxicol.*, 36:461–480, 1996.

Sutkowski et al., *Biochemistry*, 33:12852, 1994.

Tang et al., *Science*, 268:1769–1772, 1995.

Tang, et al., *Biochemistry*, 34:14563–14572, 1995.

Tang et al., *The Cell Surface—Symposium* 57, Cold Spring Harbor Laboratory Press, Cold Spring Harbor, N.Y., 1992.

Tang and Gilman, *Cell*, 70:869, 1992.

Tang et al., "Expression and Characterization of Calmodulin-activated (Type 1) Adenylylcyclase," *The Journal of Biological Chemistry*, 266(13):8595–8603, May, 1991.

Taussig and Gilman, *J. Biol. Chem.*, 270:1, 1995.

Taussig et al., "Expression and Purification of Recombinant Adenylyl Cyclases in Sf9 Cells," *Methods in Enzymology*, 238:95–109, 1994.

Texter et al., *Biochemistry* 27:289–296, 1988.

Vaara, *Microbiol. Rev.*, 56:395, 1992.

Wadler and Wiernik, *Cancer Res.* 48:539, 1988.

Wadzinski et al., *Biochem. J.*, 272:151, 1990.

Wagoner and Pallotta, *Science*, 240:1655, 1988.

Wallach et al., *FEBS Lett.*, 338:264–266, 1994.

Watson et al., "Molecular Cloning and Characterization of the Type VII Isoform of Mammalian Adenylyl Cyclase Expressed Widely in Mouse Tissures and in S49 Mouse Lymphoma Cells," *The Journal of Biological Chemistry*, 269(46):28893–28898, November 1994.

Yoshimura and Cooper, *Proc. Nat'l Acad. Sci. USA*, 89:6716–6720, 1992.

What is claimed is:

1. A soluble mammalian polypeptide composition having adenylyl cyclase activity, wherein said polypeptide is activated by $G_{s\alpha}$.

2. The polypeptide composition according to claim 1, wherein said polypeptide composition comprises one or more polypeptides that lack transmembrane regions.

3. The polypeptide composition according to claim 2, wherein said polypeptide composition comprises a chimera of adenylyl cyclase $C_1$ and $C_2$ domains linked covalently.

4. The polypeptide composition according to claim 3, wherein said chimera comprises adenylyl cyclase type I-$C_1$ and type II-$C_2$ domains, but lacks membrane-bound domains.

5. The polypeptide composition according to claim 3, wherein said chimera comprises adenylyl cyclase type V-$C_1$ and type II-$C_2$ domains, but lacks membrane-bound domains.

6. The polypeptide composition according to claim 4, wherein said type I-$C_1$ domain has a $C_{1a}$ domain sequence from SEQ ID NO:2 and said type II-$C_2$ domain has a $C_{2a}$ domain sequence from SEQ ID NO:4.

7. The polypeptide composition according to claim 6, wherein said $C_{1a}$ and $C_{2a}$ domains are joined by a linker peptide.

8. The polypeptide composition according to claim 7, wherein said linker peptide has a sequence selected from the group consisting of AAAGGM (SEQ ID NO:19), AAAG-GMPPAAAGGM (SEQ ID NO:20) and AAAGGM (PPAAAGGM)$_2$ (SEQ ID NO:21).

9. The polypeptide composition according to claim 7, wherein said chimera has the amino acid sequence of SEQ ID NO:18.

10. The polypeptide composition according to claim 2, wherein said polypeptide composition forms a complex comprising two distinct polypeptides, one of which is an adenylyl cyclase $C_1$ domain and one of which is an adenylyl cyclase $C_2$ domain.

11. The polypeptide composition according to claim 10, wherein said $C_1$ domain is a type I $C_1$ domain and said $C_2$ domain is a type II $C_2$ domain.

12. The polypeptide composition according to claim 10, wherein said $C_1$ domain is a type V $C_1$ domain and said $C_2$ domain is a type II $C_2$ domain.

13. The polypeptide composition according to claim 11, wherein said type I-$C_1$ domain has a $C_{1a}$ domain sequence from SEQ ID NO:2 and said type II-$C_2$ domain has a $C_{2a}$ domain sequence from SEQ ID NO:4.

14. A polynucleotide encoding a soluble mammalian polypeptide having adenylyl cyclase activity, wherein said polypeptide is activated by $G_{s\alpha}$.

15. The polynucleotide according to claim 14, wherein said polynucleotide does not encode transmembrane regions.

16. The polynucleotide according to claim 15, wherein said polynucleotide encodes a chimera of adenylyl cyclase $C_1$ and $C_2$ domains.

17. The polynucleotide according to claim 16, wherein said polynucleotide has the nucleotide sequence of SEQ ID NO:17.

18. A polynucleotide consisting of a coding region for an adenylyl cyclase $C_1$ domain.

19. A polynucleotide consisting of a coding region for an adenylyl cyclase $C_2$ domain.

20. An expression vector comprising a polynucleotide encoding a soluble mammalian polypeptide having adenylyl cyclase activity, operably linked to a promoter, wherein said polypeptide is activated by $G_{s\alpha}$.

21. An expression vector comprising a polynucleotide, wherein said polynucleotide comprises a coding region for at least one of an adenylyl cyclase $C_1$ or $C_2$ domain, operably linked to a promoter, but lacks a coding region for an adenylyl cyclase domain that is membrane bound in situ.

22. A host cell comprising the expression vector of claim 20.

23. The host cell of claim 22, wherein the cell is (i) a bacterial cell or (ii) a cell capable of supporting baculovirus replication.

24. The host cell of claim 22, further comprising an expression vector comprising a polynucleotide encoding the alpha subunit of G protein, operably linked to a promoter active in said host cell.

25. A host cell comprising the expression vector of claim 21.

26. A host cell comprising an expression vector comprising a polynucleotide, wherein said polynucleotide comprises a coding region for at least one of an adenylyl cyclase $C_1$ or $C_2$ domain, operably linked to a promoter, but lacks a coding region for adenylyl cyclase domain that is membrane bound in situ.

27. The host cell of claim 26, further comprising an expression vector comprising a polynucleotide encoding the alpha subunit of G protein, operably linked to a promoter active in said host cell.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 3978 base pairs
        (B) TYPE: nucleic acid
        (C) STRANDEDNESS: single
        (D) TOPOLOGY: linear (xi) SEQUENCE DESCRIPTION: SEQ ID NO:1:

| | | | | | |
|---|---|---|---|---|---|
| GCCGGCGCCC | CAACTCGGCC | CGCCGCGCCC | CGGCGCCTCG | CCGCCCGCCC | GCCCGCCCGG | 60 |
| CGCCCCGGCC | GGCGAGGGGC | GCGCCCGCTG | CATGGCGCTG | GGATGGCGGG | GGCGCCGCGC | 120 |
| GGCCGAGGCG | GCGGCGGAGG | CGGAGGCGGC | GCGGGCGAGT | CTGGGGCGC | CGAGCGGGCG | 180 |
| GCGGGGCCGG | GCGGCCGGCG | CGGGCTGCGG | GCGTGCGATG | AGGAGTTCGC | GTGCCCCGAG | 240 |
| CTGGAGGCGC | TGTTCCGCGG | CTACACGCTG | CGGCTGGAGC | AGGCGGCGAC | GCTGAAGGCG | 300 |
| CTGGCCGTGC | TCAGCCTGCT | GGCGGGCGCG | CTGGCCCTGG | CCGAGCTGCT | GGGCGCGCCG | 360 |
| GGGCCCGCGC | CCGGCCTGGC | TAAGGGCTCG | CACCCCGTGC | ACTGCGTGCT | CTTCCTGGCG | 420 |
| CTGCTCGTGG | TCACCAACGT | CCGCTCGCTG | CAGGTGCCCC | AGCTGCAGCA | GGTCGGCCAG | 480 |
| CTCGCGCTGC | TCTTCAGCCT | CACCTTCGCT | CTGCTGTGCT | GTCCCTTCGC | GCTCGGCGGC | 540 |
| CCCGCCGGTG | CCCACGCCGG | GGCGGCAGCG | GTGCCGGCGA | CAGCCGATCA | GGGAGTCTGG | 600 |
| CAGCTCCTTT | TGGTCACCTT | CGTGTCCTAT | GCCCTGCTGC | CCGTGCGCAG | CCTGCTGGCC | 660 |
| ATCGGCTTCG | GGCTCGTGGT | GGCCGCCTCG | CACTTGCTGG | TCACGGCTAC | GTTGGTCCCC | 720 |
| GCCAAGCGCC | CACGTCTCTG | GAGAACGCTG | GGTGCCAACG | CTCTGCTCTT | CCTCGGTGTG | 780 |
| AACGTGTATG | GCATCTTCGT | GAGGATCCTG | GCTGAGCGCG | CCCAGAGGAA | GGCCTTCCTG | 840 |
| CAGGCCCGGA | ACTGCATTGA | GGACCGGCTG | AGGCTGGAGG | ATGAGAATGA | GAAGCAGGAG | 900 |
| CGGCTGCTCA | TGAGCCTCCT | GCCTCGGAAT | GTTGCCATGG | AGATGAAGGA | GGACTTCCTG | 960 |
| AAGCCCCCTG | AGAGGATTTT | CCACAAGATT | TACATCCAGC | GGCATGACAA | CGTGAGCATC | 1020 |
| CTCTTTGCAG | ACATCGTGGG | CTTCACAGGC | TTGGCGTCAC | AGTGCACGGC | CCAGGAGCTG | 1080 |
| GTGAAACTCC | TCAATGAGCT | CTTCGGGAAG | TTTGACGAGC | TGGCCACAGA | GAACCACTGC | 1140 |
| CGCCGCATCA | AGATCCTGGG | AGATTGCTAC | TACTGCGTGT | CTGGCCTCAC | TCAGCCCAAG | 1200 |
| ACTGACCACG | CCCACTGCTG | TGTGGAGATG | GGCCTGGACA | TGATCGACAC | CATCACGTCC | 1260 |
| GTGGCTGAGG | CCACTGAGGT | GGACTTGAAC | ATGCGTGTGG | GGCTGCACAC | CGGCAGGGTC | 1320 |
| CTCTGCGGGG | TCCTGGGCCT | GCGTAAGTGG | CAGTATGATG | TGTGGTCCAA | CGACGTGACC | 1380 |
| CTGGCCAACG | TCATGGAGGC | TGCCGGCCTG | CCTGGGAAGG | TTCACATCAC | AAAGACCACC | 1440 |
| CTGGCGTGCC | TGAATGGTGA | CTATGAGGTG | GAGCCGGGAC | ACGGACACGA | GAGGAACAGT | 1500 |
| TTTCTGAAAA | CTCATAACAT | TGAGACCTTT | TTTATTGTGC | CCTCGCATCG | GCGAAAGATA | 1560 |
| TTTCCAGGGC | TGATTCTCTC | AGACATAAAA | CCGGCCAAGA | GGATGAAGTT | CAAGACCGTG | 1620 |
| TGCTACCTGC | TGGTGCAGCT | CATGCACTGC | CGGAAGATGT | TCAAGGCCGA | GATCCCTTTC | 1680 |
| TCCAACGTCA | TGACCTGTGA | GGATGACGAC | AAGCGGAGGG | CACTGAGAAC | AGCCTCGGAA | 1740 |
| AAACTCAGAA | ACCGCTCGTC | TTTCTCTACA | AACGTTGTCC | AAACCACCCC | CGGCACACGT | 1800 |
| GTCAACAGGT | ACATCGGCCG | CCTCCTGGAA | GCCCGCCAGA | TGGAGCTGGA | GATGGCAGAC | 1860 |

```
CTGAACTTCT TCACCCTGAA GTACAAGCAA GCTGAGCGAG AGCGAAAGTA CCACCAGCTT    1920

CAGGACGAGT ATTTCACCAG CGCCGTGGTT CTGGCTCTCA TTCTGGCCGC CTTATTCGGC    1980

CTTGTCTACC TTCTAATAAT CCCACAGAGT GTGGCTGTCC TGCTCCTGCT GGTGTTCTGC    2040

ATCTGCTTCC TGGTGGCCTG TGTCCTGTAC CTACACATCA CCCGGGTCCA GTGTTTTCCA    2100

GGGTGCCTGA CCATCCAGAT CCGCACCGTC TTGTGCATCT TCATCGTGGT CTTAATCTAC    2160

TCTGTGGCCC AAGGCTGTGT GGTGGGCTGC CTGCCTTGGT CCTGGAGCTC CAGTCCCAAC    2220

GGGTCCCTGG TGGTCCTGTC TTCTGGGGGC CGGGACCCAG TGCTGCCTGT CCCGCCCTGC    2280

GAGTCTGCGC CCCATGCCCT GCTGTGCGGC CTCGTGGGCA CCCTCCCGCT GGCCATATTC    2340

CTGCGGGTCT CCTCCTTGCC AAAAATGATC CTGCTCGCCG TGCTCACCAC CTCCTACATC    2400

CTCGTCCTGG AGCTCAGCGG GTACACGAAG GCCATGGGGG CCGGTGCCAT CTCAGGGCGC    2460

AGCTTCGAGC CGATCATGGC CATCCTGCTA TTCTCGTGCA CGCTGGCCCT GCACGCCCGG    2520

CAGGTGGATG TCAAGCTGCG GCTGGACTAC CTCTGGGCGG CCCAGGCAGA GGAGGAGCGG    2580

GATGACATGG AGAAAGTGAA GCTGGACAAC AAGAGGATTC TCTTCAACCT CCTGCCAGCC    2640

CACGTTGCCC AGCACTTCCT AATGTCCAAC CCTCGCAACA TGGACCTGTA TTACCAGTCA    2700

TACTCGCAGG TGGGGGTCAT GTTTGCATCC ATCCCCAACT TCAATGACTT CTACATCGAG    2760

CTGGATGGCA ACAACATGGG GGTGGAATGT CTACGCCTTC TGAATGAGAT CATCGCTGAC    2820

TTTGATGAGC TCATGGACAA AGACTTTTAC AAGGACCTAG AGAAGATCAA GACCATTGGG    2880

AGCACGTACA TGGCTGCTGT GGGGCTGGCG CCCACTGCTG GGACCAAGGC TAAGAAGTGC    2940

ATCTCCTCCC ACCTCAGCAC GTTGGCAGAT TTTGCCATCG AGATGTTTGA TGTCCTGGAT    3000

GAGATCAACT ACCAGTCTTA TAACGACTTT GTGCTCCGTG TTGGCATCAA TGTTGGCCCC    3060

GTGGTGGCTG GAGTGATCGG GGCTCGCAGG CCGCAGTATG ACATTTGGGG GAACACGGTC    3120

AATGTGGCCA GTCGGATGGA CAGTACCGGC GTCCAGGGCA GGATCCAGGT CACAGAGGAA    3180

GTTCACCGGC TGCTGCGGCG GGGTTCCTAC CGCTTCGTGT GCCGAGGCAA AGTCAGTGTC    3240

AAGGGCAAGG GTGAGATGCT GACATACTTC CTGGAAGGCA GGACCGATGG AAAATGGCTCC   3300

CAAACCAGGT CCCTGAACTC AGAGCGGAAA ATGTATCCTT TCGGAAGAGC TGGCCTCCAG    3360

ACCAGACTGG CTGCGGGTCA CCCCCCGGTA CCTCCTGCAG CCGGCCTCCC AGTTGGAGCT    3420

GGGCCAGGGG CTCTGCAGGG CTCGGGGCTT GCCCCAGGCC CCCCAGGCCA ACACCTGCCC    3480

CCTGGAGCCT CTGGGAAGGA GGCTTAGTGG AGCCCATGCC AGCCGCTTGG GGCACAGGGC    3540

ACAAATGCTT GAGGTATTGG GGGTCTTTGG GGCTCCCCCA GGGACCAGCC CAGCCAGCAG    3600

AGCAGGGCTG GGAGCTGGTG ACTGGGCTGG GGAAGGGGCA CAGTCCAGGC ATGACTTGAA    3660

GCAGCTGGGC AGTGAGTCCA GCAGTGAGTC GGGTGAGGGG CGAACCCTGA CCGCACGGAC    3720

ACCGAGGTTT TAGCGGCGAC TGTGTTTGCT TTGTCCTCAC CTCAGTGGCA GAGGGAGGTT    3780

GGCTGGGTCA GCTCCAGGTG TCAGAACGTT CAGGACATTC TCCAGGGCCA TAGGCTACAG    3840

TGAGAGCCTC AGAGGTCTGG CTGGCAGAGT GACTGGGGCG CCCACCTTGT GCCCTGAGAT    3900

GGATCAGCGT CAGCCCAGCA GTGTGGGTCC ATGGGGCAG CTCCAGCCCT GGGCAGTGGC    3960

CTGCAGAGCC CGGAGTGG                                                 3978
```

(2) INFORMATION FOR SEQ ID NO:2:

(i) SEQUENCE CHARACTERISTICS:
        (A) LENGTH: 1134 amino acids
        (B) TYPE: amino acid -continued (C) STRANDEDNESS:
(D) TOPOLOGY: linear (xi) SEQUENCE DESCRIPTION: SEQ ID NO:2:

```
Met Ala Gly Ala Pro Arg Gly Arg Gly Gly Gly Gly Gly Gly Gly
1               5                   10                  15

Ala Gly Glu Ser Gly Gly Ala Glu Arg Ala Ala Gly Pro Gly Gly Arg
            20                  25                  30

Arg Gly Leu Arg Ala Cys Asp Glu Glu Phe Ala Cys Pro Glu Leu Glu
            35                  40                  45

Ala Leu Phe Arg Gly Tyr Thr Leu Arg Leu Glu Gln Ala Ala Thr Leu
        50                  55                  60

Lys Ala Leu Ala Val Leu Ser Leu Leu Ala Gly Ala Leu Ala Leu Ala
65                  70                  75                  80

Glu Leu Leu Gly Ala Pro Gly Pro Ala Pro Gly Leu Ala Lys Gly Ser
                    85                  90                  95

His Pro Val His Cys Val Leu Phe Leu Ala Leu Leu Val Val Thr Asn
                100                 105                 110

Val Arg Ser Leu Gln Val Pro Gln Leu Gln Gln Val Gly Gln Leu Ala
            115                 120                 125

Leu Leu Phe Ser Leu Thr Phe Ala Leu Leu Cys Cys Pro Phe Ala Leu
        130                 135                 140

Gly Gly Pro Ala Gly Ala His Ala Gly Ala Ala Ala Val Pro Ala Thr
145                 150                 155                 160

Ala Asp Gln Gly Val Trp Gln Leu Leu Leu Val Thr Phe Val Ser Tyr
                    165                 170                 175

Ala Leu Leu Pro Val Arg Ser Leu Leu Ala Ile Gly Phe Gly Leu Val
                180                 185                 190

Val Ala Ala Ser His Leu Leu Val Thr Ala Thr Leu Val Pro Ala Lys
            195                 200                 205

Arg Pro Arg Leu Trp Arg Thr Leu Gly Ala Asn Ala Leu Leu Phe Leu
        210                 215                 220

Gly Val Asn Val Tyr Gly Ile Phe Val Arg Ile Leu Ala Glu Arg Ala
225                 230                 235                 240

Gln Arg Lys Ala Phe Leu Gln Ala Arg Asn Cys Ile Glu Asp Arg Leu
                    245                 250                 255

Arg Leu Glu Asp Glu Asn Glu Lys Gln Glu Arg Leu Leu Met Ser Leu
                260                 265                 270

Leu Pro Arg Asn Val Ala Met Glu Met Lys Glu Asp Phe Leu Lys Pro
            275                 280                 285

Pro Glu Arg Ile Phe His Lys Ile Tyr Ile Gln Arg His Asp Asn Val
        290                 295                 300

Ser Ile Leu Phe Ala Asp Ile Val Gly Phe Thr Gly Leu Ala Ser Gln
305                 310                 315                 320

Cys Thr Ala Gln Glu Leu Val Lys Leu Leu Asn Glu Leu Phe Gly Lys
                    325                 330                 335

Phe Asp Glu Leu Ala Thr Glu Asn His Cys Arg Arg Ile Lys Ile Leu
                340                 345                 350

Gly Asp Cys Tyr Tyr Cys Val Ser Gly Leu Thr Gln Pro Lys Thr Asp
            355                 360                 365

His Ala His Cys Cys Val Glu Met Gly Leu Asp Met Ile Asp Thr Ile
        370                 375                 380

Thr Ser Val Ala Glu Ala Thr Glu Val Asp Leu Asn Met Arg Val Gly
385                 390                 395                 400
```

-continued

```
Leu His Thr Gly Arg Val Leu Cys Gly Val Leu Gly Leu Arg Lys Trp
                405                 410                 415
Gln Tyr Asp Val Trp Ser Asn Asp Val Thr Leu Ala Asn Val Met Glu
                420                 425                 430
Ala Ala Gly Leu Pro Gly Lys Val His Ile Thr Lys Thr Thr Leu Ala
                435                 440                 445
Cys Leu Asn Gly Asp Tyr Glu Val Glu Pro Gly His Gly His Glu Arg
                450                 455                 460
Asn Ser Phe Leu Lys Thr His Asn Ile Glu Thr Phe Phe Ile Val Pro
465                 470                 475                 480
Ser His Arg Arg Lys Ile Phe Pro Gly Leu Ile Leu Ser Asp Ile Lys
                485                 490                 495
Pro Ala Lys Arg Met Lys Phe Lys Thr Val Cys Tyr Leu Leu Val Gln
                500                 505                 510
Leu Met His Cys Arg Lys Met Phe Lys Ala Glu Ile Pro Phe Ser Asn
                515                 520                 525
Val Met Thr Cys Glu Asp Asp Asp Lys Arg Arg Ala Leu Arg Thr Ala
                530                 535                 540
Ser Glu Lys Leu Arg Asn Arg Ser Ser Phe Ser Thr Asn Val Val Gln
545                 550                 555                 560
Thr Thr Pro Gly Thr Arg Val Asn Arg Tyr Ile Gly Arg Leu Leu Glu
                565                 570                 575
Ala Arg Gln Met Glu Leu Glu Met Ala Asp Leu Asn Phe Phe Thr Leu
                580                 585                 590
Lys Tyr Lys Gln Ala Glu Arg Glu Arg Lys Tyr His Gln Leu Gln Asp
                595                 600                 605
Glu Tyr Phe Thr Ser Ala Val Val Leu Ala Leu Ile Leu Ala Ala Leu
                610                 615                 620
Phe Gly Leu Val Tyr Leu Ile Ile Pro Gln Ser Val Ala Val Leu
625                 630                 635                 640
Leu Leu Leu Val Phe Cys Ile Cys Phe Leu Val Ala Cys Val Leu Tyr
                645                 650                 655
Leu His Ile Thr Arg Val Gln Cys Phe Pro Gly Cys Leu Thr Ile Gln
                660                 665                 670
Ile Arg Thr Val Leu Cys Ile Phe Ile Val Val Leu Ile Tyr Ser Val
                675                 680                 685
Ala Gln Gly Cys Val Val Gly Cys Leu Pro Trp Ser Trp Ser Ser Ser
                690                 695                 700
Pro Asn Gly Ser Leu Val Val Leu Ser Ser Gly Gly Arg Asp Pro Val
705                 710                 715                 720
Leu Pro Val Pro Pro Cys Glu Ser Ala Pro His Ala Leu Leu Cys Gly
                725                 730                 735
Leu Val Gly Thr Leu Pro Leu Ala Ile Phe Leu Arg Val Ser Ser Leu
                740                 745                 750
Pro Lys Met Ile Leu Leu Ala Val Leu Thr Thr Ser Tyr Ile Leu Val
                755                 760                 765
Leu Glu Leu Ser Gly Tyr Thr Lys Ala Met Gly Ala Gly Ala Ile Ser
                770                 775                 780
Gly Arg Ser Phe Glu Pro Ile Met Ala Ile Leu Leu Phe Ser Cys Thr
785                 790                 795                 800
Leu Ala Leu His Ala Arg Gln Val Asp Val Lys Leu Arg Leu Asp Tyr
                805                 810                 815
```

```
Leu Trp Ala Ala Gln Ala Glu Glu Arg Asp Asp Met Glu Lys Val
        820                 825                 830

Lys Leu Asp Asn Lys Arg Ile Leu Phe Asn Leu Leu Pro Ala His Val
        835                 840                 845

Ala Gln His Phe Leu Met Ser Asn Pro Arg Asn Met Asp Leu Tyr Tyr
        850                 855                 860

Gln Ser Tyr Ser Gln Val Gly Val Met Phe Ala Ser Ile Pro Asn Phe
865                 870                 875                 880

Asn Asp Phe Tyr Ile Glu Leu Asp Gly Asn Asn Met Gly Val Glu Cys
                    885                 890                 895

Leu Arg Leu Leu Asn Glu Ile Ile Ala Asp Phe Asp Glu Leu Met Asp
                900                 905                 910

Lys Asp Phe Tyr Lys Asp Leu Glu Lys Ile Lys Thr Ile Gly Ser Thr
                915                 920                 925

Tyr Met Ala Ala Val Gly Leu Ala Pro Thr Ala Gly Thr Lys Ala Lys
        930                 935                 940

Lys Cys Ile Ser Ser His Leu Ser Thr Leu Ala Asp Phe Ala Ile Glu
945                 950                 955                 960

Met Phe Asp Val Leu Asp Glu Ile Asn Tyr Gln Ser Tyr Asn Asp Phe
                965                 970                 975

Val Leu Arg Val Gly Ile Asn Val Gly Pro Val Val Ala Gly Val Ile
                980                 985                 990

Gly Ala Arg Arg Pro Gln Tyr Asp Ile Trp Gly Asn Thr Val Asn Val
                995                 1000                1005

Ala Ser Arg Met Asp Ser Thr Gly Val Gln Gly Arg Ile Gln Val Thr
        1010                1015                1020

Glu Glu Val His Arg Leu Leu Arg Arg Gly Ser Tyr Arg Phe Val Cys
1025                1030                1035                1040

Arg Gly Lys Val Ser Val Lys Gly Lys Gly Glu Met Leu Thr Tyr Phe
                1045                1050                1055

Leu Glu Gly Arg Thr Asp Gly Asn Gly Ser Gln Thr Arg Ser Leu Asn
                1060                1065                1070

Ser Glu Arg Lys Met Tyr Pro Phe Gly Arg Ala Gly Leu Gln Thr Arg
                1075                1080                1085

Leu Ala Ala Gly His Pro Pro Val Pro Pro Ala Ala Gly Leu Pro Val
        1090                1095                1100

Gly Ala Gly Pro Gly Ala Leu Gln Gly Ser Gly Leu Ala Pro Gly Pro
1105                1110                1115                1120

Pro Gly Gln His Leu Pro Pro Gly Ala Ser Gly Lys Glu Ala
                1125                1130

(2) INFORMATION FOR SEQ ID NO:3:

(i) SEQUENCE CHARACTERISTICS:
        (A) LENGTH: 4008 base pairs
        (B) TYPE: nucleic acid
        (C) STRANDEDNESS: single
        (D) TOPOLOGY: linear (xi) SEQUENCE DESCRIPTION: SEQ ID NO:3:

CCCGGGCAGC GCGCTCTGCG GTCGCCTACC GCCTGCCGCC CCCGCGCCGC CGCGACGTGG      60

CAGGAGGCGA TGCGGCGGCG CCGCTACCTG CGGGACCGCG CCGAGGCGGC GGCGGCAGCG     120

GCGGCGGGAG GCGGAGAGGG GCTGCAGCGG TCCCGGGACT GGCTCTACGA GTCCTACTAC     180

TGCATGAGCC AGCAGCACCC GCTCATCGTC TTCCTGCTGC TCATCGTCAT GGGCGCCTGC     240
```

-continued

| | | | | | |
|---|---|---|---|---|---|
| CTCGCCCTGC | TAGCCGTCTT | CTTCGCGCTC | GGGCTGGAGG | TGGAAGACCA | TGTGGCATTT | 300 |
| TTAATAACGG | TTCCCACTGC | CCTGGCCATT | TTCTTTGCCA | TATTCATTCT | TGTCTGCATA | 360 |
| GAGTCTGTGT | TCAAGAAGCT | ACTCCGTGTG | TTTTCGCTGG | TGATTTGGAT | ATGTCTGGTT | 420 |
| GCCATGGGAT | ACCTGTTCAT | GTGCTTCGGA | GGGACTGTGT | CTGCCTGGGA | CCAGGTGTCA | 480 |
| TTCTTCCTCT | TCATCATCTT | TGTGGTATAT | ACCATGCTTC | CCTTCAACAT | GCGAGATGCC | 540 |
| ATCATTGCCA | GCATCCTCAC | ATCTTCATCT | CATACGATAG | TGCTGAGCGT | CTACCTGTCT | 600 |
| GCAACACCAG | GGGCCAAGGA | GCACCTGTTC | TGGCAGATAC | TGGCCAATGT | GATCATTTTC | 660 |
| ATTTGTGGGA | ACTTGGCGGG | AGCCTACCAC | AAGCACCTCA | TGGAGCTTGC | CTTGCAGCAA | 720 |
| ACCTATCGGG | ACACGTGTAA | TTGCATCAAG | TCCCGGATCA | AGCTGGAATT | TGAAAAACGG | 780 |
| CAGCAGGAAC | GGCTCCTGCT | CTCCTTGCTG | CCAGCTCACA | TCGCCATGGA | GATGAAAGCT | 840 |
| GAAATCATTC | AGAGGCTGCA | GGGCCCCAAA | GCAGGACAGA | TGGAAAACAC | AAACAACTTC | 900 |
| CACAATCTGT | ATGTCAAACG | ACACACCAAC | GTGAGCATAT | TATACGCTGA | CATTGTTGGC | 960 |
| TTCACCCGCC | TTGCAAGCGA | TTGCTCCCCT | GGCGAACTGG | TCCACATGCT | GAATGAACTC | 1020 |
| TTTGGGAAGT | TTGATCAAAT | AGCAAAGGAG | AATGAATGCA | TGAGAATTAA | AATTTTAGGA | 1080 |
| GACTGCTATT | ACTGTGTTTC | CGGGCTCCCT | ATATCACTCC | CTAACCATGC | CAAGAACTGT | 1140 |
| GTGAAAATGG | GATTGGATAT | GTGCGAAGCC | ATAAAGAAAG | TGAGGGATGC | TACCGGAGTT | 1200 |
| GATATCAACA | TGCGTGTAGG | AGTGCATTCT | GGGAACGTTC | TCTGTGGTGT | GATTGGTCTC | 1260 |
| CAGAAGTGGC | AGTATGATGT | GTGGTCTCAT | GATGTTACTC | TGGCAAACCA | CATGGAAGCT | 1320 |
| GGAGGAGTCC | CTGGGCGTGT | TCACATTTCT | TCAGTCACTC | TGGAGCACTT | GAATGGGGCT | 1380 |
| TATAAAGTGG | AGGAAGGAGA | TGGTGAGATA | AGAGACCCAT | ATTTAAAGCA | GCACTTGGTG | 1440 |
| AAAACCTACT | TTGTAATCAA | TCCCAAGGGA | GAGCGACGGA | GTCCTCAGCA | TCTCTTCAGA | 1500 |
| CCTCGACACA | CTCTGGACGG | AGCCAAGATG | AGAGCATCTG | TCCGCATGAC | CCGGTACTTG | 1560 |
| GAGTCCTGGG | GAGCAGCCAA | GCCATTCGCA | CATCTGCACC | ACAGAGATAG | CATGACCACA | 1620 |
| GAGAATGGGA | AGATTAGTAC | CACGGATGTG | CCAATGGGTC | AACATAATTT | TCAAAATCGC | 1680 |
| ACCTTAAGAA | CTAAGTCACA | GAAGAAGAGA | TTTGAAGAAG | AACTGAATGA | AAGGATGATC | 1740 |
| CAAGCAATTG | ATGGGATCAA | TGCACAGAAG | CAATGGCTCA | AGTCAGAAGA | CATTCAAAGA | 1800 |
| ATCTCCCTGC | TTTTCTATAA | CAAGAATATA | GAGAAAGAAT | ACCGAGCTAC | TGCACTGCCA | 1860 |
| GCATTCAAGT | ACTACGTGAC | CTGTGCCTGC | CTCATCTTTC | TCTGCATCTT | CATTGTACAG | 1920 |
| ATACTTGTAT | TGCCAAAAAC | GTCCATCCTT | GGCTTCTCCT | TTGGAGCTGC | ATTTCTCTCC | 1980 |
| CTCATCTTCA | TCCTCTTTGT | CTGCTTCGCT | GGACAGCTTT | TGCAATGCAG | CAAAAAGGCC | 2040 |
| TCCACCTCTC | TCATGTGGCT | TTTGAAATCA | TCAGGCATCA | TCGCCAACCG | CCCATGGCCA | 2100 |
| CGGATCTCCC | TCACAATCGT | CACCACGGCT | ATCATACTAA | CCATGGCTGT | GTTCAACATG | 2160 |
| TTTTTCCTGA | GCAACTCTGA | GGAGACAACC | CTTCCCACTG | CCAATACATC | AAATGCAAAC | 2220 |
| GTTTCTGTCC | CGGATAACCA | GGCGTCGATT | CTTCATGCTC | GAAACTTGTT | TTTCCTCCCG | 2280 |
| TACTTCATAT | ACAGCTGCAT | CCTGGGCTTG | ATCTCCTGCT | CCGTTTTCCT | GAGGGTGAAC | 2340 |
| TATGAGTTAA | AAATGTTAAT | CATGATGGTG | GCACTCGTGG | GCTACAACAC | CATTCTACTC | 2400 |
| CACACCCATG | CCCATGTTCT | GGATGCGTAC | AGCCAGGTCC | TGTTTCAGAG | ACCAGGCATT | 2460 |
| TGGAAAGACC | TGAAGACCAT | GGGCTCCGTG | TCACTCTCCA | TATTCTTCAT | CACGCTGCTG | 2520 |
| GTTCTGGGCA | GACAGAGTGA | ATATTACTGT | AGGTTAGACT | TCTTGTGGAA | GAACAAGTTC | 2580 |
| AAAAAGAGC | GGGAGGAGAT | AGAAACCATG | GAGAACCTAA | ATCGAGTGCT | GCTGGAGAAC | 2640 |

```
GTGCTTCCTG CACACGTGGC TGAACACTTC CTGGCCAGGA GCCTGAAAAA TGAGGAGCTG    2700

TACCACCAGT CCTACGACTG TGTCTGTGTC ATGTTTGCCT CCATTCCGGA CTTCAAGGAG    2760

TTCTACACAG AGTCAGATGT GAACAAGGAA GGCTTGGAAT GCCTGCGGCT CCTGAATGAG    2820

ATCATTGCTG ACTTTGATGA TCTGCTTTCT AAGCCAAAGT TCAGTGGTGT TGAAAAGATC    2880

AAGACCATTG GGAGCACATA CATGGCAGCC ACGGGACTGA GTGCCATACC CAGCCAGGAG    2940

CACGCCCAGG AACCTGAGCG TCAGTACATG CACATAGGCA CCATGGTGGA GTTTGCATAT    3000

GCCCTGGTGG AAAACTGGA TGCCATCAAT AAGCACTCCT TCAACGACTT CAAACTGCGA    3060

GTGGGTATCA ACCATGGGCC TGTAATAGCT GGCGTCATAG GGCTCAAAA GCCACAGTAT    3120

GACATCTGGG GCAACACTGT CAACGTGGCC AGCAGAATGG ACAGCACCGG GGTCCTGGAC    3180

AAAATACAGG TGACTGAGGA GACAAGCCTC ATCTTGCAGA CGCTTGGCTA CACGTGTACA    3240

TGTCGAGGTA TCATCAATGT GAAGGGGAAA GGGGACCTGA AGACATATTT TGTAAACACA    3300

GAGATGTCAA GGTCCCTTTC TCAGAGCAAC TTGGCATCCT GAGAAGCTGT CTCTTCCTGA    3360

CAAGAAGAAT GTACTTGCAG GAAGGTACCA CGCACTTTCT GACTGCAACC CTTCCCCTTC    3420

GTCCTGATGT ACGTGCTCTG CCCCATCCTC TGGAGCCCCT GCAGACTAGT TCCTGTGACC    3480

CAGTGACATA CTGTTTGGTG TCTGCGCGTG CCCAGGTTGT CCTGCCACTT GCACTGTGCT    3540

TGCTCCTAAG CAGGAGGGGA AGGAACCATG TCCTGGAAGG AGAGCATTGG AAGAAGTGAT    3600

GAAGAGGTGA AGTGAACACA CATTCTTAAG GCAATAAAAC CGGGGGGTGT ATATTATCTT    3660

CTGGTGCATG TTCTTCTCTG GAAAATACGG TAGCTCGTAA CTGCATCCCT AGTCTGATAT    3720

TCAAACACAC AGTATTTGTG AATAAGCTGA TCCCGTCACC CAACATGGAG TCTGTGTTCA    3780

CCTACCCATG TGTCTCATTG CCAGTGGTCG TCCTTGGGGG CTCAGCTGAG ACTCTCAGCT    3840

TCTGTCACCT TGCTGTCCTG TCTTGTGGCA GCAGCACGTT GCCATCCATC ACCAGAATTA    3900

GTCCTCACAG CCTAGGACCA GTTTTGTACC AAACTCATCT GATGTTTTGA TGCCATTTGT    3960

CAAAAGTAAG GTTAATTCAT TAAAAGTTTT ATGTACTTTG AAAAAAAA                 4008
```

(2) INFORMATION FOR SEQ ID NO:4:

(i) SEQUENCE CHARACTERISTICS:
        (A) LENGTH: 1090 amino acids
        (B) TYPE: amino acid
        (C) STRANDEDNESS:
        (D) TOPOLOGY: linear (xi) SEQUENCE DESCRIPTION: SEQ ID NO:4:

```
Met Arg Arg Arg Arg Tyr Leu Arg Asp Arg Ala Glu Ala Ala Ala
1               5                   10                  15

Ala Ala Ala Gly Gly Gly Glu Gly Leu Gln Arg Ser Arg Asp Trp Leu
            20                  25                  30

Tyr Glu Ser Tyr Tyr Cys Met Ser Gln Gln His Pro Leu Ile Val Phe
            35                  40                  45

Leu Leu Leu Ile Val Met Gly Ala Cys Leu Ala Leu Ala Val Phe
    50                  55                  60

Phe Ala Leu Gly Leu Glu Val Glu Asp His Val Ala Phe Leu Ile Thr
65                  70                  75                  80

Val Pro Thr Ala Leu Ala Ile Phe Phe Ala Ile Phe Ile Leu Val Cys
                85                  90                  95

Ile Glu Ser Val Phe Lys Lys Leu Leu Arg Val Phe Ser Leu Val Ile
                100                 105                 110
```

-continued

```
Trp Ile Cys Leu Val Ala Met Gly Tyr Leu Phe Met Cys Phe Gly Gly
        115                 120                 125

Thr Val Ser Ala Trp Asp Gln Val Ser Phe Leu Phe Ile Ile Phe
130                 135                 140

Val Val Tyr Thr Met Leu Pro Phe Asn Met Arg Asp Ala Ile Ile Ala
145                 150                 155                 160

Ser Ile Leu Thr Ser Ser His Thr Ile Val Leu Ser Val Tyr Leu
            165                 170                 175

Ser Ala Thr Pro Gly Ala Lys Glu His Leu Phe Trp Gln Ile Leu Ala
            180                 185                 190

Asn Val Ile Ile Phe Ile Cys Gly Asn Leu Ala Gly Ala Tyr His Lys
            195                 200                 205

His Leu Met Glu Leu Ala Leu Gln Gln Thr Tyr Arg Asp Thr Cys Asn
    210                 215                 220

Cys Ile Lys Ser Arg Ile Lys Leu Glu Phe Glu Lys Arg Gln Gln Glu
225                 230                 235                 240

Arg Leu Leu Leu Ser Leu Leu Pro Ala His Ile Ala Met Glu Met Lys
                245                 250                 255

Ala Glu Ile Ile Gln Arg Leu Gln Gly Pro Lys Ala Gly Gln Met Glu
                260                 265                 270

Asn Thr Asn Asn Phe His Asn Leu Tyr Val Lys Arg His Thr Asn Val
            275                 280                 285

Ser Ile Leu Tyr Ala Asp Ile Val Gly Phe Thr Arg Leu Ala Ser Asp
    290                 295                 300

Cys Ser Pro Gly Glu Leu Val His Met Leu Asn Glu Leu Phe Gly Lys
305                 310                 315                 320

Phe Asp Gln Ile Ala Lys Glu Asn Glu Cys Met Arg Ile Lys Ile Leu
                325                 330                 335

Gly Asp Cys Tyr Tyr Cys Val Ser Gly Leu Pro Ile Ser Leu Pro Asn
                340                 345                 350

His Ala Lys Asn Cys Val Lys Met Gly Leu Asp Met Cys Glu Ala Ile
            355                 360                 365

Lys Lys Val Arg Asp Ala Thr Gly Val Asp Ile Asn Met Arg Val Gly
    370                 375                 380

Val His Ser Gly Asn Val Leu Cys Gly Val Ile Gly Leu Gln Lys Trp
385                 390                 395                 400

Gln Tyr Asp Val Trp Ser His Asp Val Thr Leu Ala Asn His Met Glu
                405                 410                 415

Ala Gly Gly Val Pro Gly Arg Val His Ile Ser Ser Val Thr Leu Glu
            420                 425                 430

His Leu Asn Gly Ala Tyr Lys Val Glu Glu Gly Asp Gly Glu Ile Arg
    435                 440                 445

Asp Pro Tyr Leu Lys Gln His Leu Val Lys Thr Tyr Phe Val Ile Asn
450                 455                 460

Pro Lys Gly Glu Arg Arg Ser Pro Gln His Leu Phe Arg Pro Arg His
465                 470                 475                 480

Thr Leu Asp Gly Ala Lys Met Arg Ala Ser Val Arg Met Thr Arg Tyr
                485                 490                 495

Leu Glu Ser Trp Gly Ala Ala Lys Pro Phe Ala His Leu His His Arg
                500                 505                 510

Asp Ser Met Thr Thr Glu Asn Gly Lys Ile Ser Thr Thr Asp Val Pro
            515                 520                 525

Met Gly Gln His Asn Phe Gln Asn Arg Thr Leu Arg Thr Lys Ser Gln
```

-continued

```
            530                 535                 540
Lys Lys Arg Phe Glu Glu Leu Asn Glu Arg Met Ile Gln Ala Ile
545                 550                 555                 560

Asp Gly Ile Asn Ala Gln Lys Gln Trp Leu Lys Ser Glu Asp Ile Gln
                565                 570                 575

Arg Ile Ser Leu Leu Phe Tyr Asn Lys Asn Ile Glu Lys Glu Tyr Arg
                580                 585                 590

Ala Thr Ala Leu Pro Ala Phe Lys Tyr Tyr Val Thr Cys Ala Cys Leu
                595                 600                 605

Ile Phe Leu Cys Ile Phe Ile Val Gln Ile Leu Val Leu Pro Lys Thr
                610                 615                 620

Ser Ile Leu Gly Phe Ser Phe Gly Ala Ala Phe Leu Ser Leu Ile Phe
625                 630                 635                 640

Ile Leu Phe Val Cys Phe Ala Gly Gln Leu Leu Gln Cys Ser Lys Lys
                645                 650                 655

Ala Ser Thr Ser Leu Met Trp Leu Leu Lys Ser Ser Gly Ile Ile Ala
                660                 665                 670

Asn Arg Pro Trp Pro Arg Ile Ser Leu Thr Ile Val Thr Thr Ala Ile
                675                 680                 685

Ile Leu Thr Met Ala Val Phe Asn Met Phe Phe Leu Ser Asn Ser Glu
                690                 695                 700

Glu Thr Thr Leu Pro Thr Ala Asn Thr Ser Asn Ala Asn Val Ser Val
705                 710                 715                 720

Pro Asp Asn Gln Ala Ser Ile Leu His Ala Arg Asn Leu Phe Phe Leu
                725                 730                 735

Pro Tyr Phe Ile Tyr Ser Cys Ile Leu Gly Leu Ile Ser Cys Ser Val
                740                 745                 750

Phe Leu Arg Val Asn Tyr Glu Leu Lys Met Leu Ile Met Met Val Ala
                755                 760                 765

Leu Val Gly Tyr Asn Thr Ile Leu Leu His Thr His Ala His Val Leu
770                 775                 780

Asp Ala Tyr Ser Gln Val Leu Phe Gln Arg Pro Gly Ile Trp Lys Asp
785                 790                 795                 800

Leu Lys Thr Met Gly Ser Val Ser Leu Ser Ile Phe Phe Ile Thr Leu
                805                 810                 815

Leu Val Leu Gly Arg Gln Ser Glu Tyr Tyr Cys Arg Leu Asp Phe Leu
                820                 825                 830

Trp Lys Asn Lys Phe Lys Lys Glu Arg Glu Glu Ile Glu Thr Met Glu
                835                 840                 845

Asn Leu Asn Arg Val Leu Leu Glu Asn Val Leu Pro Ala His Val Ala
850                 855                 860

Glu His Phe Leu Ala Arg Ser Leu Lys Asn Glu Glu Leu Tyr His Gln
865                 870                 875                 880

Ser Tyr Asp Cys Val Cys Val Met Phe Ala Ser Ile Pro Asp Phe Lys
                885                 890                 895

Glu Phe Tyr Thr Glu Ser Asp Val Asn Lys Glu Gly Leu Glu Cys Leu
                900                 905                 910

Arg Leu Leu Asn Glu Ile Ile Ala Asp Phe Asp Asp Leu Leu Ser Lys
                915                 920                 925

Pro Lys Phe Ser Gly Val Glu Lys Ile Lys Thr Ile Gly Ser Thr Tyr
                930                 935                 940

Met Ala Ala Thr Gly Leu Ser Ala Ile Pro Ser Gln Glu His Ala Gln
945                 950                 955                 960
```

```
Glu Pro Glu Arg Gln Tyr Met His Ile Gly Thr Met Val Glu Phe Ala
                965                 970                 975

Tyr Ala Leu Val Gly Lys Leu Asp Ala Ile Asn Lys His Ser Phe Asn
            980                 985                 990

Asp Phe Lys Leu Arg Val Gly Ile Asn His Gly Pro Val Ile Ala Gly
        995                 1000                1005

Val Ile Gly Ala Gln Lys Pro Gln Tyr Asp Ile Trp Gly Asn Thr Val
    1010                1015                1020

Asn Val Ala Ser Arg Met Asp Ser Thr Gly Val Leu Asp Lys Ile Gln
1025                1030                1035                1040

Val Thr Glu Glu Thr Ser Leu Ile Leu Gln Thr Leu Gly Tyr Thr Cys
                1045                1050                1055

Thr Cys Arg Gly Ile Ile Asn Val Lys Gly Lys Gly Asp Leu Lys Thr
            1060                1065                1070

Tyr Phe Val Asn Thr Glu Met Ser Arg Ser Leu Ser Gln Ser Asn Leu
        1075                1080                1085

Ala Ser
    1090

(2) INFORMATION FOR SEQ ID NO:5:

(i) SEQUENCE CHARACTERISTICS:
        (A) LENGTH: 4533 base pairs
        (B) TYPE: nucleic acid
        (C) STRANDEDNESS: single
        (D) TOPOLOGY: linear (xi) SEQUENCE DESCRIPTION: SEQ ID NO:5:

TGAACCACAG CCCCGCGCCT CTACCGGCCC GACCCGGGGC CTGACCGCAA GGGGACCCGC      60

GCACAGGCTC CGGGCGGAGG AGCTGGCGCG GCGGCACTGC GGGAAGCAGC CTGCGGCTCG    120

CTGAAGCCCG CTTGGCCCGG CTCCGCAGCC CTGGTCCGGA GCGCGCGGCT CCCGAGTTCC    180

CGCACAGTTG CAGATGATCG GTGCCACCTG TGTCCTGGGA ACCCACTAAA CATTCCAGCT    240

CCAGTTGGAC GCCCTTCACC CACAACCAAG GGGAGCCTCC CCGCCTTCCC AGGTCTTAAC    300

GAAGCCCTGG TGAAGTGGCT TGACCTGGAC TTCTCCCTCC CTCATTAGAA GCAGCCACCA    360

GTCAACATGA CCGAGGACCA GGGCTTCTCG GATCCCGAGT ACTCGGCAGA GTACTCAGCC    420

GAGTACTCAG TCAGCTTGCC CTCTGACCCC GACCGCGGGG TCGGCCGGAC CCATGAAATT    480

TCTGTGCGGA ACTCTGGGTC CTGCCTGTGC CTGCCTCGCT TTATGCGGCT GACCTTCGTG    540

CCTGAGTCCT TGGAGAACCT CTACCAGACC TACTTTAAAA GGCAGCGCCA TGAGACACTG    600

CTGGTGCTGG TGGTCTTTGC GGCCCTCTTT GACTGCTACG TGGTAGTGAT GTGCGCGGTG    660

GTCTTTTCCA GCGACAAGCT GGCGCCCCTC ATGGTGGCAG GCGTCGGTCT GGTGTTGGAC    720

ATCATCCTTT TCGTGCTCTG CAAAAAGGGG CTGCTCCCGG ATCGAGTGAG CCGCAAAGTG    780

GTACCCTACC TGCTGTGGCT GCTCATCACA GCCCAGATCT TCTCCTACCT GGGCCTGAAC    840

TTTTCGCGTG CCCACGCAGC CAGTGACACT GTGGGTTGGA AGGCCTTCTT TGTCTTCTCC    900

TTCTTCATAA CGCTGCCACT CAGCCTCAGC CCCATCGTGA TCATCTCCGT GGTCTCCTGT    960

GTTGTGCATA CGCTTGTCTT GGGGGTCACG GTGGCCCAGC AGCAGCAAGA CGAGCTAGAA   1020

GGGATGCAGC TGCTGAGGGA GATCCTGGCT AACGTCTTCC TCTACCTGTG CGCCATCATC   1080

GTGGGCATCA TGTCCTACTA CATGGCAGAC CGTAAGCACC GAAAGGCCTT CCTGGAGGCC   1140

CGCCAGTCGC TGGAGGTGAA GATGAATCTG GAGGAGCAGA GCCAGCAGCA GGAAAACCTT   1200
```

```
ATGCTTTCCA TCCTGCCAAA GCATGTGGCT GACGAGATGT TGAAGGACAT GAAGAAAGAT    1260

GAGAGTCAGA AGGACCAGCA GCAGTTCAAC ACCATGTACA TGTACCGCCA TGAGAATGTC    1320

AGCATCCTGT TTGCAGATAT TGTGGGCTTT ACCCAGCTGT CCTCTGCTTG CAGTGCCCAG    1380

GAGCTCGTGA AGCTACTCAA CGAGCTCTTT GCCCGCTTTG ACAAGCTGGC GGCCAAATAC    1440

CACCAGCTGA GGATCAAGAT CCTAGGCGAC TGTTACTACT GCATCTGCGG CCTGCCTGAC    1500

TACCGGGAGG ACCACGCCGT GTGCTCCATC CTGATGGGGC TTGCCATGGT AGAGGCCATC    1560

TCGTACGTGC GGGAGAAGAC CAAGACCGGA GTGGACATGC GTGTGGGGGT GCACACAGGC    1620

ACTGTGCTAG GTGGCGTCCT GGGCCAGAAG CGCTGGCAGT ATGATGTATG GTCTACCGAT    1680

GTCACTGTGG CAAACAAGAT GGAGGCTGGC GGCATCCCAG GGCGCGTGCA CATTTCCCAG    1740

AGCACCATGG ACTGCCTGAA AGGGGAGTTC GATGTCGAAC CTGGTGATGG TGGCAGTCGC    1800

TGCGACTACC TAGATGAGAA GGGCATCGAA ACCTACCTCA TCATTGCCTC CAAGCCAGAG    1860

GTGAAGAAGA CAGCTCAAAA TGGCCTCAAC GGCTCGGCCC TGCCAAACGG AGCACCGGCA    1920

TCCAAGCCCA GCTCCCCTGC CCTTATTGAG ACCAAGGAGC CCAATGGGAG TGCCCATGCC    1980

AGCGGCTCCA CATCAGAGGA GGCTGAAGAA CAGGAGGCCC AGGCTGACAA CCCCTCGTTC    2040

CCCAACCCCC GCCGCAGGCT GCGCCTCCAG GACCTGGCAG ACCGTGTGGT GGACGCCTCT    2100

GAGGATGAGC ACGAACTGAA CCAGCTTCTT AACGAGGCCC TGCTGGAGCG GGAGTCCGCC    2160

CAGGTGGTAA AGAAGAGAAA CACATTCCTC CTAACGATGA GGTTCATGGA CCCAGAGATG    2220

GAAACACGCT ACTCGGTGGA GAAGGAGAAG CAGAGTGGGG CTGCCTTCAG CTGTTCCTGT    2280

GTGGTCCTTT TCTGCACGGC CATGGTGGAG ATACTTATCG ACCCCTGGTT GATGACAAAC    2340

TACGTGACCT TCGTGGTTGG AGAGGTTCTG CTCTTGATCC TGACCATCTG TTCGATGGCT    2400

GCCATCTTCC CCAGGGCATT TCCTAAGAAG CTCGTGGCCT TCTCATCTTG GATTGACCGG    2460

ACCCGCTGGG CCAGAAATAC CTGGGCCATG TTAGCCATCT TCATTCTGGT TATGGCCAAT    2520

GTTGTGGACA TGCTGAGCTG TCTCCAGTAC TACATGGGAC CTTACAACGT GACAACCGGG    2580

ATAGAGCTGG ACGGTGGCTG TATGGAGAAC CCCAAGTACT ACAACTATGT TGCTGTGCTG    2640

TCCCTCATCG CCACCATCAT GCTGGTGCAG GTCAGCCACA TGGTGAAGCT GACACTCATG    2700

CTGCTCGTCA CAGGCGCCGT GACTGCCATC AACCTGTATG CCTGGTGTCC TGTCTTTGAT    2760

GAATACGACC ACAAACGCTT TCAGGAAAAG GACTCTCCTA TGGTGGCCTT AGAGAAGATG    2820

CAGGTACTTT CCACCCCTGG GCTCAATGGC ACTGACAGCA GGCTGCCCCT GGTGCCTTCC    2880

AAGTACTCGA TGACTGTGAT GATGTTCGTT ATGATGCTGA GCTTTACTA CTTCTCACGC    2940

CACGTGGAGA AACTGGCCCG GACACTGTTC TTGTGGAAGA TTGAGGTCCA TGACCAGAAA    3000

GAACGTGTGT ACGAGATGCG CCGGTGGAAC GAGGCCTTGG TCACCAACAT GTTGCCAGAG    3060

CATGTTGCAC GCCATTTCCT GGGCTCCAAG AAGAGAGATG AGGAGCTGTA CAGCCAGTCT    3120

TATGACGAGA TTGGAGTCAT GTTTGCCTCC TTGCCCAACT TTGCCGACTT CTACACTGAG    3180

GAGAGCATCA ATAATGGTGG CATCGAGTGT CTACGCTTCC TCAATGAGAT CATCTCTGAT    3240

TTTGACTCTC TCCTGGACAA TCCCAAATTC CGGGTCATCA CCAAGATCAA AACCATCGGC    3300

AGCACCTATA TGGCAGCTTC TGGAGTCACA CCAGATGTCA ACACCAATGG CTTTACAAGC    3360

TCCAGCAAGG AGGAAAAGTC AGACAAGGAG CGCTGGCAGC ACCTGGCTGA CCTGGCAGAC    3420

TTTGCACTAG CCATGAAGGA CACGCTTACA AACATCAACA ACCAGTCATT CAACAACTTC    3480

ATGCTGCGCA TAGGCATGAA CAAAGGAGGA GTTCTGGCTG GAGTCATTGG AGCCCGGAAG    3540

CCACACTATG ACATCTGGGG GAACACGGTC AATGTGGCCA GCAGGATGGA ATCCACAGGG    3600
```

-continued

```
GTCATGGGCA ATATCCAGGT GGTAGAAGAG ACACAGGTCA TCCTTCGAGA GTATGGCTTC       3660

CGCTTTGTGA GGCGAGGACC CATCTTTGTG AAGGGCAAAG GGGAGCTTCT GACCTTTTTC       3720

TTAAAGGGGC GGGACAGGCC AGCTGCCTTC CCCAATGGCT CCTCTGTTAC ACTGCCCCAC       3780

CAAGTGGTGG ACAACCCCTG AACAGCCCTG GCTCCACAGC GGTCCACACT GGAAGGGAGA       3840

CATTTTGGAA GCAGAGAAAA GCTTTGGGAA AGGGCAAACG ACCGAGTCCC GGGGTTCCCA       3900

ACTGTTGAAG TGCACATTCC CATAGACTTT AGGTTTCAGA TTTCCTCCAG CCTCCCTGTG       3960

TGGCTGTGAG CTCTGAGCGT GGCTATTCCT ACTCCTCAGT GTGCCTGTAG CTTCCCCAAA       4020

GCAGGGGTCT AGGCATAGTA CTGGAGCAGC CTTTCCAGAG CCTTTGTTCC AGCTCAGCCC       4080

TTCACCCCTA GAGAGGCCAC AGCCACTGTG AGCAGGATGC CAGCAGATGT GGGATGAAGC       4140

TGCCTGTGCT GCAGGGTGGG GGCACAGGCT GGGCTCAGGG CCGAGAAGGC TCGGCGCCTG       4200

GCTGCGCCTC CTGTCAGTTA AGTCAATGGC CCTTACCCGA TGTTCCTGAT AATCTTGAAA       4260

GGTTCTTCTG GAACCCCCGT GTCACCTTAG TCACGAGAGC GAAAAGTGCA ATATTTCCTT       4320

TCACCTGGTT GGGAAGGGGG GTTATTTCTG AAAGAAAAAA ATATATAAAC AGATCTTCTA       4380

CATTTATATT TTTAACCTGT TCAAAAAACA ACTTTCCAAT ATTGCCTTGT CTTCTGAGCT       4440

CTTGCTACAG TCGCCTTTGC TACTGCTTTA ACAGAGAATC TGCAGGTGTT GATAAAGAAC       4500

AGGACTGTTT TATTAAAAGC TTTACTCAAC TTG                                   4533
```

(2) INFORMATION FOR SEQ ID NO:6:

(i) SEQUENCE CHARACTERISTICS:
        (A) LENGTH: 1144 amino acids
        (B) TYPE: amino acid
        (C) STRANDEDNESS:
        (D) TOPOLOGY: linear (xi) SEQUENCE DESCRIPTION: SEQ ID NO:6:

```
Met Thr Glu Asp Gln Gly Phe Ser Asp Pro Glu Tyr Ser Ala Glu Tyr
1               5                   10                  15

Ser Ala Glu Tyr Ser Val Ser Leu Pro Ser Asp Pro Asp Arg Gly Val
            20                  25                  30

Gly Arg Thr His Glu Ile Ser Val Arg Asn Ser Gly Ser Cys Leu Cys
        35                  40                  45

Leu Pro Arg Phe Met Arg Leu Thr Phe Val Pro Glu Ser Leu Glu Asn
50                  55                  60

Leu Tyr Gln Thr Tyr Phe Lys Arg Gln Arg His Glu Thr Leu Leu Val
65                  70                  75                  80

Leu Val Val Phe Ala Ala Leu Phe Asp Cys Tyr Val Val Met Cys
                85                  90                  95

Ala Val Val Phe Ser Ser Asp Lys Leu Ala Pro Leu Met Val Ala Gly
            100                 105                 110

Val Gly Leu Val Leu Asp Ile Ile Leu Phe Val Leu Cys Lys Lys Gly
        115                 120                 125

Leu Leu Pro Asp Arg Val Ser Arg Lys Val Val Pro Tyr Leu Leu Trp
    130                 135                 140

Leu Leu Ile Thr Ala Gln Ile Phe Ser Tyr Leu Gly Leu Asn Phe Ser
145                 150                 155                 160

Arg Ala His Ala Ala Ser Asp Thr Val Gly Trp Gln Ala Phe Phe Val
                165                 170                 175

Phe Ser Phe Phe Ile Thr Leu Pro Leu Ser Leu Ser Pro Ile Val Ile
            180                 185                 190
```

-continued

```
Ile Ser Val Val Ser Cys Val His Thr Leu Val Leu Gly Val Thr
        195                 200                 205
Val Ala Gln Gln Gln Asp Glu Leu Glu Gly Met Gln Leu Leu Arg
210                     215                 220
Glu Ile Leu Ala Asn Val Phe Leu Tyr Leu Cys Ala Ile Ile Val Gly
225                 230                 235                 240
Ile Met Ser Tyr Tyr Met Ala Asp Arg Lys His Arg Lys Ala Phe Leu
                245                 250                 255
Glu Ala Arg Gln Ser Leu Glu Val Lys Met Asn Leu Glu Glu Gln Ser
            260                 265                 270
Gln Gln Gln Glu Asn Leu Met Leu Ser Ile Leu Pro Lys His Val Ala
        275                 280                 285
Asp Glu Met Leu Lys Asp Met Lys Lys Asp Glu Ser Gln Lys Asp Gln
290                 295                 300
Gln Gln Phe Asn Thr Met Tyr Met Tyr Arg His Glu Asn Val Ser Ile
305                 310                 315                 320
Leu Phe Ala Asp Ile Val Gly Phe Thr Gln Leu Ser Ser Ala Cys Ser
                325                 330                 335
Ala Gln Glu Leu Val Lys Leu Leu Asn Glu Leu Phe Ala Arg Phe Asp
            340                 345                 350
Lys Leu Ala Ala Lys Tyr His Gln Leu Arg Ile Lys Ile Leu Gly Asp
        355                 360                 365
Cys Tyr Tyr Cys Ile Cys Gly Leu Pro Asp Tyr Arg Glu Asp His Ala
370                 375                 380
Val Cys Ser Ile Leu Met Gly Leu Ala Met Val Glu Ala Ile Ser Tyr
385                 390                 395                 400
Val Arg Glu Lys Thr Lys Thr Gly Val Asp Met Arg Val Gly Val His
                405                 410                 415
Thr Gly Thr Val Leu Gly Gly Val Leu Gly Gln Lys Arg Trp Gln Tyr
            420                 425                 430
Asp Val Trp Ser Thr Asp Val Thr Val Ala Asn Lys Met Glu Ala Gly
        435                 440                 445
Gly Ile Pro Gly Arg Val His Ile Ser Gln Ser Thr Met Asp Cys Leu
450                 455                 460
Lys Gly Glu Phe Asp Val Glu Pro Gly Asp Gly Gly Ser Arg Cys Asp
465                 470                 475                 480
Tyr Leu Asp Glu Lys Gly Ile Glu Thr Tyr Leu Ile Ile Ala Ser Lys
                485                 490                 495
Pro Glu Val Lys Lys Thr Ala Gln Asn Gly Leu Asn Gly Ser Ala Leu
            500                 505                 510
Pro Asn Gly Ala Pro Ala Ser Lys Pro Ser Ser Pro Ala Leu Ile Glu
        515                 520                 525
Thr Lys Glu Pro Asn Gly Ser Ala His Ala Ser Gly Ser Thr Ser Glu
530                 535                 540
Glu Ala Glu Glu Gln Glu Ala Gln Ala Asp Asn Pro Ser Phe Pro Asn
545                 550                 555                 560
Pro Arg Arg Arg Leu Arg Leu Gln Asp Leu Ala Asp Arg Val Val Asp
                565                 570                 575
Ala Ser Glu Asp Glu His Glu Leu Asn Gln Leu Leu Asn Glu Ala Leu
            580                 585                 590
Leu Glu Arg Glu Ser Ala Gln Val Val Lys Lys Arg Asn Thr Phe Leu
        595                 600                 605
```

```
Leu Thr Met Arg Phe Met Asp Pro Glu Met Glu Thr Arg Tyr Ser Val
    610                 615                 620

Glu Lys Glu Lys Gln Ser Gly Ala Ala Phe Ser Cys Ser Cys Val Val
625                 630                 635                 640

Leu Phe Cys Thr Ala Met Val Glu Ile Leu Ile Asp Pro Trp Leu Met
                645                 650                 655

Thr Asn Tyr Val Thr Phe Val Val Gly Glu Val Leu Leu Leu Ile Leu
            660                 665                 670

Thr Ile Cys Ser Met Ala Ala Ile Phe Pro Arg Ala Phe Pro Lys Lys
            675                 680                 685

Leu Val Ala Phe Ser Ser Trp Ile Asp Arg Thr Arg Trp Ala Arg Asn
690                 695                 700

Thr Trp Ala Met Leu Ala Ile Phe Ile Leu Val Met Ala Asn Val Val
705                 710                 715                 720

Asp Met Leu Ser Cys Leu Gln Tyr Tyr Met Gly Pro Tyr Asn Val Thr
                725                 730                 735

Thr Gly Ile Glu Leu Asp Gly Gly Cys Met Glu Asn Pro Lys Tyr Tyr
            740                 745                 750

Asn Tyr Val Ala Val Leu Ser Leu Ile Ala Thr Ile Met Leu Val Gln
            755                 760                 765

Val Ser His Met Val Lys Leu Thr Leu Met Leu Leu Val Thr Gly Ala
770                 775                 780

Val Thr Ala Ile Asn Leu Tyr Ala Trp Cys Pro Val Phe Asp Glu Tyr
785                 790                 795                 800

Asp His Lys Arg Phe Gln Glu Lys Asp Ser Pro Met Val Ala Leu Glu
                805                 810                 815

Lys Met Gln Val Leu Ser Thr Pro Gly Leu Asn Gly Thr Asp Ser Arg
            820                 825                 830

Leu Pro Leu Val Pro Ser Lys Tyr Ser Met Thr Val Met Met Phe Val
            835                 840                 845

Met Met Leu Ser Phe Tyr Tyr Phe Ser Arg His Val Glu Lys Leu Ala
850                 855                 860

Arg Thr Leu Phe Leu Trp Lys Ile Glu Val His Asp Gln Lys Glu Arg
865                 870                 875                 880

Val Tyr Glu Met Arg Arg Trp Asn Glu Ala Leu Val Thr Asn Met Leu
                885                 890                 895

Pro Glu His Val Ala Arg His Phe Leu Gly Ser Lys Lys Arg Asp Glu
            900                 905                 910

Glu Leu Tyr Ser Gln Ser Tyr Asp Glu Ile Gly Val Met Phe Ala Ser
            915                 920                 925

Leu Pro Asn Phe Ala Asp Phe Tyr Thr Glu Glu Ser Ile Asn Asn Gly
930                 935                 940

Gly Ile Glu Cys Leu Arg Phe Leu Asn Glu Ile Ile Ser Asp Phe Asp
945                 950                 955                 960

Ser Leu Leu Asp Asn Pro Lys Phe Arg Val Ile Thr Lys Ile Lys Thr
                965                 970                 975

Ile Gly Ser Thr Tyr Met Ala Ala Ser Gly Val Thr Pro Asp Val Asn
            980                 985                 990

Thr Asn Gly Phe Thr Ser Ser Lys Glu Glu Lys Ser Asp Lys Glu
            995                 1000                1005

Arg Trp Gln His Leu Ala Asp Leu Ala Asp Phe Ala Leu Ala Met Lys
    1010                1015                1020

Asp Thr Leu Thr Asn Ile Asn Asn Gln Ser Phe Asn Asn Phe Met Leu
```

```
                 1025           1030            1035           1040
Arg Ile Gly Met Asn Lys Gly Val Leu Ala Gly Val Ile Gly Ala
                         1045            1050            1055
Arg Lys Pro His Tyr Asp Ile Trp Gly Asn Thr Val Asn Val Ala Ser
                 1060            1065            1070
Arg Met Glu Ser Thr Gly Val Met Gly Asn Ile Gln Val Val Glu Glu
             1075            1080            1085
Thr Gln Val Ile Leu Arg Glu Tyr Gly Phe Arg Phe Val Arg Arg Gly
         1090            1095            1100
Pro Ile Phe Val Lys Gly Lys Gly Glu Leu Leu Thr Phe Phe Leu Lys
1105            1110            1115            1120
Gly Arg Asp Arg Pro Ala Ala Phe Pro Asn Gly Ser Ser Val Thr Leu
             1125            1130            1135
Pro His Gln Val Val Asp Asn Pro
         1140

(2) INFORMATION FOR SEQ ID NO:7:

(i) SEQUENCE CHARACTERISTICS:
          (A) LENGTH: 3357 base pairs
          (B) TYPE: nucleic acid
          (C) STRANDEDNESS: single
          (D) TOPOLOGY: linear (xi) SEQUENCE DESCRIPTION: SEQ ID NO:7:

CGGGGCAGCC AGCCTACCCA GGTTCCCTCC TGGAGCCTAG CTTTGCTACG AGAACTTCAG      60

GAGCTTAACA CAAAGCAGGC AGGGGCTCCG GGCTGGGGCG GGGGATATCA TGGCCCGCCT     120

CTTCAGTCCC CGGCCTCCTC CCAGCGAAGA TCTCTTCTAC GAGACTTACT ACAGCCTGAG     180

CCAACAGTAT CCACTGCTAA TTCTGCTTCT GGTCATTGTG CTCTGCGCGA TCGTGGCACT     240

GCCCGCCGTC GCCTGGGCCA GCGGCAGGGA GCTGACCTCA GACCCAAGCT TCCTGACAAC     300

TGTGCTGTGT GCTTTGGGTG GCTTCTCCCT GCTTTTGGGG CTCGCTTCCC GGGAGCAGCA     360

ACTGCAGCGA TGGACACGAC CTCTTTCTGG CCTCATATGG GCTGCTTTGC TGGCTCTGGG     420

CTATGGGTTT CTATTCACTG GGGGTGTGGT GAGCGCCTGG GATCAGGTGT CCTTTTTCCT     480

CTTCATCATT TTCACCGTGT ACGCCATGCT GCCCTTGGGC ATGCGGGATG CTGCTGCCGC     540

GGGGGTCATC TCATCCCTCT CACACCTGCT GGTCCTTGGA CTGTACCTTG GTGGCGGCC     600

TGAGTCGCAG AGGGATCTGC TACCACAGTT GGCAGCGAAT GCGGTGTTGT TCCTGTGTGG     660

GAACGTGGTG GGAGCATACC ACAAGGCACT GATGGAGCGA GCATTGCGCG CCACGTTCCG     720

GGAGGCTCTT AGCTCCCTGC ATTCACGCCG GAGGTTGGAC ACTGAGAAAA AGCACCAGGA     780

GCACCTCCTC TTGTCTATCC TTCCTGCCTA CCTGGCCCGA GAGATGAAGG CAGAGATCAT     840

GGCTCGGCTG CAGGCTGGAC AGAGCTCACG GCCAGAGAAC ACAAACAACT TTCACAGCCT     900

GTATGTCAAG AGGCACCAAG GAGTGAGTGT GCTGTATGCT GACATCGTGG GCTTCACACG     960

GCTGGCCAGT GAGTGTTCCC CTAAGGAGCT GGTGCTAATG CTCAATGAAC TCTTCGGCAA    1020

ATTCGACCAA ATTGCAAAGG AGCACGAATG CATGCGGATC AAGATCCTGG GAGACTGTTA    1080

CTACTGTGTA TCCGGGCTGC CCCTCTCTCT GCCTGACCAC GCCATCAATT GCGTGCGCAT    1140

GGGACTGGAC ATGTGCCGGG CCATCAGGAA ACTTCGGGTA GCCACCGGTG TGGATATCAA    1200

CATGCGTGTC GGTGTGCACT CAGGCAGCGT CCTCTGTGGA GTCATCGGGC TACAGAAGTG    1260

GCAGTATGAT GTCTGGTCCC ATGATGTCAC ATTGGCCAAC CATATGGAAG CAGGCGGCGT    1320

TCCAGGACGA GTGCACATCA CAGGGGCCAC GCTGGCCCTG CTGGCAGGAG CTTATGCTGT    1380
```

```
GGAGAGAGCA GACATGGAGC ATCGAGACCC ATACCTTCGG GAGCTAGGGG AACCCACATA    1440

CCTGGTCATT GATCCTTGGG CTGAGGAGGA AGACGAGAAG GGCACCGAGA GAGGATTGCT    1500

GTCTTCTCTA GAGGGCACA CGATGCGTCC GTCACTACTG ATGACTCGTT ATCTGGAGTC    1560

TTGGGGTGCA GCCAAGCCTT TCGCCCACCT AAGCCACGTC GACAGTCCTG CATCCACATC    1620

CACTCCACTC CCGGAGAAAG CCTTCAGCCC CCAGTGGAGC CTGGACCGGA GTCGCACCCC    1680

CCGCGGGCTA CACGATGAAC TGGACACTGG AGATGCCAAG TTCTTCCAGG TCATCGAACA    1740

ACTCAACTCT CAAAAACAGT GGAAACAGTC GAAGGACTTC AACCTCCTGA CGCTCTACTT    1800

CAGAGAGAAG GAGATGGAGA AACAGTATCG GCTGTCTGCG CTCCCCGCCT TCAAATACTA    1860

CGCAGCCTGC ACCTTCCTGG TTTTTCTGTC CAACTTCACA ATCCAAATGC TGGTGACAAC    1920

CAGGCCCCCA GCTCTGGCCA CCACCTACAG CATCACCTTC CTTCTCTTCC TTCTCCTCCT    1980

CTTCGTCTGC TTCTCAGAGC ACCTGACGAA GTGCGTCCAG AAAGGCCCCA AGATGTTGCA    2040

CTGGCTGCCT GCGCTGTCTG TCCTGGTGGC CACACGGCCG GGATTGCGAG TAGCCCTGGG    2100

CACAGCCACC ATCCTCCTGG TGTTCACTAT GGCCGTCGTC AGCCTGCTCT TCTTACCAGT    2160

GTCGTCAGAC TGCCCTTTCC TGGCTCCCAA TGTGTCGTCA GTGGCTTTTA ATACTTCCTG    2220

GGAGCTGCCA GCATCCCTGC CTCTCATCAG CATCCCATAC TCCATGCATT GTTGCGTGCT    2280

GGGTTTCCTT TCCTGCTCCC TTTTTCTGCA CATGAGCTTC GAACTGAAGC TGCTTCTGCT    2340

TCTGCTGTGG CTGGTGGCAT CTTGTTCCCT ATTTCTGCAC TCCCACGCCT GGCTGTCCGA    2400

CTGCCTCATT GCCCGCCTTT ATCAAGGCTC ATTGGGCTCC AGGCCGGGGG TACTGAAGGA    2460

ACCGAAACTG ATGGGAGCTA TCTACTTCTT CATCTTCTTC TTCACACTCC TCGTCCTGGC    2520

TCGGCAGAAT GAGTATTACT GTCGCCTGGA CTTCCTATGG AAAAAGAAAC TGAGGCAGGA    2580

GCGAGAGGAA ACTGAGACAA TGGAGAATGT ACTCCCTGCA CACGTGGCGC CCAGCTCAT    2640

CGGCCAGAAC CGGCGCAATG AGGACCTCTA CCATCAGTCG TACGAATGTG TTTGTGTCCT    2700

CTTTGCATCC ATCCCAGACT TTAAGGAATT CTACTCGGAA TCCAACATCA ACCATGAGGG    2760

GCTAGAGTGT CTGCGGCTGC TCAATGAGAT CATTGCCGAC TTTGATGAGC TGCTCTCCAA    2820

GCCAAAGTTC AGTGGAGTAG AGAAGATCAA AACTATCGGC AGCACCTACA TGGCGGCCAC    2880

AGGCCTAAAT GCCACCCCTG GCAGGACAC ACAACAGGAC GCTGAGAGAA GCTGCAGCCA    2940

TCTGGGCACC ATGGTGGAAT TTGCAGTGGC CCTGGGGTCT AAGCTGGGTG TCATCAATAA    3000

GCACTCGTTC AACAACTTCC GCCTGCGTGT GGGGTTAAAC CATGGACCAG TCGTAGCAGG    3060

GGTGATTGGG GCACAGAAGC CACAATATGA CATCTGGGGG AATACAGTGA ACGTGGCCAG    3120

CCGCATGGAG AGCACAGGAG TTCTCGGCAA GATCCAAGTG ACCGAGGAGA CAGCTAGGGC    3180

CCTGCAATCC CTGGGTTACA CATGCTACAG CCGAGGTGTC ATCAAGGTCA AGGGCAAAGG    3240

GCAACTCTGT ACCTACTTCC TGAACACAGA CCTGACACGA ACCGGATCTC CCTCAGCATC    3300

CTAGACACCT GAGCTCCCCT TCTCCAAGAT CCTCAATAAA ATGTCTCCAG GCATCTG      3357
```

(2) INFORMATION FOR SEQ ID NO:8:

(i) SEQUENCE CHARACTERISTICS:
        (A) LENGTH: 1064 amino acids
        (B) TYPE: amino acid
        (C) STRANDEDNESS:
        (D) TOPOLOGY: linear (xi) SEQUENCE DESCRIPTION: SEQ ID NO:8:

Met Ala Arg Leu Phe Ser Pro Arg Pro Pro Ser Glu Asp Leu Phe

-continued

```
1               5                   10                  15
Tyr Glu Thr Tyr Tyr Ser Leu Ser Gln Gln Tyr Pro Leu Leu Ile Leu
                20                  25                  30
Leu Leu Val Ile Val Leu Cys Ala Ile Val Ala Leu Pro Ala Val Ala
                35                  40                  45
Trp Ala Ser Gly Arg Glu Leu Thr Ser Asp Pro Ser Phe Leu Thr Thr
    50                  55                  60
Val Leu Cys Ala Leu Gly Gly Phe Ser Leu Leu Gly Leu Ala Ser
65                  70                  75                  80
Arg Glu Gln Gln Leu Gln Arg Trp Thr Arg Pro Leu Ser Gly Leu Ile
                85                  90                  95
Trp Ala Ala Leu Leu Ala Leu Gly Tyr Gly Phe Leu Phe Thr Gly Gly
                100                 105                 110
Val Val Ser Ala Trp Asp Gln Val Ser Phe Phe Leu Phe Ile Ile Phe
            115                 120                 125
Thr Val Tyr Ala Met Leu Pro Leu Gly Met Arg Asp Ala Ala Ala Ala
        130                 135                 140
Gly Val Ile Ser Ser Leu Ser His Leu Leu Val Leu Gly Leu Tyr Leu
145                 150                 155                 160
Gly Trp Arg Pro Glu Ser Gln Arg Asp Leu Leu Pro Gln Leu Ala Ala
                165                 170                 175
Asn Ala Val Leu Phe Leu Cys Gly Asn Val Val Gly Ala Tyr His Lys
                180                 185                 190
Ala Leu Met Glu Arg Ala Leu Arg Ala Thr Phe Arg Glu Ala Leu Ser
            195                 200                 205
Ser Leu His Ser Arg Arg Arg Leu Asp Thr Glu Lys Lys His Gln Glu
        210                 215                 220
His Leu Leu Leu Ser Ile Leu Pro Ala Tyr Leu Ala Arg Glu Met Lys
225                 230                 235                 240
Ala Glu Ile Met Ala Arg Leu Gln Ala Gly Gln Ser Ser Arg Pro Glu
                245                 250                 255
Asn Thr Asn Asn Phe His Ser Leu Tyr Val Lys Arg His Gln Gly Val
                260                 265                 270
Ser Val Leu Tyr Ala Asp Ile Val Gly Phe Thr Arg Leu Ala Ser Glu
        275                 280                 285
Cys Ser Pro Lys Glu Leu Val Leu Met Leu Asn Glu Leu Phe Gly Lys
290                 295                 300
Phe Asp Gln Ile Ala Lys Glu His Glu Cys Met Arg Ile Lys Ile Leu
305                 310                 315                 320
Gly Asp Cys Tyr Tyr Cys Val Ser Gly Leu Pro Leu Ser Leu Pro Asp
                325                 330                 335
His Ala Ile Asn Cys Val Arg Met Gly Leu Asp Met Cys Arg Ala Ile
                340                 345                 350
Arg Lys Leu Arg Val Ala Thr Gly Val Asp Ile Asn Met Arg Val Gly
            355                 360                 365
Val His Ser Gly Ser Val Leu Cys Gly Val Ile Gly Leu Gln Lys Trp
    370                 375                 380
Gln Tyr Asp Val Trp Ser His Asp Val Thr Leu Ala Asn His Met Glu
385                 390                 395                 400
Ala Gly Gly Val Pro Gly Arg Val His Ile Thr Gly Ala Thr Leu Ala
                405                 410                 415
Leu Leu Ala Gly Ala Tyr Ala Val Glu Arg Ala Asp Met Glu His Arg
                420                 425                 430
```

-continued

```
Asp Pro Tyr Leu Arg Glu Leu Gly Glu Pro Thr Tyr Leu Val Ile Asp
    435                 440                 445
Pro Trp Ala Glu Glu Asp Glu Lys Gly Thr Glu Arg Gly Leu Leu
450                 455                 460
Ser Ser Leu Glu Gly His Thr Met Arg Pro Ser Leu Leu Met Thr Arg
465                 470                 475                 480
Tyr Leu Glu Ser Trp Gly Ala Ala Lys Pro Phe Ala His Leu Ser His
                    485                 490                 495
Val Asp Ser Pro Ala Ser Thr Ser Thr Pro Leu Pro Glu Lys Ala Phe
                500                 505                 510
Ser Pro Gln Trp Ser Leu Asp Arg Ser Arg Thr Pro Arg Gly Leu His
    515                 520                 525
Asp Glu Leu Asp Thr Gly Asp Ala Lys Phe Phe Gln Val Ile Glu Gln
    530                 535                 540
Leu Asn Ser Gln Lys Gln Trp Lys Gln Ser Lys Asp Phe Asn Leu Leu
545                 550                 555                 560
Thr Leu Tyr Phe Arg Glu Lys Glu Met Glu Lys Gln Tyr Arg Leu Ser
                565                 570                 575
Ala Leu Pro Ala Phe Lys Tyr Tyr Ala Ala Cys Thr Phe Leu Val Phe
                580                 585                 590
Leu Ser Asn Phe Thr Ile Gln Met Leu Val Thr Thr Arg Pro Pro Ala
            595                 600                 605
Leu Ala Thr Thr Tyr Ser Ile Thr Phe Leu Leu Phe Leu Leu Leu Leu
        610                 615                 620
Phe Val Cys Phe Ser Glu His Leu Thr Lys Cys Val Gln Lys Gly Pro
625                 630                 635                 640
Lys Met Leu His Trp Leu Pro Ala Leu Ser Val Leu Ala Thr Arg
                645                 650                 655
Pro Gly Leu Arg Val Ala Leu Gly Thr Ala Thr Ile Leu Leu Val Phe
                660                 665                 670
Thr Met Ala Val Val Ser Leu Leu Phe Leu Pro Val Ser Ser Asp Cys
        675                 680                 685
Pro Phe Leu Ala Pro Asn Val Ser Ser Val Ala Phe Asn Thr Ser Trp
690                 695                 700
Glu Leu Pro Ala Ser Leu Pro Leu Ile Ser Ile Pro Tyr Ser Met His
705                 710                 715                 720
Cys Cys Val Leu Gly Phe Leu Ser Cys Ser Leu Phe Leu His Met Ser
                725                 730                 735
Phe Glu Leu Lys Leu Leu Leu Leu Leu Leu Trp Leu Val Ala Ser Cys
                740                 745                 750
Ser Leu Phe Leu His Ser His Ala Trp Leu Ser Asp Cys Leu Ile Ala
            755                 760                 765
Arg Leu Tyr Gln Gly Ser Leu Gly Ser Arg Pro Gly Val Leu Lys Glu
        770                 775                 780
Pro Lys Leu Met Gly Ala Ile Tyr Phe Ile Phe Phe Thr Leu
785                 790                 795                 800
Leu Val Leu Ala Arg Gln Asn Glu Tyr Tyr Cys Arg Leu Asp Phe Leu
                805                 810                 815
Trp Lys Lys Lys Leu Arg Gln Glu Arg Glu Thr Glu Thr Met Glu
                820                 825                 830
Asn Val Leu Pro Ala His Val Ala Pro Gln Leu Ile Gly Gln Asn Arg
                835                 840                 845
```

```
Arg Asn Glu Asp Leu Tyr His Gln Ser Tyr Glu Cys Val Cys Val Leu
    850                 855                 860
Phe Ala Ser Ile Pro Asp Phe Lys Glu Phe Tyr Ser Glu Ser Asn Ile
865                 870                 875                 880
Asn His Glu Gly Leu Glu Cys Leu Arg Leu Leu Asn Glu Ile Ile Ala
                885                 890                 895
Asp Phe Asp Glu Leu Leu Ser Lys Pro Lys Phe Ser Gly Val Glu Lys
            900                 905                 910
Ile Lys Thr Ile Gly Ser Thr Tyr Met Ala Ala Thr Gly Leu Asn Ala
        915                 920                 925
Thr Pro Gly Gln Asp Thr Gln Gln Asp Ala Glu Arg Ser Cys Ser His
    930                 935                 940
Leu Gly Thr Met Val Glu Phe Ala Val Ala Leu Gly Ser Lys Leu Gly
945                 950                 955                 960
Val Ile Asn Lys His Ser Phe Asn Asn Phe Arg Leu Arg Val Gly Leu
                965                 970                 975
Asn His Gly Pro Val Val Ala Gly Val Ile Gly Ala Gln Lys Pro Gln
            980                 985                 990
Tyr Asp Ile Trp Gly Asn Thr Val Asn Val Ala Ser Arg Met Glu Ser
        995                 1000                1005
Thr Gly Val Leu Gly Lys Ile Gln Val Thr Glu Glu Thr Ala Arg Ala
    1010                1015                1020
Leu Gln Ser Leu Gly Tyr Thr Cys Tyr Ser Arg Gly Val Ile Lys Val
1025                1030                1035                1040
Lys Gly Lys Gly Gln Leu Cys Thr Tyr Phe Leu Asn Thr Asp Leu Thr
                1045                1050                1055
Arg Thr Gly Ser Pro Ser Ala Ser
            1060
```

(2) INFORMATION FOR SEQ ID NO:9:

(i) SEQUENCE CHARACTERISTICS:
        (A) LENGTH: 3924 base pairs
        (B) TYPE: nucleic acid
        (C) STRANDEDNESS: single
        (D) TOPOLOGY: linear (xi) SEQUENCE DESCRIPTION: SEQ ID NO:9:

```
GTCGAGGAAA AGGCCGAGCG GCCGAGGAGC TGGAGCCCGG AACTGGCACC GTCGAGGATG    60

GAGACGGGTC CGAGGATGGA GGCAGTTCCG TGGCGTCAGG CTCTGGGACC GGCACGGTGC   120

TGTCGTTGGG CGCCTGCTGC CTGGCCTTGC TGCAGATATT CCGCTCTAAG AAGTTCCCGT   180

CGGACAAACT GGAGCGTCTG TACCAGCGCT ATTTCTTCCG CCTGAACCAG AGCAGCCTCA   240

CCATGCTCAT GGCCGTGCTG GTGCTCGTGT GCCTGGTCAT GCTCGCTTTC CACGCGGCAC   300

GGCCCCCGCT CCAGGTAGTC TACCTGGCCG TGTTGGCAGC TGCTGTGGGC GTGATCCTTA   360

TCATGGCTGT GCTCTGCAAC CGTGCAGCCT TCCACCAGGA CCACATGGGC CTGGCCTGCT   420

ATGCGCTCAT TGCAGTGGTG CTGGCCGTCC AGGTAGTGGG CCTGTTGCTG CCACAGCCAC   480

GCAGCGCCTC CGAGGGCATC TGGTGGACCG TGTTCTTCAT CTATACCATC TACACCCTGC   540

TGCCTGTGCG CATGAGGGCT GCGGTGCTCA GCGGGGTGCT TCTGTCGGCT CTCCACTTGG   600

CCATCTCTCT GCACACCAAC GCCCAGGACC AGTTTCTGCT GAAACAGCTT GTCTCCAACG   660

TCCTCATCTT CTCCTTGCAC CAACATCGTG GTGTGTGCAC TCACTACCCA GCCGAGGTCT   720

CCCAGAGACA AGCCTTCCAG GAGACCCGGG AGTGCATCCA AGCTCGGCTC CACTCACAGC   780
```

-continued

```
GGGAGAACCA GCAACAGGAG CGTCTCCTGC TGTCTGTCCT TCCCCGTCAT GTTGCCATGG    840

AGATGAAAGC AGACATCAAC GCCAAACAGG AGGATATGAT GTTCCACAAG ATTTACATCC    900

AGAAACATGA CAATGTGAGC ATCCTGTTTG CTGACATCGA AGGCTTCACT AGCCTGGCAT    960

CCCAGTGTAC TGCCCAAGAA CTGGTCATGA CCCTCAACGA GCTCTTCGCC CGCTTTGACA   1020

AGTTGGCTGC GGAGAATCAC TGCTTACGGA TTAAGATCCT CGGGGATTGT TACTACTGTG   1080

TCTCGGGGCT GCCTGAAGCC AGAGCTGACC ACGCCCACTG CTGCGTAGAG ATGGGAATGG   1140

ACATGATCGA GGCCATCTCG TCGGTCCGGG AGGTGACAGG GGTGAACGTG AACATGCGTG   1200

TGGGAATTCA CAGCGGGAGA GTACACTGCG GTGTCCTTGG CCTCAGAAAG TGGCAATTCG   1260

ACGTGTGGTC TAACGATGTC ACACTGGCCA ACCACATGGA AGCTGGCGGC AAGGCAGGCC   1320

GCATCCACAT CACCAAGGCC ACACTCAACT ACCTGAACGG GGACTATGAG GTGGAGCCAG   1380

GCTGTGGTGG TGAGCGCAAT GCCTACCTCA AGGAGCACAG CATCGAGACC TTCCTCATCC   1440

TGCGCTGTAC CCAGAAGCGG AAAGAAGAGA AGGCCATGAT CGCCAAGATG AACCGCCAGA   1500

GAACCAACTC CATTGGACAC AATCCGCCTC ACTGGGGAGC TGAGCGCCCC TTCTACAACC   1560

ACTTGGGTGG CAACCAGGTG TCCAAGGAAA TGAAGAGGAT GGGCTTTGAG GACCCCAAGG   1620

ACAAGAATGC CCAGGAAAGT GCCAACCCTG AGGATGAAGT GGACGAGTTT CTGGGTCGAG   1680

CCATCGATGC CAGGAGTATT GACAGACTGC GATCCGAACA CGTCCGAAAG TTCCTCTTGA   1740

CCTTTAGGGA GCCCGACTTA GAGAAGAAGT ACTCCAAGCA GGTGGATGAC CGATTTGGTG   1800

CCTATGTGGC CTGTGCCTCG CTTGTTTTCC TCTTCATCTG CTTTGTCCAG ATCACCATTG   1860

TGCCCCACTC CCTGTTCATG CTGAGCTTCT ACCTGTCGTG TTTCCTGCTA CTGGCCTTGG   1920

TGGTGTTTAT ATCTGTGATC TACGCCTGTG TGAAGCTCTT CCCTACTCCC CTGCAGACAC   1980

TCTCCAGGAA GATAGTGCGA TCCAAGAAGA ACAGCACCCT GGTCGGGGTG TTCACCATCA   2040

CCCTGGTGTT CCTCTCGGCT TTTGTCAACA TGTTCATGTG CAACTCTAAG AACCTGGTGG   2100

GTTGCCTGGC AGAGGAGCAC AACATCACGG TGAACCAGGT GAACGCATGT CATGTGATGG   2160

AGTCGGCCTT CAACTACAGC CTGGGCGACG AGCAGGGCTT CTGTGGCAGC CCCCAGTCCA   2220

ACTGCAACTT CCCAGAGTAC TTCACCTACA GCGTGCTGCT CAGCCTGCTG GCCTGCTCCG   2280

TGTTCCTGCA GATCAGCTGC ATCGGGAAGC TGGTGCTCAT GCTGGCCATC GAGCTCATCT   2340

ACGTGCTCAT CGTAGAGGTG CCCGGTGTCA CACTCTTTGA CAACGCTGAC CTTCTGGTCA   2400

CCGCCAATGC CATAGACTTC AGCAACAACG GGACCTCCCA GTGCCCTGAG CATGCGACCA   2460

AGGTGGCGCT GAAGGTGGTG ACGCCCATCA TCATCTCTGT CTTCGTGCTG GCTCTGTATC   2520

TGCATGCTCA GCAGGTGGAA TCCACTGCTC GCCTTGACTT CCTCTGGAAA CTGCAGGCCA   2580

CAGAAGAGAA GGAGGAGATG GAGGAGCTGC AGGCCTACAA CCGGCGCTTG CTGCACAACA   2640

TTCTGCCCAA GGACGTGGCT GCCCACTTCC TGGCCCGGGA GCGGCGCAAT GATGAACTGT   2700

ACTACCAATC CTGCGAGTGC GTGGCTGTCA TGTTTGCCTC CATCGCCAAC TTCTCCGAAT   2760

TCTACGTGGA GCTAGAGGCC AACAATGAGG GCGTTGAATG CCTACGGCTG CTCAATGAGA   2820

TCATCGCAGA CTTTGATGAG ATCATCAGTG AGGATCGGTT CAGGCAGCTG GAAAAGATCA   2880

AGACCATAGG TAGCACCTAC ATGGCTGCCT CTGGCCTCAA CGACTCCACC TATGACAAGG   2940

CAGGCAAGAC CCACATCAAG GCTCTTGCAG ACTTCGCCAT GAAGCTGATG GACCAAATGA   3000

AGTACATCAA TGAGCACTCC TTCAACAACT TCCAGATGAA GATCGGGCTT AACATTGGAC   3060

CTGTAGTGGC TGGGGTCATT GGGGCTCGCA AGCCTCAGTA TGACATCTGG GGCAATACAG   3120

TAAATGTGGC CAGCCGTATG GACAGCACTG GGGTGCCTGA CCGCATCCAG GTTACTACAG   3180
```

```
ATATGTACCA GGTGCTGGCC GCCAACACAT ACCAGCTGGA GTGCCGGGGT GTGGTCAAGG      3240

TCAAGGGCAA GGGTGAGATG ATGACCTACT TCCTCAATGG AGGGCCTCCC CTCAGTTAGC      3300

AGATACCAGC AGCATCCTGG CCTCCAGAGG ATTGAACAGC TTCTCTGTGC ACCATGGGCA      3360

GATAGGGCCT GTGCCCAGGC TCACAGCTGT GCTGGTAAAA TTTCTACTTG GACTCAGAAG      3420

CAACTTCTGC CTTTGCTGGT GGGCATGCAT TTTGGCCTAG GCCAGGGTGC CAGCGTCCTG      3480

CGAGCACCGA GCTGACCAAA GATGTTGCCC TTGGCAGAAG ACTGTAGACT CGAGCTGACC      3540

CTTGAGGTTC TGACAAGTGC TGCTACTGCA CGGTGGATGT GCTACCGGAG CACAGCCTGG      3600

CACAGAGTGG CTGGCCTGAG GGGAGGCCTT GGTTATGAAG GGGAGGTAGG CAAGCTTGAA      3660

GCTGGCCTGG GGGATGTCCA TGGACCTCAT GGGTCTGCTT TCCACTGTGG AGAGGCTATG      3720

CCCCCTCACA ACGTTTTGGG GGCAGGAACT GGGAGAGATG CGGCCTGTGC CATTCTCTCC      3780

TCACACCTCC ATGCACACAG ACAATGCCCT GTACGGGAAA CAGGACTGTT GATAAGGGGG      3840

AGGCAAGAGG ACACCAGGCA AGGAGCAGTG GCTCTGAGCA AAGAAAATA TTTATTAAAT       3900

AAAACAAAAG TTTTCTCTGC CCTT                                              3924

(2) INFORMATION FOR SEQ ID NO:10:

(i) SEQUENCE CHARACTERISTICS:
        (A) LENGTH: 1098 amino acids
        (B) TYPE: amino acid
        (C) STRANDEDNESS:
        (D) TOPOLOGY: linear (xi) SEQUENCE DESCRIPTION: SEQ ID NO:10:

Arg Gly Lys Gly Arg Ala Ala Glu Glu Leu Glu Pro Gly Thr Gly Thr
1               5                   10                  15

Val Glu Asp Gly Asp Gly Ser Glu Asp Gly Gly Ser Ser Val Ala Ser
            20                  25                  30

Gly Ser Gly Thr Gly Thr Val Leu Ser Leu Gly Ala Cys Cys Leu Ala
        35                  40                  45

Leu Leu Gln Ile Phe Arg Ser Lys Lys Phe Pro Ser Asp Lys Leu Glu
    50                  55                  60

Arg Leu Tyr Gln Arg Tyr Phe Phe Arg Leu Asn Gln Ser Ser Leu Thr
65                  70                  75                  80

Met Leu Met Ala Val Leu Val Leu Cys Leu Val Met Leu Ala Phe
                85                  90                  95

His Ala Ala Arg Pro Pro Leu Gln Val Val Tyr Leu Ala Val Leu Ala
                100                 105                 110

Ala Ala Val Gly Val Ile Leu Ile Met Ala Val Leu Cys Asn Arg Ala
            115                 120                 125

Ala Phe His Gln Asp His Met Gly Leu Ala Cys Tyr Ala Leu Ile Ala
        130                 135                 140

Val Val Leu Ala Val Gln Val Gly Leu Leu Pro Gln Pro Arg
145                 150                 155                 160

Ser Ala Ser Glu Gly Ile Trp Trp Thr Val Phe Phe Ile Tyr Thr Ile
                165                 170                 175

Tyr Thr Leu Leu Pro Val Arg Met Arg Ala Ala Val Leu Ser Gly Val
                180                 185                 190

Leu Leu Ser Ala Leu His Leu Ala Ile Ser Leu His Thr Asn Ala Gln
            195                 200                 205

Asp Gln Phe Leu Leu Lys Gln Leu Val Ser Asn Val Leu Ile Phe Ser
        210                 215                 220
```

-continued

| | | | | | | | | | | | | | | | |
|---|---|---|---|---|---|---|---|---|---|---|---|---|---|---|---|
| Cys<br>225 | Thr | Asn | Ile | Val<br>230 | Gly | Val | Cys | Thr | His<br>235 | Tyr | Pro | Ala | Glu | Val<br>240 | Ser |
| Gln | Arg | Gln | Ala | Phe<br>245 | Gln | Glu | Thr | Arg | Glu<br>250 | Cys | Ile | Gln | Ala | Arg<br>255 | Leu |
| His | Ser | Gln | Arg<br>260 | Glu | Asn | Gln | Gln | Gln<br>265 | Glu | Arg | Leu | Leu | Leu<br>270 | Ser | Val |
| Leu | Pro | Arg<br>275 | His | Val | Ala | Met | Glu<br>280 | Met | Lys | Ala | Asp | Ile<br>285 | Asn | Ala | Lys |
| Gln<br>290 | Glu | Asp | Met | Met | Phe<br>295 | His | Lys | Ile | Tyr | Ile<br>300 | Gln | Lys | His | Asp | Asn |
| Val<br>305 | Ser | Ile | Leu | Phe | Ala<br>310 | Asp | Ile | Glu | Gly | Phe<br>315 | Thr | Ser | Leu | Ala | Ser<br>320 |
| Gln | Cys | Thr | Ala | Gln<br>325 | Glu | Leu | Val | Met | Thr<br>330 | Leu | Asn | Glu | Leu | Phe<br>335 | Ala |
| Arg | Phe | Asp | Lys<br>340 | Leu | Ala | Ala | Glu | Asn<br>345 | His | Cys | Leu | Arg | Ile<br>350 | Lys | Ile |
| Leu | Gly | Asp<br>355 | Cys | Tyr | Tyr | Cys | Val<br>360 | Ser | Gly | Leu | Pro | Glu<br>365 | Ala | Arg | Ala |
| Asp | His<br>370 | Ala | His | Cys | Cys | Val<br>375 | Glu | Met | Gly | Met | Asp<br>380 | Met | Ile | Glu | Ala |
| Ile<br>385 | Ser | Ser | Val | Arg | Glu<br>390 | Val | Thr | Gly | Val | Asn<br>395 | Val | Asn | Met | Arg | Val<br>400 |
| Gly | Ile | His | Ser | Gly<br>405 | Arg | Val | His | Cys | Gly<br>410 | Val | Leu | Gly | Leu | Arg<br>415 | Lys |
| Trp | Gln | Phe | Asp<br>420 | Val | Trp | Ser | Asn | Asp<br>425 | Val | Thr | Leu | Ala | Asn<br>430 | His | Met |
| Glu | Ala | Gly | Gly | Lys<br>435 | Ala | Gly | Arg | Ile | His<br>440 | Ile | Thr | Lys | Ala | Thr<br>445 | Leu |
| Asn | Tyr | Leu<br>450 | Asn | Gly | Asp | Tyr | Glu<br>455 | Val | Glu | Pro | Gly | Cys<br>460 | Gly | Gly | Glu |
| Arg<br>465 | Asn | Ala | Tyr | Leu | Lys<br>470 | Glu | His | Ser | Ile | Glu<br>475 | Thr | Phe | Leu | Ile | Leu<br>480 |
| Arg | Cys | Thr | Gln | Lys<br>485 | Arg | Lys | Glu | Glu | Lys<br>490 | Ala | Met | Ile | Ala | Lys<br>495 | Met |
| Asn | Arg | Gln | Arg<br>500 | Thr | Asn | Ser | Ile | Gly<br>505 | His | Asn | Pro | Pro | His<br>510 | Trp | Gly |
| Ala | Glu | Arg<br>515 | Pro | Phe | Tyr | Asn | His<br>520 | Leu | Gly | Gly | Asn | Gln<br>525 | Val | Ser | Lys |
| Glu | Met<br>530 | Lys | Arg | Met | Gly | Phe<br>535 | Glu | Asp | Pro | Lys | Asp<br>540 | Lys | Asn | Ala | Gln |
| Glu<br>545 | Ser | Ala | Asn | Pro | Glu<br>550 | Asp | Glu | Val | Asp | Glu<br>555 | Phe | Leu | Gly | Arg | Ala<br>560 |
| Ile | Asp | Ala | Arg | Ser<br>565 | Ile | Asp | Arg | Leu | Arg<br>570 | Ser | Glu | His | Val | Arg<br>575 | Lys |
| Phe | Leu | Leu | Thr<br>580 | Phe | Arg | Glu | Pro | Asp<br>585 | Leu | Glu | Lys | Lys | Tyr<br>590 | Ser | Lys |
| Gln | Val | Asp<br>595 | Asp | Arg | Phe | Gly | Ala<br>600 | Tyr | Val | Ala | Cys | Ala<br>605 | Ser | Leu | Val |
| Phe | Leu<br>610 | Phe | Ile | Cys | Phe | Val<br>615 | Gln | Ile | Thr | Ile | Val<br>620 | Pro | His | Ser | Leu |
| Phe<br>625 | Met | Leu | Ser | Phe | Tyr<br>630 | Leu | Ser | Cys | Phe | Leu<br>635 | Leu | Leu | Ala | Leu | Val<br>640 |

-continued

```
Val Phe Ile Ser Val Ile Tyr Ala Cys Val Lys Leu Phe Pro Thr Pro
                645                 650                 655

Leu Gln Thr Leu Ser Arg Lys Ile Val Arg Ser Lys Lys Asn Ser Thr
            660                 665                 670

Leu Val Gly Val Phe Thr Ile Thr Leu Val Phe Leu Ser Ala Phe Val
            675                 680                 685

Asn Met Phe Met Cys Asn Ser Lys Asn Leu Val Gly Cys Leu Ala Glu
            690                 695                 700

Glu His Asn Ile Thr Val Asn Gln Val Asn Ala Cys His Val Met Glu
705                 710                 715                 720

Ser Ala Phe Asn Tyr Ser Leu Gly Asp Glu Gln Gly Phe Cys Gly Ser
                725                 730                 735

Pro Gln Ser Asn Cys Asn Phe Pro Glu Tyr Phe Thr Tyr Ser Val Leu
                740                 745                 750

Leu Ser Leu Leu Ala Cys Ser Val Phe Leu Gln Ile Ser Cys Ile Gly
            755                 760                 765

Lys Leu Val Leu Met Leu Ala Ile Glu Leu Ile Tyr Val Leu Ile Val
            770                 775                 780

Glu Val Pro Gly Val Thr Leu Phe Asp Asn Ala Asp Leu Leu Val Thr
785                 790                 795                 800

Ala Asn Ala Ile Asp Phe Ser Asn Asn Gly Thr Ser Gln Cys Pro Glu
                805                 810                 815

His Ala Thr Lys Val Ala Leu Lys Val Val Thr Pro Ile Ile Ile Ser
                820                 825                 830

Val Phe Val Leu Ala Leu Tyr Leu His Ala Gln Gln Val Glu Ser Thr
            835                 840                 845

Ala Arg Leu Asp Phe Leu Trp Lys Leu Gln Ala Thr Glu Glu Lys Glu
            850                 855                 860

Glu Met Glu Glu Leu Gln Ala Tyr Asn Arg Arg Leu Leu His Asn Ile
865                 870                 875                 880

Leu Pro Lys Asp Val Ala Ala His Phe Leu Ala Arg Glu Arg Arg Asn
                885                 890                 895

Asp Glu Leu Tyr Tyr Gln Ser Cys Glu Cys Val Ala Val Met Phe Ala
            900                 905                 910

Ser Ile Ala Asn Phe Ser Glu Phe Tyr Val Glu Leu Glu Ala Asn Asn
            915                 920                 925

Glu Gly Val Glu Cys Leu Arg Leu Leu Asn Glu Ile Ile Ala Asp Phe
            930                 935                 940

Asp Glu Ile Ile Ser Glu Asp Arg Phe Arg Gln Leu Glu Lys Ile Lys
945                 950                 955                 960

Thr Ile Gly Ser Thr Tyr Met Ala Ala Ser Gly Leu Asn Asp Ser Thr
                965                 970                 975

Tyr Asp Lys Ala Gly Lys Thr His Ile Lys Ala Leu Ala Asp Phe Ala
            980                 985                 990

Met Lys Leu Met Asp Gln Met Lys Tyr Ile Asn Glu His Ser Phe Asn
            995                1000                1005

Asn Phe Gln Met Lys Ile Gly Leu Asn Ile Gly Pro Val Val Ala Gly
            1010                1015                1020

Val Ile Gly Ala Arg Lys Pro Gln Tyr Asp Ile Trp Gly Asn Thr Val
1025                1030                1035                1040

Asn Val Ala Ser Arg Met Asp Ser Thr Gly Val Pro Asp Arg Ile Gln
                1045                1050                1055

Val Thr Thr Asp Met Tyr Gln Val Leu Ala Ala Asn Thr Tyr Gln Leu
```

```
                   1060              1065              1070
Glu Cys Arg Gly Val Val Lys Val Lys Gly Lys Gly Glu Met Met Thr
                1075              1080              1085

Tyr Phe Leu Asn Gly Gly Pro Pro Leu Ser
                1090              1095

(2) INFORMATION FOR SEQ ID NO:11:

(i) SEQUENCE CHARACTERISTICS:
        (A) LENGTH: 4131 base pairs
        (B) TYPE: nucleic acid
        (C) STRANDEDNESS: single
        (D) TOPOLOGY: linear (xi) SEQUENCE DESCRIPTION: SEQ ID NO:11:

GGCGGCACCA AGAATGCCCC TGCCCGTGGC CCGATCCGGT TCTGGGCGCA GCAGCATGTC     60

ATGGTTTAGC GGCCTCCTGG TTCCCAAAGT GGATGAACGG AAAACAGCCT GGGGCGAACG    120

CAATGGACAG AAGCGCCCAC GCCAGGCGAC CCGAGCCCGT GGCTTCTGCG CGCCCCGCTA    180

CATGAGCTGC CTCAAGAATG TGGAGCCACC CAGCCCCACT CCTGCAGCTC GCACTCGGTG    240

CCCCTGGCAG GATGAAGCCT TCATCAGGAG GGCTGGCCCG GGAAGGGGTG TGGAGCTGGG    300

GCTGCGGTCA GTGGCCTTGG GTTTTGATGA CACTGAGGTG ACCACACCGA TGGGGACAGC    360

TGAAGTGGCA CCCGACACAT CGCCTCGAAG CGGTCCGTCC TGCTGGCACC GGCTAGCGCA    420

GGTGTTCCAG TCTAAGCAGT TCCCGTCCGC CAAGCTGGAG CGTCTGTACC AGCGGTACTT    480

CTTCCAGATG AACCAGAGCA GCCTCACGCT GCTCATGGCG GTGCTTGTGC TCCTCATGGC    540

TGTACTGTTG ACCTTCCACG CCGCGCCTGC CCTGCCTCAG CCTGCTTATG TGGCCCTGCT    600

GACCTGTGCC TCCGTCCTTT TTGTGGTACT CATGGTAGTG TGTAACCGAC ATAGCTTCCG    660

CCAGGACTCC ATGTGGGTAG TGAGCTATGT GGTTCTGGGC ATCCTAGCAG CCGTGCAAGT    720

CGGGGGTGCC CTGGCAGCCA ACCCACGCAG CCCCTCAGCA GGCCTTTGGT GCCCCGTGTT    780

CTTCGTCTAC ATCACCTACA CACTTCTTCC CATTCGTATG CGAGCGGCCG TGCTCAGTGG    840

CCTGGGTCTT TCCACCCTGC ATTTGATTTT GGCCTGGCAT CTCAACAATG GTGACCCCTT    900

CCTTTGGAAG CAGCTCGGTG CTAACGTGGT GCTCTTCCTG TGCACCAATG CCATCGGTGT    960

CTGCACGCAC TACCCCGCTG AAGTGTCTCA GCGCCAAGCC TTTCAGGAGA CCCGTGGTTA   1020

CATCCAGGCC CGGCTGCACT TGCAGCATGA GAATCGACAG CAGGAACGGC TGCTGCTGTC   1080

GGTGTTGCCC CAGCATGTTG CCATGGAAAT GAAAGAGGAT ATCAACACAA AAAAGGAAGA   1140

CATGATGTTC CACAAGATTT ACATCCAGAA GCATGACAAT GTCAGCATCC TGTTTGCCGA   1200

CATCGAGGGC TTCACCAGCC TGGCCTCCCA GTGCACTGCC CAGGAACTGG TCATGACCTT   1260

GAATGAGCTC TTTGCCCGGT TCGACAAGCT GGCTGCGGAG AATCACTGTC TGAGGATCAA   1320

GATCTTAGGA GACTGTTACT ACTGTGTGTC GGGGCTGCCG GAGGCCCGGG CAGACCATGC   1380

CCACTGCTGT GTGGAGATGG GGTAGACAT GATCGAGGCC ATCTCGCTGG TGCGTGAGGT   1440

AACGGGTGTA AATGTGAACA TGCGCGTGGG CATCCACAGC GGGCGTGTAC ACTGCGGTGT   1500

CCTTGGTCTG CGGAAATGGC AGTTTGATGT CTGGTCCAAC GATGTGACCC TGGCCAACCA   1560

CATGGAGGCG GGGGGCCGGG CGGGCCGCAT CCACATCACT CGGGCCACAC TGCAGTACCT   1620

GAACGGGGAC TATGAGGTGG AGCCAGGCCG TGGCGGTGAG CGCAACGCGT ACCTCAAGGA   1680

GCAGTGCATT GAGACCTTCC TCATACTAGG AGCCAGCCAG AAACGGAAAG AGGAGAAGGC   1740

CATGCTGGTC AAGCTGCAGC GGACGCGGGC CAACTCCATG GAAGGACTGA TGCCCCGCTG   1800
```

```
GGTTCCTGAC CGTGCCTTCT CCCGGACCAA GGACTCTAAG GCATTCCGAC AGATGGGCAT    1860

CGATGACTCT AGCAAAGAGA ACCGGGGTGC CAAGATGCT  CTGAACCCTG AGGATGAGGT    1920

GGACGAGTTT CTGGGCCGAG CCATCGATGC CCGAAGCATC GACCAGCTGC GTAAGGACCA    1980

TGTGCGCCGG TTCCTGCTCA CCTTCCAGAG GGAGGATCTC GAGAAGAAGT ATTCACGGAA    2040

AGTAGACCCT CGTTTCGGAG CCTACGTCGC CTGTGCCCTC CTGGTTTTCT GCTTCATCTG    2100

TTTCATCCAG TTCCTCGTAT TCCCACACTC CGCCCTGATA CTCGGGATTT ATGCCGGGAT    2160

CTTCCTTTTG CTGCTGGTCA CCGTGCTCAT CTGTGCTGTG TGCTCCTGTG GGTCTTTCTT    2220

CCCCAACGCC CTGCAGCGCC TGTCCCGCAG TATCGTCCGC TCACGGGTGC ACAGCACGGC    2280

TGTTGGAGTC TTCTCGGTTC TGCTTGTGTT CATCTCTGCC ATTGCCAACA TGTTCACCTG    2340

CAGTCACACC CCACTGAGGA CCTGTGCGGC CCGGATGCTG AACTTAACAC CGTCCGATGT    2400

CACCGCCTGC CACCTACGAC AGCTCAATTA CTCTCTGGGA CTGGAAGCTC CCCTGTGTGA    2460

GGGCACCGCA CCCACCTGCA GCTTCCCTGA GTACTTTGTC GGGAGTGTGC TGCTGAGTCT    2520

CTTGGCCAGC TCCGTCTTCC TCCACATCAG CAGCATTGGC AAGCTAGTTA TGACCTTTGT    2580

CTTGGGGTTC ATCTACTTGC TTCTGCTTTT GCTGGGTCCC CCAGCCACCA TCTTTGACAA    2640

CTATGATCTA CTGCTTAGCG TCCATGGCTT GGCTTCCTCC AATGAGACCT TCGATGGGCT    2700

GGACTGCCCA GCCGTAGGGA GGGTAGCGCT CAAATACATG ACCCCTGTGA TTCTCCTCGT    2760

GTTCGCCCTG GCACTGTATC TACACGCACA ACAGGTGGAA TCTACCGCCC GCCTGGACTT    2820

CCTGTGGAAA CTGCAGGCCA CAGGGGAGAA GGAGGAGATG GAGGAGTTGC AGGCCTACAA    2880

CCGGCGGCTG CTGCATAACA TCCTTCCCAA GGACGTGGCT GCCCACTTCC TGGCCCGGGA    2940

GCGCCGCAAC GACGAGCTGT ACTACCAATC CTGCGAGTGC GTGGCTGTCA TGTTTGCCTC    3000

CATCGCCAAC TTCTCTGAGT TCTATGTGGA ACTGGAGGCG AACAATGAGG GCGTGGAGTG    3060

CCTGCGACTG CTCAATGAGA TCATCGCGGA CTTTGATGAG ATCATCAGTG AGGAGAGGTT    3120

CCGGCAGCTG GAGAAGATCA AGACCATCGG TAGCACTTAC ATGGCCGCCT CCGGGCTAAA    3180

TGCCAGCACC TATGACCAGG TCGGCCGCTC GCACATCACC GCCCTGGCAG ACTACGCCAT    3240

GCGGCTTATG GAGCAAATGA ACACATCAA  CGAACACTCT TTCAACAACT TCCAGATGAA    3300

GATCGGGTTG AACATGGGTC CGGTTGTAGC AGGTGTCATT GGGGCCCGGA AGCCACAGTA    3360

TGACATCTGG GGAAACACGG TGAATGTTTC CAGCCGTATG GACAGCACAG GAGTTCCTGA    3420

CCGAATACAG GTGACCACGG ATCTCTACCA GGTTCTAGCT GCCAAGGGCT ACCAACTGGA    3480

GTGTCGAGGG GTGGTCAAGG TGAAGGGAAA GGGGGAGATG ACCACCTACT TCCTCAATGG    3540

GGGCCCCAGC AGTTAGCAGA GCGCACGAGT GGAAATTCAA CCAAAGGGAC CAAGGTGGGC    3600

ACTGAGTGGA CTTTTCTGCT CACTGGATGG AGCTGTGGCA GGGGGCTCTG AGCCTTCAGG    3660

TCTTGCTGAC AGCAAAAGGG AACACCCCAG CAGGCTGTGC TTGGACCATA TCCGTCTGCC    3720

TTCAGAGCAG CAAAGGAAGG GACGCCGAGA GGATTATTAT CCAAGTGACT TCTTAATCA     3780

GAGTAAGGCT GTTTGCTTTT TTTTCCCCCC CTTTGGACGC AGCTGAGAGC AGAGCCTCCT    3840

GTTTGAGAGT AAAATGGCAA CTTACTCTGC CTACTGTTTC CCTGTCTGGG CGACAGGCTC    3900

AGGGCTGGGA CCTTTCTTTC CCTATTTTTC CTGGGACTAT TTTTGTACAA GAGTGGGGCA    3960

GGCATGAGGA ATGCTTGCCT TCACTGGCCT GTGTCAGCAG CATTTGTCTT GGGCACTCCC    4020

AGTACCAGCC AAGTCTCCTT CCTAGCACAA CAAGGCAGAG GAAGGAGGTG CTGTGGGACC    4080

TAGCTCTGAC CAGATTTCAG GGGAATGTTT CCATTTGCCA AATCCTAGTC C             4131
```

(2) INFORMATION FOR SEQ ID NO:12:

(i) SEQUENCE CHARACTERISTICS:
        (A) LENGTH: 1180 amino acids
        (B) TYPE: amino acid
        (C) STRANDEDNESS:
        (D) TOPOLOGY: linear (xi) SEQUENCE DESCRIPTION: SEQ ID NO:12:

```
Met Pro Leu Pro Val Ala Arg Ser Gly Ser Gly Arg Ser Ser Met Ser
 1               5                  10                  15

Trp Phe Ser Gly Leu Leu Val Pro Lys Val Asp Glu Arg Lys Thr Ala
            20                  25                  30

Trp Gly Glu Arg Asn Gly Gln Lys Arg Pro Arg Gln Ala Thr Arg Ala
        35                  40                  45

Arg Gly Phe Cys Ala Pro Arg Tyr Met Ser Cys Leu Lys Asn Val Glu
    50                  55                  60

Pro Pro Ser Pro Thr Pro Ala Ala Arg Thr Arg Cys Pro Trp Gln Asp
65                  70                  75                  80

Glu Ala Phe Ile Arg Arg Ala Gly Pro Gly Arg Gly Val Glu Leu Gly
                85                  90                  95

Leu Arg Ser Val Ala Leu Gly Phe Asp Asp Thr Glu Val Thr Thr Pro
            100                 105                 110

Met Gly Thr Ala Glu Val Ala Pro Asp Thr Ser Pro Arg Ser Gly Pro
        115                 120                 125

Ser Cys Trp His Arg Leu Ala Gln Val Phe Gln Ser Lys Gln Phe Pro
    130                 135                 140

Ser Ala Lys Leu Glu Arg Leu Tyr Gln Arg Tyr Phe Phe Gln Met Asn
145                 150                 155                 160

Gln Ser Ser Leu Thr Leu Leu Met Ala Val Leu Val Leu Leu Met Ala
                165                 170                 175

Val Leu Leu Thr Phe His Ala Ala Pro Ala Leu Pro Gln Pro Ala Tyr
            180                 185                 190

Val Ala Leu Leu Thr Cys Ala Ser Val Leu Phe Val Val Leu Met Val
        195                 200                 205

Val Cys Asn Arg His Ser Phe Arg Gln Asp Ser Met Trp Val Val Ser
    210                 215                 220

Tyr Val Val Leu Gly Ile Leu Ala Ala Val Gln Val Gly Gly Ala Leu
225                 230                 235                 240

Ala Ala Asn Pro Arg Ser Pro Ser Ala Gly Leu Trp Cys Pro Val Phe
                245                 250                 255

Phe Val Tyr Ile Thr Tyr Thr Leu Leu Pro Ile Arg Met Arg Ala Ala
            260                 265                 270

Val Leu Ser Gly Leu Gly Leu Ser Thr Leu His Leu Ile Leu Ala Trp
        275                 280                 285

His Leu Asn Asn Gly Asp Pro Phe Leu Trp Lys Gln Leu Gly Ala Asn
    290                 295                 300

Val Val Leu Phe Leu Cys Thr Asn Ala Ile Gly Val Cys Thr His Tyr
305                 310                 315                 320

Pro Ala Glu Val Ser Gln Arg Gln Ala Phe Gln Glu Thr Arg Gly Tyr
                325                 330                 335

Ile Gln Ala Arg Leu His Leu Gln His Glu Asn Arg Gln Gln Glu Arg
            340                 345                 350

Leu Leu Leu Ser Val Leu Pro Gln His Val Ala Met Glu Met Lys Glu
        355                 360                 365
```

```
Asp Ile Asn Thr Lys Lys Glu Asp Met Met Phe His Lys Ile Tyr Ile
    370                 375                 380

Gln Lys His Asp Asn Val Ser Ile Leu Phe Ala Asp Ile Glu Gly Phe
385                 390                 395                 400

Thr Ser Leu Ala Ser Gln Cys Thr Ala Gln Glu Leu Val Met Thr Leu
                405                 410                 415

Asn Glu Leu Phe Ala Arg Phe Asp Lys Leu Ala Ala Glu Asn His Cys
                420                 425                 430

Leu Arg Ile Lys Ile Leu Gly Asp Cys Tyr Tyr Cys Val Ser Gly Leu
            435                 440                 445

Pro Glu Ala Arg Ala Asp His Ala His Cys Cys Val Glu Met Gly Val
        450                 455                 460

Asp Met Ile Glu Ala Ile Ser Leu Val Arg Glu Val Thr Gly Val Asn
465                 470                 475                 480

Val Asn Met Arg Val Gly Ile His Ser Gly Arg Val His Cys Gly Val
                485                 490                 495

Leu Gly Leu Arg Lys Trp Gln Phe Asp Val Trp Ser Asn Asp Val Thr
            500                 505                 510

Leu Ala Asn His Met Glu Ala Gly Gly Arg Ala Gly Arg Ile His Ile
        515                 520                 525

Thr Arg Ala Thr Leu Gln Tyr Leu Asn Gly Asp Tyr Glu Val Glu Pro
530                 535                 540

Gly Arg Gly Gly Glu Arg Asn Ala Tyr Leu Lys Glu Gln Cys Ile Glu
545                 550                 555                 560

Thr Phe Leu Ile Leu Gly Ala Ser Gln Lys Arg Lys Glu Glu Lys Ala
                565                 570                 575

Met Leu Val Lys Leu Gln Arg Thr Arg Ala Asn Ser Met Glu Gly Leu
            580                 585                 590

Met Pro Arg Trp Val Pro Asp Arg Ala Phe Ser Arg Thr Lys Asp Ser
        595                 600                 605

Lys Ala Phe Arg Gln Met Gly Ile Asp Asp Ser Ser Lys Glu Asn Arg
610                 615                 620

Gly Ala Gln Asp Ala Leu Asn Pro Glu Asp Glu Val Asp Glu Phe Leu
625                 630                 635                 640

Gly Arg Ala Ile Asp Ala Arg Ser Ile Asp Gln Leu Arg Lys Asp His
                645                 650                 655

Val Arg Arg Phe Leu Leu Thr Phe Gln Arg Glu Asp Leu Glu Lys Lys
            660                 665                 670

Tyr Ser Arg Lys Val Asp Pro Arg Phe Gly Ala Tyr Val Ala Cys Ala
        675                 680                 685

Leu Leu Val Phe Cys Phe Ile Cys Phe Ile Gln Phe Leu Val Phe Pro
690                 695                 700

His Ser Ala Leu Ile Leu Gly Ile Tyr Ala Gly Ile Phe Leu Leu Leu
705                 710                 715                 720

Leu Val Thr Val Leu Ile Cys Ala Val Cys Ser Cys Gly Ser Phe Phe
                725                 730                 735

Pro Asn Ala Leu Gln Arg Leu Ser Arg Ser Ile Val Arg Ser Arg Val
            740                 745                 750

His Ser Thr Ala Val Gly Val Phe Ser Val Leu Leu Val Phe Ile Ser
        755                 760                 765

Ala Ile Ala Asn Met Phe Thr Cys Ser His Thr Pro Leu Arg Thr Cys
770                 775                 780

Ala Ala Arg Met Leu Asn Leu Thr Pro Ser Asp Val Thr Ala Cys His
```

-continued

```
            785                 790                 795                 800
Leu Arg Gln Leu Asn Tyr Ser Leu Gly Leu Glu Ala Pro Leu Cys Glu
                    805                 810                 815
Gly Thr Ala Pro Thr Cys Ser Phe Pro Glu Tyr Phe Val Gly Ser Val
            820                 825                 830
Leu Leu Ser Leu Leu Ala Ser Ser Val Phe Leu His Ile Ser Ser Ile
            835                 840                 845
Gly Lys Leu Val Met Thr Phe Val Leu Gly Phe Ile Tyr Leu Leu Leu
        850                 855                 860
Leu Leu Leu Gly Pro Pro Ala Thr Ile Phe Asp Asn Tyr Asp Leu Leu
865                 870                 875                 880
Leu Ser Val His Gly Leu Ala Ser Ser Asn Glu Thr Phe Asp Gly Leu
                    885                 890                 895
Asp Cys Pro Ala Val Gly Arg Val Ala Leu Lys Tyr Met Thr Pro Val
                900                 905                 910
Ile Leu Leu Val Phe Ala Leu Ala Leu Tyr Leu His Ala Gln Gln Val
            915                 920                 925
Glu Ser Thr Ala Arg Leu Asp Phe Leu Trp Lys Leu Gln Ala Thr Gly
        930                 935                 940
Glu Lys Glu Glu Met Glu Glu Leu Gln Ala Tyr Asn Arg Arg Leu Leu
945                 950                 955                 960
His Asn Ile Leu Pro Lys Asp Val Ala Ala His Phe Leu Ala Arg Glu
                965                 970                 975
Arg Arg Asn Asp Glu Leu Tyr Tyr Gln Ser Cys Glu Cys Val Ala Val
                    980                 985                 990
Met Phe Ala Ser Ile Ala Asn Phe Ser Glu Phe Tyr Val Glu Leu Glu
                995                 1000                1005
Ala Asn Asn Glu Gly Val Glu Cys Leu Arg Leu Leu Asn Glu Ile Ile
        1010                1015                1020
Ala Asp Phe Asp Glu Ile Ile Ser Glu Glu Arg Phe Arg Gln Leu Glu
1025                1030                1035                1040
Lys Ile Lys Thr Ile Gly Ser Thr Tyr Met Ala Ala Ser Gly Leu Asn
                    1045                1050                1055
Ala Ser Thr Tyr Asp Gln Val Gly Arg Ser His Ile Thr Ala Leu Ala
            1060                1065                1070
Asp Tyr Ala Met Arg Leu Met Glu Gln Met Lys His Ile Asn Glu His
        1075                1080                1085
Ser Phe Asn Asn Phe Gln Met Lys Ile Gly Leu Asn Met Gly Pro Val
        1090                1095                1100
Val Ala Gly Val Ile Gly Ala Arg Lys Pro Gln Tyr Asp Ile Trp Gly
1105                1110                1115                1120
Asn Thr Val Asn Val Ser Ser Arg Met Asp Ser Thr Gly Val Pro Asp
                    1125                1130                1135
Arg Ile Gln Val Thr Thr Asp Leu Tyr Gln Val Leu Ala Ala Lys Gly
            1140                1145                1150
Tyr Gln Leu Glu Cys Arg Gly Val Val Lys Val Lys Gly Lys Gly Glu
        1155                1160                1165
Met Thr Thr Tyr Phe Leu Asn Gly Gly Pro Ser Ser
        1170                1175                1180

(2) INFORMATION FOR SEQ ID NO:13:

(i) SEQUENCE CHARACTERISTICS:
        (A) LENGTH: 5199 base pairs
```

(B) TYPE: nucleic acid
        (C) STRANDEDNESS: single
        (D) TOPOLOGY: linear (xi) SEQUENCE DESCRIPTION: SEQ ID NO:13:

```
GTGGCTCCCT CCTGCAGCCT CAGGGACACC GGAGATGGCC CAGTGCGGCA GGTAACAGGG      60

TCGGAGGCGG CTACGCGGGG GACCGTGTGG GGACGTTCCC GAGATCCCCA GCCCGCGCCC     120

CGCACGGTCA GTGTGACCAG CTGGGGCGC CCCGGCTCTC GCGCTCGCGG GCGGGAACTC      180

CAGAGCGCCC GGGCCCTCGG CGGTGGCGGC AGGGAAGAAG ATGTCTCTAC CTGGAAGCTC     240

CCAGGAGACA GCTGTGGAGC CCACGAGAGC CACAGGGCCT TGACCTCATC TCTTCCCACC     300

ATCCAAGAGG GCAAAGTCAG GGGCTTTAAA CGGGAGAGGA GAGACGACTC AGCACTCCTT     360

GTGATAAGGC CCTGTGGATG TGTGGCTAGC TTGCTCTGTC CTGTGCGTCA AGGAATGCAG     420

GTGCAAAGAG CTGAGGACCT GGAAGTTTCT GTCAGCTCCT CCTAGACACC CTGAAGACAC     480

CAGTGAACAG AACCCAGTGG CTGGAGCAGG TGTCACATGC TCATGGAGCC ACGGGCTCTA     540

GGTGCCTCTG TCCAGTCCTG CCTGATACCC TCAGAAAGGG AAGAAGCCTA GCCACACAC     600

TAAAGCGTCA GCTGACAGAT GTATCTCAGA CCGTGGGGCT CCTGAGCAGG CTGCTGGACC     660

AGGCCACTGG GGAAGAGGAT GCCAGCCAAG GGGCGCTACT TCCTAAATGA GGGTGATGAA     720

GGCCCCGACC AGGCAGCGCT CTATGAGAAG TACCGGCTCA CCAGCTTGCA CGGGCCACTG     780

CTGCTCTTGC TCCTCCTGGT GGCCGCGGCC ACCTGCATTG CGCTCATCAG CATCGCCTTC     840

AGTCATGAGG ATCTCCGCAG ACACCAGGTT GTCCTGGGCA CTGCGTTCCT CATGCTGACG     900

CTGTTTGTGG CTCTCTATGT GCTGGTGTAT GTCGAGTGCC TGGTGCAGCG GTGGCTGCGG     960

GCCTTGGCGC TACTCACCTG GCTTGCCTC ATGGTACTAG GCTCCGTGCT GATGTGGGAC     1020

TCTTTGGAGA ATGAAGCCCA TGCGTGGAG CAGGTGCCTT TCTTCCTGTT TGTCGTCTTT     1080

GTGGTGTATG CACTACTGCC TCTCAGCAGG AGGGCAGCCA TCGTGGTAGG CGTGACCTCC     1140

ACGGTCTCCC ATCTCCTGGT GTTTGGAGCT GTGACAAGAG CCTTCCAGAC GTCCATGTCT     1200

AGCACTCAAC TGGGGCTGCA GCTCCTGGCC AATGCCGTTA TTCTCCTGGG TGGGAACTTC     1260

ACGGGTGCCT TCCACAAGCA CCAGCTGCAG GACGCGTCCA GGGATCTCTT TATCTACACC     1320

GTCAAATGCA TCCAGATCCG TCGGAAGCTT CGTGTGGAGA AGCGCCAACA GGAGAACCTG     1380

CTTCTGTCAG TGCTCCCAGC ACACATCTCC ATGGGTATGA AGCTGGCCAT CATTGAGCGC     1440

CTCAAAGAGG GTGGTGACCG ACACTACATG CCCGACAACA ACTTTCACAG CCTCTATGTC     1500

AAGCGGCACC AGAATGTCAG CATCTTGTAT GCAGACATCG TGGGCTTCAC GAGGCTGGCC     1560

AGCGACTGCT CTCCCAAGGA GCTGGTGGTG GTGCTCAACG AGCTGTTTGG AAGTTTGAC     1620

CAGATTGCTA AGGCCAATGA GTGCATGCGG ATCAAGATCC TGGGTGACTG TTACTACTGC     1680

GTGTCAGGCC TGCCCGTATC GCTGCCCACA CATGCCCGCA ACTGTGTGAA GATGGGTCTG     1740

GACATCTGCG AGGCCATTAA GCAGGTGCGT GAGGCCACGG GCGTGGACAT CAGCATGCGT     1800

GTGGGCATTC ACTCCGGGAA TGTGCTATGT GGGGTCATCG GCTCCGTAA GTGGCAGTAT     1860

GATGTGTGGT CCCATGATGT GTCCCTGGCC AACAGGATGG AGGCAGCTGG AGTCCCTGGC     1920

CGGGTGCACA TCACAGAGGC AACATTGAAT CACCTGGACA AGGCATACGA GGTGGAGGAT     1980

GGGCATGGGG AGCAGCGAGA CCCCTATCTG AAAGAGATGA ACATCCGAAC CTACCTGGTG     2040

ATCGATCCCC GGAGCCAGCA GCCACCCCCA CCCAGCCACC ACCTCTCCAA GCCCAAGGGG     2100

GACGCAACTC TGAAGATGCG GGCTTCAGTG CGTGTAACCC GCTATCTGGA GTCTTGGGGG     2160

GCAGCACGGC CCTTTGCACA CCTCAACCAC CGGGAGAGTG TGAGCAGCAG TGAGACCCCC     2220
```

```
ATCTCCAATG GACGGAGGCA GAAGGCCATT CCTCTGCGTC GACACCGTGC CCCTGATAGG    2280

AGTGCATCCC CCAAGGGGCG CTTGGAAGAT GACTGTGATG ACGAGATGCT GTCAGCCATT    2340

GAGGGTCTCA GCTCCACCAG GCCCTGCTGC TCCAAGTCTG ATGACTTCCA CACCTTTGGT    2400

CCCATCTTCT TGGAGAAGGG CTTTGAGCGT GAGTACCGCC TGGTGCCCAT CCCCCGGGCT    2460

CGCTACGACT TCGCCTGTGC CAGCCTTGTC TTCGTCTGCA TCCTGCTTGT CCACCTTCTA    2520

GTGATGCCCA GGATGGCAAC TCTGGGTGTG TCCTTTGGGT TGGTGGCCTG CCTGCTGGGG    2580

CTGGTTCTGA GTTTCTGCTT TGCTACTGAG TTCTCGAGGT GCTTTCCATC CCGAAGTACA    2640

CTCCAGGCCA TCTCGGAGAG CGTGGAGACG CAGCCCCTGG TCAGGCTTGT CCTGGTTGTG    2700

CTGACTGTTG GCAGCCTACT GACTGTCGCC ATCATTAACA TGCCACTGAC GCTTAACCCA    2760

GGCCCAGAGC AGCCTGGAGA CAACAAGACA AGCCCACTGG CTGCACAGAA CAGAGTTGGG    2820

ACCCCATATG AGCTCCTCCC GTACTACACC TGCAGCTGCA TCCTGGGCTT CATTGCATGC    2880

TCTGTTTTCC TGCGGATGAG CCTAGAGCTG AAGGCCATGC TGCTGACAGT GGCCTTGGTG    2940

GCCTACCTGC TGCTCTTCAA CCTCTCCCCA TGCTGGCACG TCTCAGGCAA CAGCACTGAG    3000

ACCAACGGGA CACAAAGGAC ACGGCTGCTC CTGTCTGATG CACAAAGCAT GCCCAGCCAC    3060

ACCCTTGCTC CGGGGGCTCA GGAGACTGCC CCTTCTCCCA GTTATTTAGA GAGAGACCTG    3120

AAGATCATGG TTAACTTCTA CCTGATCCTG TTCTATGCCA CCCTCATCTT GCTGTCTAGA    3180

CAGATTGACT ACTACTGCCG CTTGGACTGT CTGTGGAAGA AGAAGTTCAA AAAGGAGCAC    3240

GAGGAGTTTG AAACAATGGA GAATGTGAAC CGCCTCCTCC TGGAGAATGT GCTGCCGGCG    3300

CACGTGGCTG CCCACTTCAT TGGGGACAAG GCAGCAGAGG ATTGGTACCA TCAATCTTAT    3360

GACTGTGTCT GTGTCATGTT TGCATCCGTT CCGGACTTCA AAGTGTTCTA CACTGAGTGT    3420

GATGTCAACA AGAAGGACT GGAGTGCCTT CGACTGCTGA ATGAGATAAT TGCTGATTTT    3480

GACGAGCTCC TGCTGAAGCC CAAGTTCAGT GGTGTGGAGA AGATCAAGAC CATTGGCAGC    3540

ACCTACATGG CGGCAGCAGG GCTCAGTGCC CCCTCAGGAC ATGAGAACCA GGACCTGGAG    3600

CGGAAGCACG TGCACATCGG AGTCTTGGTA GAATTTAGCA TGGCCCTGAT GAGCAAGCTG    3660

GATGGGATCA ACAGGCACTC CTTCAACTCC TTCCGCCTCC GAGTCGGCAT AAACCACGGG    3720

CCTGTGATTG CTGGAGTGAT TGGAGCACGC AAGCCTCAGT ATGACATCTG GGGAAACACA    3780

GTCAATGTTG CCAGCCGCAT GGAGAGCACC GGAGAGCTTG GGAAAATCCA GGTTACCGAA    3840

GAGACATGCA CTATCCTCCA GGGACTCGGA TATTCGTGTG AATGCCGTGG GCTGATCAAC    3900

GTCAAAGGCA AGGGGAACT GCGGACTTAC TTTGTATGTA CAGACACTGC CAAGTTTCAA    3960

GGGCTGGGGC TAAACTGAGG TGGCTGGTGG TCAGCCTCCT TCCCCGAGGG AGCCAAGAAT    4020

GTAGCCCCAT GTCTGTTGCA GTGGCTTCTT TGGACTTGCA CTACAGGATG GCTTTGACCT    4080

GTGCATCAGA TTCGTTTGA AGCAGCTACT GCGTTGTACA CAGCGGCTCT GTGCTTCAGC    4140

CTCTACAGTT CCAAATTAGC TAGACCACTG GTCTACTACA GGCTGTGTTC ATTTCCAGGG    4200

TGCTGGGAA GAGACTTCAG TGCATGACCA AGATAGACAT CCACCTTGGT GCCAGTGAAC    4260

AGCATTCACA GGAGACAAAA GCTCTACTGG CTACAGGAGG CTCAGCCAGG CTTATTAGCA    4320

TGGGTTGCTG CTTGCCTTCC TCCCATCAAA TCTCCCATGG GATGTTATTC TTTCAATTAG    4380

GCATTCTGGT AAATGGAGTT GAAAACTGTG TATATTGGTG GGTAGTCTCA AAACAGCAGA    4440

GAAAATGTCT GATCTACACT TGTCACTTTT TTCCATCTCT GGCTTATGTT TGAAACGGAC    4500

ATGTCATAAA CAGAGTTTTA GCTTTACCAC TGACTCTTAG ATGCTAGACA AAGATCTCCA    4560
```

-continued

```
CCTTTCTAGT GTATTTTCTC TTGTTAACCA CAGACTACAA GTAAATAGGT CTGCTGTCTA    4620

GTGTCCTTTT ATAGGATCAG ATTGGCTGCA GGGACAGAGT TCTAAGGAAT GGGGCTCATA    4680

GCAGCAGCAA AGCTTTGAAT TTGCAATCAA GCATTTTTTG ATGCAAGTCT TTTGGGACAA    4740

GGCTCAGGAA GTTTAAAGTC TAGAAATGAG GTATGATGTT TCAGTTTTTC TGTGTGTACT    4800

TTATTTATTT TGGAGTCAGG GTCAGCCTAG CTTGGTCTCA AACTTCTAAC CTCCTGTTTC    4860

GGTCTCCGGA GTGTTTCAAT TACAGATGTG CACGACTATC TCCAGCTGTT TCTGTGGGAA    4920

AGCCTGTGTA GACAGGCTTG GACAACTTTG TAGCACTTGC CTTTTCTCCA GTCTTCTGAG    4980

CTGACGACAG AGCTTCAAGA ACAATCCACT TGACAGGAAC ATGTGTTCAG GACTCTGGCC    5040

TGTGAACTGA GCCCCTCAAC AAATGCCAAA TTGTTCTTAT GCAAATGAGT CAAGGCAAAA    5100

GCCAGCTTCG TGAGATGGGT GTCTTACTGT GCTTAGCTCC AGAGCATTCC GAGAGAGATG    5160

ACCAAACACC CCACTCCTTT TTGGAAATGA CCTCGTGCC                            5199
```

(2) INFORMATION FOR SEQ ID NO:14:

(i) SEQUENCE CHARACTERISTICS:
        (A) LENGTH: 1099 amino acids
        (B) TYPE: amino acid
        (C) STRANDEDNESS:
        (D) TOPOLOGY: linear (xi) SEQUENCE DESCRIPTION: SEQ ID NO:14:

```
Met Pro Ala Lys Gly Arg Tyr Phe Leu Asn Glu Gly Asp Glu Gly Pro
 1               5                  10                  15

Asp Gln Ala Ala Leu Tyr Glu Lys Tyr Arg Leu Thr Ser Leu His Gly
                20                  25                  30

Pro Leu Leu Leu Leu Leu Leu Val Ala Ala Thr Cys Ile Ala
            35                  40                  45

Leu Ile Ser Ile Ala Phe Ser His Glu Asp Leu Arg Arg His Gln Val
        50                  55                  60

Val Leu Gly Thr Ala Phe Leu Met Leu Thr Leu Phe Val Ala Leu Tyr
65                  70                  75                  80

Val Leu Val Tyr Val Glu Cys Leu Val Gln Arg Trp Leu Arg Ala Leu
                85                  90                  95

Ala Leu Leu Thr Trp Ala Cys Leu Met Val Leu Gly Ser Val Leu Met
            100                 105                 110

Trp Asp Ser Leu Glu Asn Glu Ala His Ala Trp Glu Gln Val Pro Phe
        115                 120                 125

Phe Leu Phe Val Val Phe Val Val Tyr Ala Leu Leu Pro Leu Ser Arg
    130                 135                 140

Arg Ala Ala Ile Val Val Gly Val Thr Ser Thr Val Ser His Leu Leu
145                 150                 155                 160

Val Phe Gly Ala Val Thr Arg Ala Phe Gln Thr Ser Met Ser Ser Thr
                165                 170                 175

Gln Leu Gly Leu Gln Leu Leu Ala Asn Ala Val Ile Leu Leu Gly Gly
            180                 185                 190

Asn Phe Thr Gly Ala Phe His Lys His Gln Leu Gln Asp Ala Ser Arg
        195                 200                 205

Asp Leu Phe Ile Tyr Thr Val Lys Cys Ile Gln Ile Arg Arg Lys Leu
    210                 215                 220

Arg Val Glu Lys Arg Gln Gln Glu Asn Leu Leu Leu Ser Val Leu Pro
225                 230                 235                 240

Ala His Ile Ser Met Gly Met Lys Leu Ala Ile Ile Glu Arg Leu Lys
```

-continued

```
                    245                 250                 255
Glu Gly Gly Asp Arg His Tyr Met Pro Asp Asn Asn Phe His Ser Leu
                260                 265                 270
Tyr Val Lys Arg His Gln Asn Val Ser Ile Leu Tyr Ala Asp Ile Val
            275                 280                 285
Gly Phe Thr Arg Leu Ala Ser Asp Cys Ser Pro Lys Glu Leu Val Val
        290                 295                 300
Val Leu Asn Glu Leu Phe Gly Lys Phe Asp Gln Ile Ala Lys Ala Asn
305                 310                 315                 320
Glu Cys Met Arg Ile Lys Ile Leu Gly Asp Cys Tyr Tyr Cys Val Ser
                325                 330                 335
Gly Leu Pro Val Ser Leu Pro Thr His Ala Arg Asn Cys Val Lys Met
                340                 345                 350
Gly Leu Asp Ile Cys Glu Ala Ile Lys Gln Val Arg Glu Ala Thr Gly
                355                 360                 365
Val Asp Ile Ser Met Arg Val Gly Ile His Ser Gly Asn Val Leu Cys
        370                 375                 380
Gly Val Ile Gly Leu Arg Lys Trp Gln Tyr Asp Val Trp Ser His Asp
385                 390                 395                 400
Val Ser Leu Ala Asn Arg Met Glu Ala Ala Gly Val Pro Gly Arg Val
                405                 410                 415
His Ile Thr Glu Ala Thr Leu Asn His Leu Asp Lys Ala Tyr Glu Val
                420                 425                 430
Glu Asp Gly His Gly Glu Gln Arg Asp Pro Tyr Leu Lys Glu Met Asn
            435                 440                 445
Ile Arg Thr Tyr Leu Val Ile Asp Pro Arg Ser Gln Gln Pro Pro Pro
        450                 455                 460
Pro Ser His His Leu Ser Lys Pro Lys Gly Asp Ala Thr Leu Lys Met
465                 470                 475                 480
Arg Ala Ser Val Arg Val Thr Arg Tyr Leu Glu Ser Trp Gly Ala Ala
                485                 490                 495
Arg Pro Phe Ala His Leu Asn His Arg Glu Ser Val Ser Ser Ser Glu
                500                 505                 510
Thr Pro Ile Ser Asn Gly Arg Arg Gln Lys Ala Ile Pro Leu Arg Arg
            515                 520                 525
His Arg Ala Pro Asp Arg Ser Ala Ser Pro Lys Gly Arg Leu Glu Asp
        530                 535                 540
Asp Cys Asp Asp Glu Met Leu Ser Ala Ile Glu Gly Leu Ser Ser Thr
545                 550                 555                 560
Arg Pro Cys Cys Ser Lys Ser Asp Asp Phe His Thr Phe Gly Pro Ile
                565                 570                 575
Phe Leu Glu Lys Gly Phe Glu Arg Glu Tyr Arg Leu Val Pro Ile Pro
            580                 585                 590
Arg Ala Arg Tyr Asp Phe Ala Cys Ala Ser Leu Val Phe Val Cys Ile
        595                 600                 605
Leu Leu Val His Leu Leu Val Met Pro Arg Met Ala Thr Leu Gly Val
        610                 615                 620
Ser Phe Gly Leu Val Ala Cys Leu Leu Gly Leu Val Leu Ser Phe Cys
625                 630                 635                 640
Phe Ala Thr Glu Phe Ser Arg Cys Phe Pro Ser Arg Ser Thr Leu Gln
                645                 650                 655
Ala Ile Ser Glu Ser Val Glu Thr Gln Pro Leu Val Arg Leu Val Leu
            660                 665                 670
```

-continued

```
Val Val Leu Thr Val Gly Ser Leu Thr Val Ala Ile Ile Asn Met
            675                 680                 685

Pro Leu Thr Leu Asn Pro Gly Pro Glu Gln Pro Gly Asp Asn Lys Thr
        690                 695                 700

Ser Pro Leu Ala Ala Gln Asn Arg Val Gly Thr Pro Tyr Glu Leu Leu
705                     710                 715                 720

Pro Tyr Tyr Thr Cys Ser Cys Ile Leu Gly Phe Ile Ala Cys Ser Val
                    725                 730                 735

Phe Leu Arg Met Ser Leu Glu Leu Lys Ala Met Leu Leu Thr Val Ala
                740                 745                 750

Leu Val Ala Tyr Leu Leu Leu Phe Asn Leu Ser Pro Cys Trp His Val
                755                 760                 765

Ser Gly Asn Ser Thr Glu Thr Asn Gly Thr Gln Arg Thr Arg Leu Leu
770                     775                 780

Leu Ser Asp Ala Gln Ser Met Pro Ser His Thr Leu Ala Pro Gly Ala
785                     790                 795                 800

Gln Glu Thr Ala Pro Ser Pro Ser Tyr Leu Glu Arg Asp Leu Lys Ile
                    805                 810                 815

Met Val Asn Phe Tyr Leu Ile Leu Phe Tyr Ala Thr Leu Ile Leu Leu
                820                 825                 830

Ser Arg Gln Ile Asp Tyr Tyr Cys Arg Leu Asp Cys Leu Trp Lys Lys
                835                 840                 845

Lys Phe Lys Lys Glu His Glu Glu Phe Glu Thr Met Glu Asn Val Asn
        850                 855                 860

Arg Leu Leu Leu Glu Asn Val Leu Pro Ala His Val Ala Ala His Phe
865                 870                 875                 880

Ile Gly Asp Lys Ala Ala Glu Asp Trp Tyr His Gln Ser Tyr Asp Cys
                    885                 890                 895

Val Cys Val Met Phe Ala Ser Val Pro Asp Phe Lys Val Phe Tyr Thr
                900                 905                 910

Glu Cys Asp Val Asn Lys Glu Gly Leu Glu Cys Leu Arg Leu Leu Asn
        915                 920                 925

Glu Ile Ile Ala Asp Phe Asp Glu Leu Leu Leu Lys Pro Lys Phe Ser
930                 935                 940

Gly Val Glu Lys Ile Lys Thr Ile Gly Ser Thr Tyr Met Ala Ala Ala
945                 950                 955                 960

Gly Leu Ser Ala Pro Ser Gly His Glu Asn Gln Asp Leu Glu Arg Lys
                    965                 970                 975

His Val His Ile Gly Val Leu Val Glu Phe Ser Met Ala Leu Met Ser
                980                 985                 990

Lys Leu Asp Gly Ile Asn Arg His Ser Phe Asn Ser Phe Arg Leu Arg
                995                 1000                1005

Val Gly Ile Asn His Gly Pro Val Ile Ala Gly Val Ile Gly Ala Arg
        1010                1015                1020

Lys Pro Gln Tyr Asp Ile Trp Gly Asn Thr Val Asn Val Ala Ser Arg
1025                1030                1035                1040

Met Glu Ser Thr Gly Glu Leu Gly Lys Ile Gln Val Thr Glu Glu Thr
                1045                1050                1055

Cys Thr Ile Leu Gln Gly Leu Gly Tyr Ser Cys Glu Cys Arg Gly Leu
                1060                1065                1070

Ile Asn Val Lys Gly Lys Gly Glu Leu Arg Thr Tyr Phe Val Cys Thr
                1075                1080                1085
```

Asp Thr Ala Lys Phe Gln Gly Leu Gly Leu Asn
   1090                 1095

(2) INFORMATION FOR SEQ ID NO:15:

(i) SEQUENCE CHARACTERISTICS:
        (A) LENGTH: 4601 base pairs
        (B) TYPE: nucleic acid
        (C) STRANDEDNESS: single
        (D) TOPOLOGY: linear (xi) SEQUENCE DESCRIPTION: SEQ ID NO:15:

```
CCAGAACTCG CGCTGTCAGT ATTTGCTCTG GAAGTGGCCA CAACCAGGAA GGAACCGAAG      60

AGAGAGCTTC ATCCAGCACA CCTCCAAATT AACTGTTTGG TGACTTGTTA GTGTTAAGGA     120

TACCACCTTT CTCCTGCCCT CCCGCGGGGC GCCCTGCCAC CTCACCATCA CCCACACCTC     180

CTGCCTCATC GCGCCCGCCT CCAGCTCCTC CCCGACTCCC CATGCCGGCG CAATGGAGTT     240

ATCCGAAGGG CGATGATTGC AGCCACAGCT GCTAACTTAG CACCCATCCT AGCCATCGGT     300

CACCCTTGGC CAGCCTTTCT GCAGCCGCCG AGACGTGGGC GTCCAGAGTC CAGTGCCGCA     360

GCCAGGACCC GCCCGACGCG CAGCAGAAGC GCGGCGCCCA GGCGCCTCTT AGAGAAGACT     420

GCGCCAAGAC GCTGAGCCTA GAGCCAGCCC AGGAGCTTGA GCGCAGAAAG GGACTGCGTG     480

GCTCAGAGTG CCGAGGATTT CGTGGACAAA TAGCCACCAC TTTCACTGCG TATCCCAACG     540

GAGCTGATTG GCGGGAAGGT GGCTTGCCAG TACGCAGGGG TCCACTGCAA TCTGCCAGGA     600

GCCCCTTGCT CTCGGGCTCA CTATGACTTG ACCTGTGGGG GCCCTGCTCA GGGCTCCTGC     660

AATCGAGCAG CCTAGGAAAG AGGGGATCGC TGCCAAGCGG CCTTCGGGTC TCTAAAAACC     720

CCTACCCGCA ACTGCCACAA CCAGTGTCTG AGCCTCCCTC CCTGCGGACC CCAGCCATGG     780

AACTCTCGGA TGTGCACTGC CTTAGCGGCA GCGAGGAACT CTATACCATT CACCCGACGC     840

CCCCGGCCGC GGACGGCGGG AGCGGCTCTC GGCCGCAGCG GCTGCTGTGG CAGACGGCGG     900

TGCGGCACAT CACCGAGCAG CGCTTCATCC ACGGCCACCG AGGCGGCGGC GGCGGGGGCT     960

CCCGCAAAGC CTCGAACCCT GCGGGCAGCG GACCAAACCA CCACGCGCCG CAGCTGTCTA    1020

GCGACTCGGT GCTGCCTCTC TATTCTCTGG GCTCCGGAGA GCGAGCGCAC AACACCGGTG    1080

GCACCAAAGT CTTTCCGGAA CGCAGCGGGA GCGGCAGTGC CAGTGGCAGC GGGGGTGGGG    1140

GCGACTTGGG CTTCCTGCAC CTTGACTGTG CCCCAAGTAA CTCGGATTTC TTCCTCAATG    1200

GGGGATACAG CTACCGTGGG GTCATTTTCC CAACCCTACG CAACTCCTTC AAGTCTCGGG    1260

ATCTGGAGCG CCTCTATCAA CGCTATTTCC TGGGCCAGAG GCGCAAATCG GAGGTAGTGA    1320

TGAACGTGCT GGATGTACTA ACCAAACTCA CCCTTCTAGT CCTTCACTTG AGCCTAGCCT    1380

CGGCTCCCAT GGACCCTCTC AAGGGCATCC TGCTAGGCTT TTTCACTGGC ATCGAGGTGG    1440

TGATCTGCGC CCTCGTGGTG GTCAGGAAGG ACACCACCTC CCACACTTAC CTGCAATACA    1500

GCGGCGTGGT CACTTGGGTG GCTATGACCA CCCAGATTCT GGCAGCAGGC CTGGGCTATG    1560

GGCTTCTGGG CGACGGCATA GGCTACGTGC TTTTTACACT CTTCGCCACC TACAGCATGC    1620

TTCCGCTGCC TCTCACCTGG GCCATCTTGG CCGGCCTGGG CACATCCTTG CTGCAAGTCA    1680

CACTTCAAGT GCTCATACCC AGACTAGCGG TCTTTTCCAT CAACCAGGTC CTGGCCCAGG    1740

TGGTGCTCTT CATGTGCATG AATACAGCAG GCATCTTCAT CAGTTACCTT TCAGACCGCG    1800

CCCAGCGGCA GGCCTTCCTG GAGACCCGGA GGTGTGTGGA GGCCAGGCTC CGCCTGGAGA    1860

CAGAGAACCA AAGACAGGAG CGGCTTGTGC TCTCTGTGCT CCCCAGGTTT GTCGTCCTAG    1920

AAATGATCAA TGACATGACC AATGTGGAGG ACGAGCACCT GCAGCATCAG TTCCACCGCA    1980
```

```
TCTACATCCA TCGCTACGAG AACGTCAGTA TTCTTTTTGC AGATGTCAAA GGATTTACCA    2040

ACCTCTCTAC GACCTTGTCT GCTCAGGAGC TTGTCAGGAT GCTCAACGAG CTCTTTGCCA    2100

GATTTGATCG GCTGGCCCAT GAGCATCACT GTCTTCGCAT TAAAATCCTG GGGGACTGCT    2160

ACTACTGTGT GTCAGGACTG CCTGAGCCCC GCCAGGACCA TGCTCATTGC TGTGTTGAAA    2220

TGGGCCTCAG CATGATCAAA ACTATCAGGT TTGTGAGGTC CAGAACGAAG CATGATGTTG    2280

ACATGCGAAT TGGAATCCAT TCAGGCTCTG TGCTGTGTGG TGTGTTGGGC CTGAGAAAAT    2340

GGCAGTTTGA TGTCTGGTCT TGGGATGTGG ACATCGCAAA CAAACTTGAA TCTGGAGGAA    2400

TCCCTGGGAG AATTCACATT TCCAAAGCCA CACTGGATTG CCTCAGTGGT GACTATAATG    2460

TGGAAGAGGG CCACGGTAAG GAGAGGAATG AATTCTTGAG GAAGCATAAT ATAGAGACCT    2520

ATTTGATTAA GCAGCCCGAG GAGAGTTTGC TATCCTTGCC TGAAGATATA GTTAAGGAGT    2580

CGGTGAGCTG CTCGGACAGG AGAAACAGTG GGCAACGTT CACAGAAGGA TCCTGGAGCC     2640

CAGAACTGCC ATTCGACAAC ATCGTGGGCA AACAGAATAC TCTGGCTGCC CTAACAAGAA    2700

ATTCAATAAA TCTGCTTCCA AACCATCTCG CACAAGCTTT GCATGTCCAG TCTGGGCCTG    2760

AGGAAATTAA CAAGAGAATA GAGCATACCA TCGACTTGCG GAGTGGCGAT AAGTTGAGAA    2820

GAGAGCATAT CAAGCCATTC TCACTGATGT TTAAAGACTC CAGCCTGGAG CACAAGTATT    2880

CTCAAATGCG GGATGAAGTA TTCAAGTCAA ACTTGGTCTG TGCATTTATC GTTCTTCTGT    2940

TTATCACTGC GATTCAAAGT TTGCTTCCTT CTTCGAGGCT GATGCCTATG ACCATCCAGT    3000

TCTCCATCCT GATCATGCTG CACTCCGCCC TGGTCCTCAT CACCACGGCA GAAGACTATA    3060

AGTGTCTGCC TCTCATTCTC CGCAAAACCT GTTGTTGGAT TAACGAGACC TATTTGGCCC    3120

GCAACGTCAT CATCTTTGCT TCCATCTTGA TTAATTTCCT GGGAGCCGTC ATAAATATTC    3180

TGTGGTGTGA TTTTGACAAG TCGATACCCT TGAAGAACCT GACTTTCAAT TCCTCAGCTG    3240

TGTTTACAGA TATCTGCTCC TACCCAGAGT ACTTTGTCTT CACTGGGGTG TTGGCCATGG    3300

TGACGTGTGC AGTATTTCTC CGGCTTAACT CTGTCCTGAA GCTGGCTGTG CTGCTCATTA    3360

TGATCGCCAT CTACGCCCTG CTGACAGAGA CCATCTATGC AGGTCTCTTT CTGAGTTATG    3420

ACAACCTGAA CCACAGTGGA GAAGATTTTC TGGGGACCAA GGAGGCATCA CTGCTACTGA    3480

TGGCCATGTT CCTTCTTGCT GTATTCTACC ATGGACAGCA GCTGGAGTAC ACAGCCCGCC    3540

TAGATTTCCT GTGGCGAGTA CAGGCCAAAG AGGAGATCAA CGAGATGAAG GACTTGAGGG    3600

AACACAATGA GAACATGCTT CGCAATATCT TACCCGGCCA CGTGGCCCGC CACTTCCTGG    3660

AGAAAGACAG AGACAATGAG GAGCTGTATT CTCAATCCTA TGATGCCGTT GGGGTAATGT    3720

TTGCCTCCAT TCCTGGATTT GCAGACTTTT ACTCTCAGAC AGAAATGAAC AACCAGGGAG    3780

TGGAATGTCT GCGCTTGCTG AATGAGATCA TTGCTGACTT TGATGAGTTA CTTGGAGAGG    3840

ACCGCTTTCA GGACATAGAG AAGATTAAGA CCATTGGTAG TACATACATG GCTGTCTCAG    3900

GACTGTCACC AGAGAAACAG CAATGTGAAG ATAAATGGGG ACATTTGTGT GCCCTGGCTG    3960

ACTTCTCTCT TGCCCTGACT GAAAGCATAC AAGAGATCAA CAAGCATTCG TTCAACAATT    4020

TTGAACTCCG TATTGGCATC AGCCATGGCT CAGTGGTAGC AGGTGTAATT GGCGCTAAGA    4080

AACCACAGTA TGACATTTGG GGTAAAACTG TGAACTTGGC AAGCCGAATG GACAGCACAG    4140

GAGTGAGTGG CCGGATCCAA GTTCCTGAGG AGACCTATCT CATCCTGAAG GATCAGGGCT    4200

TTGCCTTCGA CTACCGGGGA GAGATATATG TGAAGGGCAT CAGCGAACAA GAAGGGAAAA    4260

TCAAAACATA TTTTCTCCTG GGACGAGTCC AACCCAACCC ATTCATCTTA CCCCCAAGAA    4320
```

-continued

```
GACTTCCTGG GCAGTACTCT CTGGCTGCAG TTGTCCTTGG GCTTGTCCAG TCTCTCAACA    4380

GGCAAAGGCA GAAGCAACTA CTCAATGAGA ACAGCAACTC TGGCATCATC AAGAGCCATT    4440

ACAACCGGCG GACTTTGCTA ACGCCAAGTG GGCCAGAGCC TGGAGCACAG GCTGAAGGCA    4500

CTGACAAATC CGATTTGCCA TAAAAGCATT TTCTTTGTGT TTCTTTCTCT TTTTTTGTAT    4560

TTCTTTTATA TATAAAATAA ATATACTAAT AAAAAGGTTT G                       4601
```

(2) INFORMATION FOR SEQ ID NO:16:

(i) SEQUENCE CHARACTERISTICS:
        (A) LENGTH: 1248 amino acids
        (B) TYPE: amino acid
        (C) STRANDEDNESS:
        (D) TOPOLOGY: linear (xi) SEQUENCE DESCRIPTION: SEQ ID NO:16:

```
Met Glu Leu Ser Asp Val His Cys Leu Ser Gly Ser Glu Glu Leu Tyr
1               5                   10                  15

Thr Ile His Pro Thr Pro Ala Ala Asp Gly Gly Ser Gly Ser Arg
            20                  25                  30

Pro Gln Arg Leu Leu Trp Gln Thr Ala Val Arg His Ile Thr Glu Gln
            35                  40                  45

Arg Phe Ile His Gly His Arg Gly Gly Gly Gly Gly Ser Arg Lys
50                  55                  60

Ala Ser Asn Pro Ala Gly Ser Gly Pro Asn His His Ala Pro Gln Leu
65                  70                  75                  80

Ser Ser Asp Ser Val Leu Pro Leu Tyr Ser Leu Gly Ser Gly Glu Arg
                85                  90                  95

Ala His Asn Thr Gly Gly Thr Lys Val Phe Pro Glu Arg Ser Gly Ser
                100                 105                 110

Gly Ser Ala Ser Gly Ser Gly Gly Gly Asp Leu Gly Phe Leu His
                115                 120                 125

Leu Asp Cys Ala Pro Ser Asn Ser Asp Phe Phe Leu Asn Gly Gly Tyr
130                 135                 140

Ser Tyr Arg Gly Val Ile Phe Pro Thr Leu Arg Asn Ser Phe Lys Ser
145                 150                 155                 160

Arg Asp Leu Glu Arg Leu Tyr Gln Arg Tyr Phe Leu Gly Gln Arg Arg
                165                 170                 175

Lys Ser Glu Val Val Met Asn Val Leu Asp Val Leu Thr Lys Leu Thr
                180                 185                 190

Leu Leu Val Leu His Leu Ser Leu Ala Ser Ala Pro Met Asp Pro Leu
                195                 200                 205

Lys Gly Ile Leu Leu Gly Phe Phe Thr Gly Ile Glu Val Val Ile Cys
210                 215                 220

Ala Leu Val Val Val Arg Lys Asp Thr Thr Ser His Thr Tyr Leu Gln
225                 230                 235                 240

Tyr Ser Gly Val Val Thr Trp Val Ala Met Thr Thr Gln Ile Leu Ala
                245                 250                 255

Ala Gly Leu Gly Tyr Gly Leu Leu Gly Asp Gly Ile Gly Tyr Val Leu
                260                 265                 270

Phe Thr Leu Phe Ala Thr Tyr Ser Met Leu Pro Leu Pro Leu Thr Trp
            275                 280                 285

Ala Ile Leu Ala Gly Leu Gly Thr Ser Leu Leu Gln Val Thr Leu Gln
            290                 295                 300

Val Leu Ile Pro Arg Leu Ala Val Phe Ser Ile Asn Gln Val Leu Ala
```

```
305                 310                 315                 320
Gln Val Val Leu Phe Met Cys Met Asn Thr Ala Gly Ile Phe Ile Ser
                325                 330                 335
Tyr Leu Ser Asp Arg Ala Gln Arg Gln Ala Phe Leu Glu Thr Arg Arg
                340                 345                 350
Cys Val Glu Ala Arg Leu Arg Leu Glu Thr Glu Asn Gln Arg Gln Glu
                355                 360                 365
Arg Leu Val Leu Ser Val Leu Pro Arg Phe Val Val Leu Glu Met Ile
                370                 375                 380
Asn Asp Met Thr Asn Val Glu Asp Glu His Leu Gln His Gln Phe His
385                 390                 395                 400
Arg Ile Tyr Ile His Arg Tyr Glu Asn Val Ser Ile Leu Phe Ala Asp
                405                 410                 415
Val Lys Gly Phe Thr Asn Leu Ser Thr Thr Leu Ser Ala Gln Glu Leu
                420                 425                 430
Val Arg Met Leu Asn Glu Leu Phe Ala Arg Phe Asp Arg Leu Ala His
                435                 440                 445
Glu His His Cys Leu Arg Ile Lys Ile Leu Gly Asp Cys Tyr Tyr Cys
                450                 455                 460
Val Ser Gly Leu Pro Glu Pro Arg Gln Asp His Ala His Cys Cys Val
465                 470                 475                 480
Glu Met Gly Leu Ser Met Ile Lys Thr Ile Arg Phe Val Arg Ser Arg
                485                 490                 495
Thr Lys His Asp Val Asp Met Arg Ile Gly Ile His Ser Gly Ser Val
                500                 505                 510
Leu Cys Gly Val Leu Gly Leu Arg Lys Trp Gln Phe Asp Val Trp Ser
                515                 520                 525
Trp Asp Val Asp Ile Ala Asn Lys Leu Glu Ser Gly Gly Ile Pro Gly
                530                 535                 540
Arg Ile His Ile Ser Lys Ala Thr Leu Asp Cys Leu Ser Gly Asp Tyr
545                 550                 555                 560
Asn Val Glu Glu Gly His Gly Lys Glu Arg Asn Glu Phe Leu Arg Lys
                565                 570                 575
His Asn Ile Glu Thr Tyr Leu Ile Lys Gln Pro Glu Glu Ser Leu Leu
                580                 585                 590
Ser Leu Pro Glu Asp Ile Val Lys Glu Ser Val Ser Cys Ser Asp Arg
                595                 600                 605
Arg Asn Ser Gly Ala Thr Phe Thr Glu Gly Ser Trp Ser Pro Glu Leu
                610                 615                 620
Pro Phe Asp Asn Ile Val Gly Lys Gln Asn Thr Leu Ala Ala Leu Thr
625                 630                 635                 640
Arg Asn Ser Ile Asn Leu Leu Pro Asn His Leu Ala Gln Ala Leu His
                645                 650                 655
Val Gln Ser Gly Pro Glu Glu Ile Asn Lys Arg Ile Glu His Thr Ile
                660                 665                 670
Asp Leu Arg Ser Gly Asp Lys Leu Arg Arg Glu His Ile Lys Pro Phe
                675                 680                 685
Ser Leu Met Phe Lys Asp Ser Ser Leu Glu His Lys Tyr Ser Gln Met
                690                 695                 700
Arg Asp Glu Val Phe Lys Ser Asn Leu Val Cys Ala Phe Ile Val Leu
705                 710                 715                 720
Leu Phe Ile Thr Ala Ile Gln Ser Leu Leu Pro Ser Ser Arg Leu Met
                725                 730                 735
```

-continued

```
Pro Met Thr Ile Gln Phe Ser Ile Leu Ile Met Leu His Ser Ala Leu
                740                 745                 750

Val Leu Ile Thr Thr Ala Glu Asp Tyr Lys Cys Leu Pro Leu Ile Leu
            755                 760                 765

Arg Lys Thr Cys Cys Trp Ile Asn Glu Thr Tyr Leu Ala Arg Asn Val
        770                 775                 780

Ile Ile Phe Ala Ser Ile Leu Ile Asn Phe Leu Gly Ala Val Ile Asn
785                 790                 795                 800

Ile Leu Trp Cys Asp Phe Asp Lys Ser Ile Pro Leu Lys Asn Leu Thr
                805                 810                 815

Phe Asn Ser Ser Ala Val Phe Thr Asp Ile Cys Ser Tyr Pro Glu Tyr
            820                 825                 830

Phe Val Phe Thr Gly Val Leu Ala Met Val Thr Cys Ala Val Phe Leu
        835                 840                 845

Arg Leu Asn Ser Val Leu Lys Leu Ala Val Leu Leu Ile Met Ile Ala
    850                 855                 860

Ile Tyr Ala Leu Leu Thr Glu Thr Ile Tyr Ala Gly Leu Phe Leu Ser
865                 870                 875                 880

Tyr Asp Asn Leu Asn His Ser Gly Glu Asp Phe Leu Gly Thr Lys Glu
                885                 890                 895

Ala Ser Leu Leu Leu Met Ala Met Phe Leu Leu Ala Val Phe Tyr His
            900                 905                 910

Gly Gln Gln Leu Glu Tyr Thr Ala Arg Leu Asp Phe Leu Trp Arg Val
        915                 920                 925

Gln Ala Lys Glu Glu Ile Asn Glu Met Lys Asp Leu Arg Glu His Asn
    930                 935                 940

Glu Asn Met Leu Arg Asn Ile Leu Pro Gly His Val Ala Arg His Phe
945                 950                 955                 960

Leu Glu Lys Asp Arg Asp Asn Glu Glu Leu Tyr Ser Gln Ser Tyr Asp
                965                 970                 975

Ala Val Gly Val Met Phe Ala Ser Ile Pro Gly Phe Ala Asp Phe Tyr
            980                 985                 990

Ser Gln Thr Glu Met Asn Asn Gln Gly Val Glu Cys Leu Arg Leu Leu
        995                 1000                1005

Asn Glu Ile Ile Ala Asp Phe Asp Glu Leu Leu Gly Glu Asp Arg Phe
    1010                1015                1020

Gln Asp Ile Glu Lys Ile Lys Thr Ile Gly Ser Thr Tyr Met Ala Val
1025                1030                1035                1040

Ser Gly Leu Ser Pro Glu Lys Gln Gln Cys Glu Asp Lys Trp Gly His
                1045                1050                1055

Leu Cys Ala Leu Ala Asp Phe Ser Leu Ala Leu Thr Glu Ser Ile Gln
            1060                1065                1070

Glu Ile Asn Lys His Ser Phe Asn Asn Phe Glu Leu Arg Ile Gly Ile
        1075                1080                1085

Ser His Gly Ser Val Val Ala Gly Val Ile Gly Ala Lys Lys Pro Gln
    1090                1095                1100

Tyr Asp Ile Trp Gly Lys Thr Val Asn Leu Ala Ser Arg Met Asp Ser
1105                1110                1115                1120

Thr Gly Val Ser Gly Arg Ile Gln Val Pro Glu Glu Thr Tyr Leu Ile
                1125                1130                1135

Leu Lys Asp Gln Gly Phe Ala Phe Asp Tyr Arg Gly Glu Ile Tyr Val
            1140                1145                1150
```

```
Lys Gly Ile Ser Glu Gln Glu Gly Lys Ile Lys Thr Tyr Phe Leu Leu
        1155                1160                1165

Gly Arg Val Gln Pro Asn Pro Phe Ile Leu Pro Pro Arg Arg Leu Pro
        1170                1175                1180

Gly Gln Tyr Ser Leu Ala Ala Val Val Leu Gly Leu Val Gln Ser Leu
1185                1190                1195                1200

Asn Arg Gln Arg Gln Lys Gln Leu Leu Asn Glu Asn Ser Asn Ser Gly
                1205                1210                1215

Ile Ile Lys Ser His Tyr Asn Arg Arg Thr Leu Leu Thr Pro Ser Gly
            1220                1225                1230

Pro Glu Pro Gly Ala Gln Ala Glu Gly Thr Asp Lys Ser Asp Leu Pro
        1235                1240                1245

(2) INFORMATION FOR SEQ ID NO:17:

(i) SEQUENCE CHARACTERISTICS:
        (A) LENGTH: 1652 base pairs
        (B) TYPE: nucleic acid
        (C) STRANDEDNESS: single
        (D) TOPOLOGY: linear (xi) SEQUENCE DESCRIPTION: SEQ ID NO:17:
```

| | | | | | |
|---|---|---|---|---|---|
| ACCATGGCTG | AGCGCGCCCA | GAGGAAGGCC | TTCCTGCAGG | CCCGGAACTG | CATTGAGGAC | 60 |
| CGGCTGAGGC | TGGAGGATGA | GAATGAGAAG | CAGGAGCGGC | TGCTCATGAG | CCTCCTGCCT | 120 |
| CGGAATGTTG | CTATGGAGAT | GAAGGAGGAC | TTCCTGAAGC | CCCCTGAGAG | GATTTTCCAC | 180 |
| AAGATTTACA | TCCAGCGGCA | TGACAACGTG | AGCATCCTCT | TTGCAGACAT | CGTGGGCTTC | 240 |
| ACAGGCTTGG | CGTCACAGTG | CACGGCCCAG | GAGCTGGTGA | AACTCCTCAA | TGAGCTCTTC | 300 |
| GGGAAGTTTG | ACGAGCTGGC | CACAGAGAAC | CACTGCCGCC | GCATCAAGAT | CCTGGGAGAT | 360 |
| TGCTACTACT | GCGTGTCTGG | CCTCACTCAG | CCCAAGACTG | ACCACGCCCA | CTGCTGTGTG | 420 |
| GAGATGGGCC | TGGACATGAT | CGACACCATC | ACGTCCGTGG | CTGAGGCCAC | TGAGGTGGAC | 480 |
| TTGAACATGC | GTGTGGGGCT | GCACACCGGC | AGGGTCCTCT | GCGGGGTCCT | GGGCCTGCGT | 540 |
| AAGTGGCAGT | ATGATGTGTG | GTCCAACGAC | GTGACCCTGG | CCAACGTCAT | GGAGGCTGCC | 600 |
| GGCCTGCCTG | GAAGGTTCA | CATCACAAAG | ACCACCCTGG | CGTGCCTGAA | TGGTGACTAT | 660 |
| GAGGTGGAGC | CGGGACACGG | ACACGAGAGG | AACAGTTTTC | TGAAAACTCA | TAACATTGAG | 720 |
| ACCTTTTTTA | TTGTGCCCTC | GCATCGGCGA | GCGGCCGCTG | GAGGCATGCC | TCCAGCGGCC | 780 |
| GCTGGAGGCA | TGAGACAGAG | TGAATATTAC | TGTAGGTTAG | ACTTCTTGTG | GAAGAACAAG | 840 |
| TTCAAAAAAG | AGCGGGAGGA | GATAGAAACC | ATGGAGAACC | TAAATCGAGT | GCTGCTGGAG | 900 |
| AACGTGCTTC | CTGCACACGT | GGCTGAACAC | TTCCTGGCCA | GGAGCCTGAA | AAATGAGGAG | 960 |
| CTGTACCACC | AGTCCTACGA | CTGTGTCTGT | GTCATGTTTG | CCTCCATTCC | GGACTTCAAG | 1020 |
| GAGTTCTACA | CAGAGTCAGA | TGTGAACAAG | GAAGGCTTGA | ATGCCTGCG | GCTCCTGAAT | 1080 |
| GAGATCATTG | CTGACTTTGA | TGATCTGCTT | TCTAAGCCAA | AGTTCAGTGG | TGTTGAAAAG | 1140 |
| ATCAAGACCA | TTGGGAGCAC | ATACATGGCA | GCCACGGGAC | TGAGTGCCAT | ACCCAGCCAG | 1200 |
| GAGCACGCCC | AGGAACCTGA | GCGTCAGTAC | ATGCACATAG | CACCATGGT | GGAGTTTGCA | 1260 |
| TATGCCCTGG | TGGAAAAACT | GGATGCCATC | AATAAGCACT | CCTTCAACGA | CTTCAAACTG | 1320 |
| CGAGTGGGTA | TCAACCATGG | GCCTGTAATA | GCTGGCGTCA | TAGGGCTCA | AAAGCCACAG | 1380 |
| TATGACATCT | GGGCAACAC | TGTCAACGTG | GCCAGCAGAA | TGGACAGCAC | CGGGGTCCTG | 1440 |
| GACAAAATAC | AGGTGACTGA | GGAGACAAGC | CTCATCTTGC | AGACGCTTGG | CTACACGTGT | 1500 |

-continued

```
ACATGTCGAG GTATCATCAA TGTGAAGGGG AAAGGGGACC TGAAGACATA TTTTGTAAAC      1560

ACAGAGATGT CAAGGTCCCT TTCTCAGAGC AACTTGGCAT CCTGAGAAGC TGTCTCTTCC      1620

TGACAAGAAG AATGTACTTG CAGGAAGGTA CC                                    1652
```

(2) INFORMATION FOR SEQ ID NO:18:

(i) SEQUENCE CHARACTERISTICS:
        (A) LENGTH: 533 amino acids
        (B) TYPE: amino acid
        (C) STRANDEDNESS:
        (D) TOPOLOGY: linear (xi) SEQUENCE DESCRIPTION: SEQ ID NO:18:

```
Met Ala Glu Arg Ala Gln Arg Lys Ala Phe Leu Gln Ala Arg Asn Cys
  1               5                  10                  15

Ile Glu Asp Arg Leu Arg Leu Glu Asp Glu Asn Glu Lys Gln Glu Arg
             20                  25                  30

Leu Leu Met Ser Leu Leu Pro Arg Asn Val Ala Met Glu Met Lys Glu
         35                  40                  45

Asp Phe Leu Lys Pro Pro Glu Arg Ile Phe His Lys Ile Tyr Ile Gln
 50                  55                  60

Arg His Asp Asn Val Ser Ile Leu Phe Ala Asp Ile Val Gly Phe Thr
 65                  70                  75                  80

Gly Leu Ala Ser Gln Cys Thr Ala Gln Glu Leu Val Lys Leu Leu Asn
                 85                  90                  95

Glu Leu Phe Gly Lys Phe Asp Glu Leu Ala Thr Glu Asn His Cys Arg
            100                 105                 110

Arg Ile Lys Ile Leu Gly Asp Cys Tyr Tyr Cys Val Ser Gly Leu Thr
            115                 120                 125

Gln Pro Lys Thr Asp His Ala His Cys Cys Val Glu Met Gly Leu Asp
130                 135                 140

Met Ile Asp Thr Ile Thr Ser Val Ala Glu Ala Thr Glu Val Asp Leu
145                 150                 155                 160

Asn Met Arg Val Gly Leu His Thr Gly Arg Val Leu Cys Gly Val Leu
                165                 170                 175

Gly Leu Arg Lys Trp Gln Tyr Asp Val Trp Ser Asn Asp Val Thr Leu
            180                 185                 190

Ala Asn Val Met Glu Ala Ala Gly Leu Pro Gly Lys Val His Ile Thr
            195                 200                 205

Lys Thr Thr Leu Ala Cys Leu Asn Gly Asp Tyr Glu Val Glu Pro Gly
210                 215                 220

His Gly His Glu Arg Asn Ser Phe Leu Lys Thr His Asn Ile Glu Thr
225                 230                 235                 240

Phe Phe Ile Val Pro Ser His Arg Arg Ala Ala Ala Gly Gly Met Pro
                245                 250                 255

Pro Ala Ala Ala Gly Gly Met Arg Gln Ser Glu Tyr Tyr Cys Arg Leu
            260                 265                 270

Asp Phe Leu Trp Lys Asn Lys Phe Lys Lys Glu Arg Glu Glu Ile Glu
            275                 280                 285

Thr Met Glu Asn Leu Asn Arg Val Leu Leu Glu Asn Val Leu Pro Ala
        290                 295                 300

His Val Ala Glu His Phe Leu Ala Arg Ser Leu Lys Asn Glu Glu Leu
305                 310                 315                 320

Tyr His Gln Ser Tyr Asp Cys Val Cys Val Met Phe Ala Ser Ile Pro
                325                 330                 335
```

```
Asp Phe Lys Glu Phe Tyr Thr Glu Ser Asp Val Asn Lys Glu Gly Leu
            340                 345                 350

Glu Cys Leu Arg Leu Leu Asn Glu Ile Ile Ala Asp Phe Asp Asp Leu
            355                 360                 365

Leu Ser Lys Pro Lys Phe Ser Gly Val Glu Lys Ile Lys Thr Ile Gly
            370                 375                 380

Ser Thr Tyr Met Ala Ala Thr Gly Leu Ser Ala Ile Pro Ser Gln Glu
385                 390                 395                 400

His Ala Gln Glu Pro Glu Arg Gln Tyr Met His Ile Gly Thr Met Val
            405                 410                 415

Glu Phe Ala Tyr Ala Leu Val Gly Lys Leu Asp Ala Ile Asn Lys His
            420                 425                 430

Ser Phe Asn Asp Phe Lys Leu Arg Val Gly Ile Asn His Gly Pro Val
            435                 440                 445

Ile Ala Gly Val Ile Gly Ala Gln Lys Pro Gln Tyr Asp Ile Trp Gly
            450                 455                 460

Asn Thr Val Asn Val Ala Ser Arg Met Asp Ser Thr Gly Val Leu Asp
465                 470                 475                 480

Lys Ile Gln Val Thr Glu Glu Thr Ser Leu Ile Leu Gln Thr Leu Gly
            485                 490                 495

Tyr Thr Cys Thr Cys Arg Gly Ile Ile Asn Val Lys Gly Lys Gly Asp
            500                 505                 510

Leu Lys Thr Tyr Phe Val Asn Thr Glu Met Ser Arg Ser Leu Ser Gln
            515                 520                 525

Ser Asn Leu Ala Ser
    530
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:19:

```
Ala Ala Ala Gly Gly Met
1               5
```

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:20:

```
Ala Ala Ala Gly Gly Met Pro Pro Ala Ala Ala Gly Gly Met
1               5                   10
```

(2) INFORMATION FOR SEQ ID NO:21:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:21:

```
Ala Ala Ala Gly Gly Met Pro Pro Ala Ala Ala Gly Gly Met Pro Pro
1               5                   10                  15
Ala Ala Ala Gly Gly Met
            20
```

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:22:

GGCCGCTCAC CATCACCATC ACCATTAGG                             29

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:23:

AATTCCTAAT GGTGATGGTG ATGGTGAGA                             29

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:24:

GATCCATCAT GAGACAGAGT GAAT                                  24

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

ATTCACTCTG TCTCATGATC                                       20

(2) INFORMATION FOR SEQ ID NO:26:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:26:

GGCCGCTGGA GG                                               12

(2) INFORMATION FOR SEQ ID NO:27:

(i) SEQUENCE CHARACTERISTICS:
        (A) LENGTH: 12 base pairs
        (B) TYPE: nucleic acid
        (C) STRANDEDNESS: single
        (D) TOPOLOGY: linear

```
    (xi) SEQUENCE DESCRIPTION: SEQ ID NO:27:

GATGCCTCCA GC                                                              12

(2) INFORMATION FOR SEQ ID NO:28:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (xi) SEQUENCE DESCRIPTION: SEQ ID NO:28:

GATCTAGCTA GCTA                                                            14

(2) INFORMATION FOR SEQ ID NO:29:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (xi) SEQUENCE DESCRIPTION: SEQ ID NO:29:

TAGCTAGCTA                                                                 10

(2) INFORMATION FOR SEQ ID NO:30:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:30:

ATGAGATCTG GATGCCAAGT TGCTCTGAG                                            29

(2) INFORMATION FOR SEQ ID NO:31:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:31:

TGGAGTCATG ACACAGAGTG AAT                                                  23
```